US010287314B2

(12) United States Patent
Bian et al.

(10) Patent No.: US 10,287,314 B2
(45) Date of Patent: *May 14, 2019

(54) METHODS OF REDUCING LEVEL OF ONE OR MORE IMPURITIES IN A SAMPLE DURING PROTEIN PURIFICATION

(71) Applicant: EMD Millipore Corporation, Burlington, MA (US)

(72) Inventors: Nanying Bian, Lexington, MA (US); Christopher Gillespie, Shirley, MA (US); Matthew T. Stone, Cambridge, MA (US); Mikhail Kozlov, Lexington, MA (US); Jie Chen, Stow, MA (US); Martin Siwak, Topsfield, MA (US)

(73) Assignee: EMD Millipore Corporation, Burlington, MA (US)

( * ) Notice: Subject to any disclaimer, the term of this patent is extended or adjusted under 35 U.S.C. 154(b) by 501 days.

This patent is subject to a terminal disclaimer.

(21) Appl. No.: 14/747,029

(22) Filed: Jun. 23, 2015

(65) Prior Publication Data

US 2016/0016992 A1 Jan. 21, 2016

Related U.S. Application Data

(63) Continuation of application No. 13/565,463, filed on Aug. 2, 2012, now Pat. No. 9,096,648.

(60) Provisional application No. 61/666,240, filed on Jun. 29, 2012, provisional application No. 61/572,349, filed on Aug. 19, 2011.

(51) Int. Cl.
| | |
|---|---|
| *B01D 15/36* | (2006.01) |
| *B01D 15/12* | (2006.01) |
| *B01D 15/18* | (2006.01) |
| *B01D 15/38* | (2006.01) |
| *B01J 39/26* | (2006.01) |
| *B01J 41/20* | (2006.01) |
| *C07K 1/36* | (2006.01) |
| *C07K 1/16* | (2006.01) |
| *B01J 20/282* | (2006.01) |
| *C07K 1/20* | (2006.01) |
| *B01J 43/00* | (2006.01) |
| *B01J 47/04* | (2006.01) |
| *C07K 16/00* | (2006.01) |
| *B01J 20/20* | (2006.01) |

(52) U.S. Cl.
CPC .............. *C07K 1/36* (2013.01); *B01D 15/125* (2013.01); *B01D 15/362* (2013.01); *B01D 15/363* (2013.01); *B01J 20/20* (2013.01); *B01J 20/282* (2013.01); *B01J 39/26* (2013.01); *B01J 41/20* (2013.01); *B01J 43/00* (2013.01); *B01J 47/04* (2013.01); *C07K 1/16* (2013.01); *C07K 1/20* (2013.01); *C07K 16/00* (2013.01); *B01D 15/1871* (2013.01); *B01D 15/3809* (2013.01); *C07K 2317/10* (2013.01)

(58) Field of Classification Search
None
See application file for complete search history.

(56) References Cited

U.S. PATENT DOCUMENTS

| 31,093 A | 1/1861 | Smith |
|---|---|---|
| 4,639,513 A * | 1/1987 | Hou .................... B01J 20/3217 424/177.1 |
| 4,816,567 A | 3/1989 | Cabilly et al. |
| 5,075,425 A * | 12/1991 | Kotitschke ........... C07K 16/065 424/177.1 |
| 5,162,286 A | 11/1992 | MacDowall |
| 5,204,310 A | 4/1993 | Tolles et al. |
| 5,219,999 A | 6/1993 | Suzuki et al. |
| 9,096,648 B2 * | 8/2015 | Bian .................... B01D 15/362 |
| 2006/0030696 A1 | 2/2006 | Bonnerjea et al. |
| 2010/0311952 A1 | 12/2010 | Falkenstein et al. |
| 2011/0040075 A1 | 2/2011 | Bonnerjea et al. |
| 2013/0245139 A1 * | 9/2013 | Kozlov .................... C07K 1/22 521/27 |

FOREIGN PATENT DOCUMENTS

| EP | 0180766 A2 | 5/1986 | |
|---|---|---|---|
| EP | 1577319 A1 | 9/2005 | |
| EP | 1577319 A1 * | 9/2005 | ........... B01D 15/125 |
| JP | 59-18731 A | 1/1984 | |
| JP | 61-087631 A | 5/1986 | |
| JP | 2003-512170 A | 4/2003 | |
| JP | 2006-508643 A | 3/2006 | |
| JP | 2007-525412 A | 9/2007 | |
| JP | 2010-528076 A | 8/2010 | |
| JP | 2010-279461 A | 12/2010 | |
| WO | 2003/072640 A2 | 9/2003 | |
| WO | 2004/076485 A1 | 9/2004 | |

(Continued)

OTHER PUBLICATIONS

GE Healthcare Life Sciences "DEAE Sephadex A-50" product data page, printed on Jun. 6, 2017.*
Faanes et al. "Buffer Tank Design for Acceptable Control Performance" Ind. Eng. Chem. Res. Apr. 4, 2003, pp. 1-23 (Year: 2003).*
Shukla et al. ":Process Scale Bioseparations for the Biopharmaceutical Indstury", Taylor & Francis, 2007, pp. 1-574 (Year: 2007).*
Extended European Search Report received for European Patent Application No. 12179861.5, dated Mar. 5, 2013, 4 pages.
International Preliminary Report on Patentability received for PCT Patent Application No. PCT/US2012/049351, dated Mar. 6, 2014, 6 pages.

(Continued)

*Primary Examiner* — Daniel E Kolker
*Assistant Examiner* — James L Rogers
(74) *Attorney, Agent, or Firm* — EMD Millipore Corporation

(57) ABSTRACT

The present invention provides novel and improved protein purification processes which incorporate certain types of carbonaceous materials and result in effective and selective removal of certain undesirable impurities without adversely effecting the yield of the desired protein product.

23 Claims, 22 Drawing Sheets

(56) References Cited

FOREIGN PATENT DOCUMENTS

| WO | 2005/077130 A2 | 8/2005 |
|---|---|---|
| WO | 2007/063129 A2 | 6/2007 |
| WO | 2007/067689 A2 | 6/2007 |
| WO | 2008/025747 A1 | 3/2008 |
| WO | 2011/012726 A2 | 2/2011 |
| WO | 2011/031397 A1 | 3/2011 |
| WO | 2011/037522 A1 | 3/2011 |
| WO | 2011/090720 A2 | 7/2011 |

OTHER PUBLICATIONS

International Search Report and Written Opinion received for PCT Patent Application No. PCT/US2012/049351, dated Jul. 1, 2013, 16 pages.
Brorson et al., "Identification of Protein a Media Performance Attributes that can be Monitored as Surrogates for Retrovirus Clearance During Extended Re-use", Journal of Chromatography A, vol. 989, 2003, pp. 155-163.
Chen et al., "Comparison of Standard and New Generation Hydrophobic Interaction Chromatography Resins in the Monoclonal Antibody Purification Process", Journal of Chromatography A, vol. 1177, 2008, pp. 272-281.
Chen, Raymond F., "Removal of Fatty Acids from Serum Albumin by Charcoal Treatment", The Journal of Biological Chemistry, vol. 242, No. 2, Jan. 1967, pp. 173-181.
Chothia et al., "Canonical Structures for the Hypervariable Regions of Immunoglobulins", J. Mol. Biol., vol. 196, 1987, pp. 901-917.
Clackson et al., "Making Antibody Fragments using Phage Display Libraries", Nature, vol. 352, Aug. 15, 1991, pp. 624-628.
Corbett, M. K., "Purification of Potato Virus X Without Aggregation", Virology, vol. 15, 1961, pp. 8-15.
Desportes et al., "Liquid Chromatographic Fractionation of Small Peptides from Wine", Journal of Cluomatography, vol. 893, 2000, pp. 281-291.
Faanes et al., "Buffer Tank Design for Acceptable Control Performance", Ind. Eng. Chem. Res., Apr. 4, 2003, pp. 1-23.
Fahrner et al., "Industrial Purification of Pharmaceutical Antibodies: Development, Operation, and Validation of Chromatography Processes", Biotechnology and Genetic Engineering Reviews., vol. 18, Jul. 2001, pp. 301-327.
Follman et al., "Factorial Screening of Antibody Purification Processes using three Chromatography Steps without Protein A", Journal of Chromatography A, vol. 1024, 2004, pp. 79-85.
How et al., "Removal of Phenolic Compounds from Soy Protein Extracts Using Activated Carbon", Journal of Food Science, vol. 47, 1982, pp. 933-940.
Jiang et al., "A Mechanistic Study of Protein a Chromatography Resin Lifetime", Journal of Chromatography A, vol. 1216, 2009, pp. 5849-5855.
Jones et al., "Replacing the Complementarity-Determining Regions in a Human Antibody with those from a Mouse", Nature, vol. 321, May 29, 1986, pp. 522-525.
Kabat et al., Sequences of proteins of immunological interest, 5th edition, Bethesda, MD : U.S. Dept. of Health and Human Services, Public Health Service, National Institutes of Health, 1991.
Kohler et al., "Continuous Cultures of Fused Cells Secreting Antibody of Predefined Specificity", Nature, vol. 256, Aug. 7, 1975, pp. 495-497.
Liu et al., "Recovery and Purification Process Development for Monoclonal Antibody Production", mAbs, Landes Bioscience, vol. 2, No. 5, Oct. 2010, pp. 480-499.
Marks et al., By-passing Immunization Human Antibodies from V-gene Libraries Displayed on Phage, J. Mol. Biol., vol. 222, 1991, pp. 581-597.
Marsh et al., "Applicability of Activated Carbon", Activated Carbon, Chapter 8, Aug. 2006, pp. 383-453.
McLean et al., Purification of Lettuce Necrotic Yellows Virus by Column Chromatography on Calcium Phosphate Gel Virology, vol. 31, 1967, pp. 585-591.
Morrison et al., "Chimeric Human Antibody molecules: Mouse Antigen-Binding Domains with Human Constant Region Domains", Proc. Natl. Acad. Sci. USA, vol. 81, Nov. 1984, pp. 6851-6855.
Nakano et al., "Activated Carbon Beads for the Removal of Highly Albumin-Bound Species", Analytical Biochemistry, vol. 129, 1983, pp. 64-71.
Nikolaev et al., "High-Porosity Activated Carbons for Bilirubin Removal", The International Journal of Artifical Organs, vol. 14, No. 3, 1991, pp. 179-185.
Presta, Leonard G., "Antibody Engineering", Current Opinion in Structural Biology, vol. 2, No. 4, 1992, pp. 593-596.
Price, W. C., "Purification and Crystallization of Southern Bean Mosaic Virus", American Journal of Botany, vol. 33, Jan. 1946, pp. 45-54.
Riechmann et al., "Reshaping Human Antibodies for Therapy", Nature, vol. 332, Mar. 24, 1988, pp. 323-327.
Shukla et al., "Downstream Processing of Monoclonal Antibodies—Application of Platform Approaches", Journal of Chromatography B, vol. 848, 2007, pp. 28-39.
Shukla et al., "Process Scale Bioseparations for the Biopharmaceutical Industry", CRC Press, Taylor & Francis Group, 2007, 573 pages.
Stein et al., "Cation Exchange Chromatography in Antibody Purification: pH Screening for Optimised Binding and HCP Removal", Journal of Chromatography B, vol. 848, 2007, pp. 151-158.
Wang et al., "Mineralization of an Azo Dye Acid Red 14 by Electro-Fenton's Reagent Using an Activated Carbon Fiber Cathode", Dyes and Pigments, vol. 65, 2005, pp. 227-233.
Zhang et al., "Synthesis of an Affinity Adsorbent based on Silica Gel and its Application in Endotoxin Removal", Reactive and Functional Polymers, vol. 67, 2007, pp. 728-736.
Zhou et al., "pH—Conductivity Hybrid Gradient Cation-Exchange Chromatography for Process-Scale Monoclonal Antibody Purification", Journal of Chromatography A, vol. 1175, 2007, pp. 69-80.
Extended European Search Report received for European Application No. 15159525.3, dated Sep. 25, 2015, 6 pages.

* cited by examiner

US 10,287,314 B2

METHODS OF REDUCING LEVEL OF ONE OR MORE IMPURITIES IN A SAMPLE DURING PROTEIN PURIFICATION

RELATED APPLICATIONS

The present application is a continuation application of U.S. patent application Ser. No. 13/565,463, filed on Aug. 2, 2012, which claims the benefit of priority of U.S. Provisional Patent Application Nos. 61/666,240, filing date Jun. 29, 2012, and U.S. Provisional Patent Application No. 61/575,349, filing date Aug. 19, 2011, each of which is incorporated by reference herein in its entirety.

FIELD OF THE INVENTION

The present invention relates to improved chromatography methods and methods of reducing the level of one or more impurities during protein purification.

BACKGROUND

Chromatography is a dominant purification technique in the purification of biological materials, e.g., monoclonal antibodies.

Commonly used chromatography methods include one or more of affinity chromatography media, ion exchange chromatography media, hydrophobic interaction, hydrophilic interaction, size exclusion and mixed mode (i.e., combination of various chromatography interactions) chromatography. For example, for the purification of monoclonal antibodies, a typical purification process includes an initial Protein A affinity capture step followed by one or more ion exchange polishing steps, the purpose of which is to reduce the level of one or more impurities such as, e.g., host cell protein (HCP). Further, other chromatography techniques, such as: bind and elute hydrophobic interaction chromatography (HIC); flow-through hydrophobic interaction chromatography (FTHIC); flow-through anion-exchange chromatography (AEX); weak partitioning chromatography with cation-exchange, anion-exchange, or hydrophobic interaction reins; mixed mode chromatography techniques, e.g., bind and elute weak cation and anion exchange, bind and elute hydrophobic and ion exchange interaction and flow-through hydrophobic and ion exchange mixed mode interaction (FTMM), both of which can utilize resins such as Capto™ Adhere, Capto™ MMC, HEA Hypercel™, PPA Hypercel™, may be used. Additionally, hydrophobic charge induction (HCI) chromatography along with others and combinations of various techniques can be used for polishing.

Although, chromatography offers many advantages for protein purification on a smaller scale, on a large scale, packing of chromatography columns is not only labor and time intensive but also expensive. Further, fouling of chromatography columns is a common problem, resulting in a user having to dispose off columns, which is undesirable, especially due to the high cost of chromatography resins.

Recently, there has been a noticeable trend in the industry to try and reduce the number of steps in protein purification processes. Also, use of techniques for obtaining a higher expression titer using bioreactors is a rising trend in the industry. The combination of these two trends has resulted in more product being loaded onto a column, thereby resulting in increased burden of fairly expensive chromatography media as well as lower product purity, both of which are undesirable.

SUMMARY OF THE INVENTION

The present invention is based, at least in part, on the surprising and unexpected discovery that certain materials (e.g., carbonaceous material such as activated carbon) can be incorporated into chromatography column based protein purification processes in a flow-through mode, resulting in reducing the burden of chromatography columns, and consequently increasing the life span of chromatography columns.

Further, the present invention is based on the surprising and unexpected discovery that carbonaceous material (e.g., activated carbon) can be used either upstream or downstream of a capture chromatography step to reduce the level of one or more impurities. In some embodiments according to the claimed methods, a sample is contacted with a carbonaceous material before a cation exchange (CEX) chromatography step. In other embodiments, a cation exchange (CEX) chromatography step is used before contacting a sample with a carbonaceous material. In yet other embodiments, a sample is contacted with a carbonaceous material after a Protein A affinity capture step. Alternatively, the Protein A affinity chromatography step may be used after contacting the sample with a carbonaceous material. In certain embodiments, the Protein A affinity capture step may be followed by an anion exchange (AEX) flow-through chromatography step and with or without a CEX chromatography bind/elute step. In still other embodiments, the carbonaceous material may be used after a non-affinity capture step (e.g., using CEX bind and elute chromatography as a capture step) and is followed by an AEX chromatography step.

Further, the present invention provides chromatography based protein purification processes which include fewer steps than conventional processes.

In one aspect according to the present invention, a method for reducing the burden of one or more chromatography columns is provided. In some embodiments, such a method comprises contacting a sample comprising a protein of interest and one or more impurities in a flow-through mode with one of: (i) a carbonaceous material; (ii) a combination of a carbonaceous material and CEX media; (iii) a combination of a carbonaceous material and AEX media; (iv) a combination of a carbonaceous material and mixed mode media; (v) a combination of a carbonaceous material and HIC media, and (vi) a combination of a carbonaceous material and CEX, AEX and mixed mode media, prior to contacting the sample with one or more chromatography columns containing affinity media. AEX media, CEX media, HIC media or mixed-mode media, thereby to reduce the burden of one or more chromatography columns.

In another aspect according to the claimed methods, a method of reducing the level of one or more impurities in a sample containing a protein of interest and the one or more impurities is provided, where the method comprises the steps of: (i) contacting a sample comprising a protein of interest and one or more impurities with one or more chromatography columns containing affinity media, AEX media, CEX media. HIC media or mixed-mode media, under conditions such that the protein of interest binds to the column; (ii) obtaining a first eluate of the sample; (iii) contacting the first eluate in flow-through mode with one of: (a) a carbonaceous material; and (b) a combination of a carbonaceous material and one or more of CEX media, AEX media, mixed mode media and HIC media; and (iv) obtaining a second eluate of the sample; where the second eluate comprises lower or reduced level of one or more impurities relative to the level of one or more impurities in the first eluate.

In yet another aspect, a method of reducing the level of one or more impurities in a sample comprising a protein of interest and one or more impurities is provided, the method comprising the steps of: (i) contacting a sample comprising a protein of interest and one or more impurities with a chromatography column containing affinity media; (ii) obtaining a first eluate of the sample; (iii) contacting the first eluate in flow-through mode with a carbonaceous material; (iv) obtaining a second eluate of the sample; (v) contacting the second eluate with an anion exchange chromatography media; and (vi) obtaining a third eluate of the sample, wherein the third eluate comprises lower or reduced level of one or more impurities relative to the level of one or more impurities when the first eluate is not contacted with the carbonaceous material.

In some embodiments, such a method includes a CEX bind and elute chromatography step after the affinity capture step and before contacting the sample with an anion exchange chromatography media, which in some embodiments is a membrane adsorber. In some embodiments, a method according to the claimed invention obviates the need for further chromatography steps, e.g., a bind and elute CEX chromatography step used after the affinity capture step. Exemplary commercially available anion exchange chromatography media are membrane adsorbers such as ChromaSorb™ (MILLIPORE CORPORATION, Billerica, Mass., USA), Mustang Q (PALL CORPORATION, Port Washington, N.Y., USA), Sartobind Q (SARTORIUS STEDIM, Germany), as well as bead media such as Q Sepharose FF (GE HEALTHCARE, Philadelphia, Pa., USA).

In some embodiments, methods according to the claimed invention employ non-column based chromatography steps.

In yet another aspect, a method of reducing the level of one or more impurities in a sample comprising a protein of interest is provided, the method comprising the steps of: (i) obtaining a protein phase comprising the protein of interest; (ii) reconstituting the protein phase comprising the protein of interest using a suitable buffer, thereby to obtain a reconstituted protein solution; (iii) contacting the reconstituted protein solution with a carbonaceous material in flow-through mode; (iv) obtaining a first eluate comprising the protein of interest; (v) contacting the first eluate with an anion exchange chromatography media; and (vi) obtaining a second eluate comprising the protein of interest, wherein the second eluate comprises a lower or reduced level of one or more impurities relative to the level of one or more impurities when the reconstituted protein solution from (iii) is not contacted with the carbonaceous material.

In some embodiments, such a method obviates the need for any bind and elute chromatography steps, e.g., a bind and elute affinity or CEX chromatography steps.

In some methods according to the present invention, the protein phase is obtained using one or more methods selected from the group consisting of precipitation, flocculation, crystallization, column chromatography, use of a soluble small molecule, use of a polymeric ligand, or use of a suspended chromatography media.

In some embodiments, combination of a carbonaceous material and one or more of AEX media, CEX media, HIC media and mixed media entails mixing the carbonaceous material with one or more of such media. In other embodiments, combination of a carbonaceous material and one or more of AEX media, CEX media. HIC media and mixed media entails using different materials in the combination in tandem.

In various embodiments according to the methods of the present invention, the affinity media is selected from Protein A or Protein G.

In some embodiments, the protein of interest is an antibody or an Fc region containing protein. In some embodiments, the antibody is a monoclonal antibody. In other embodiments, the antibody is a polyclonal antibody.

In some embodiments, the sample comprises a cell culture feed.

In some embodiments, the sample is a clarified cell culture feed.

In some embodiments, the clarified cell culture feed is obtained via depth filtration and/or centrifugation.

In some embodiments, the clarified cell culture is obtained via precipitation with a salt, an acid, a polymer, or a stimulus responsive polymer.

In various embodiments, the carbonaceous material used in the methods according to the claimed invention is activated carbon. In some embodiments, activated carbon comprises activated charcoal.

In some embodiments, the combination of a carbonaceous material and one or more of CEX media, AEX media, mixed mode media and HIC media comprises a mixture of activated carbon and one or more of CEX resin, AEX resin, mixed mode resin and HIC resin. In some embodiments, such a mixture is packed into a chromatography column. In other embodiments, the mixture is packed into a disc. In still other embodiments, the mixture is packed into a pod, cartridge or a capsule.

In some embodiments, activated carbon is packed into a chromatography column. In other embodiments, activated carbon is packed in a sealed disposable device such as Millistak+® Pod. In yet other embodiments, activated carbon is packed in a cartridge or a capsule.

In some embodiments, activated carbon is impregnated into a porous material, e.g. activated carbon is incorporated into porous fibrous media. The porous material may be contained within a column, a disc, a Millistak+® Pod, a cartridge or a capsule. In some embodiments, activated carbon is packed into a cellulose media.

In a particular embodiment, the AEX media is a membrane having a surface coating comprising one or more polymeric primary amines or copolymers thereof.

In some embodiments, a sample comprising a protein of interest and one or more impurities is contacted with activated carbon prior to subjecting the sample to an affinity capture step. In other embodiments, the sample is contacted with activated carbon after the affinity capture step.

In various methods according to the claimed invention, the loss in yield of the protein of interest using a process which employs activated carbon is less than 20% of the total protein amount. In other words, processes according to the claimed invention result in 80% or greater yield of protein of interest, where 100% is the total protein amount. In a further embodiment, the loss of yield of the protein of interest using a process which employs activated carbon is less than 10%. In other words, processes according to the claimed invention result in 90% or greater yield of protein of interest, where 100% is the total protein amount.

In a particular embodiment, activated carbon is used as part of a flow-through purification process step or unit operation in a method for purifying a target molecule (e.g., an Fc region containing protein or an antibody) from a sample (e.g., an eluate such as a Protein A eluate recovered from a bind and elute chromatography capture process step performed prior to the flow-through purification step). In such a flow-through purification process step or unit operation, the eluate from a bind and elute chromatography step (e.g., a Protein A affinity column) flows through activated carbon followed by an AEX media followed by a CEX media and followed by a virus filter, as depicted in FIG. 19. In some embodiments, a solution change (e.g., pH change) is performed between the AEX step and the CEX step, where the solution employs an in-line static mixer and/or a surge tank. In some embodiments, the flow-through purification process step or unit operation employing activated carbon, as described herein, is part of a continuous process for purifying a target molecule, where the flow-through purification step is in fluid communication with a process step upstream (e.g., a bind and elute chromatography capture step) and a process step downstream (e.g., a formulation step) of the flow-through purification process step, thereby enabling the liquid sample to flow through the process continuously.

In a particular embodiment, the entire flow-through process step or unit operation employs a single skid (i.e., a control/monitoring equipment).

DETAILED DESCRIPTION

Figure 1:
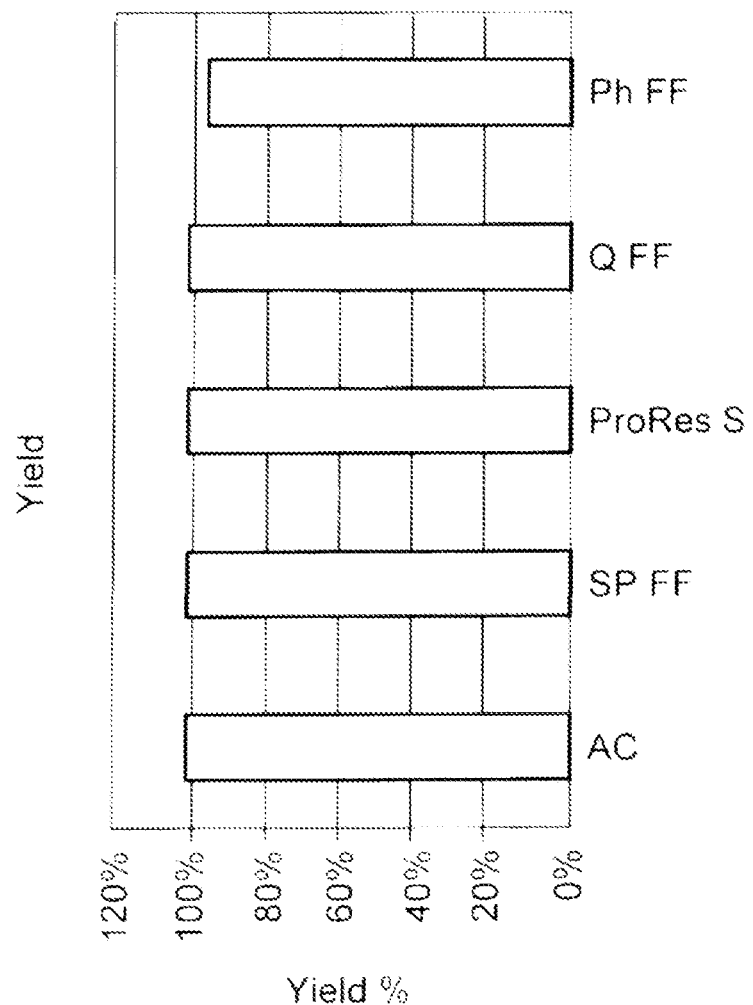
FIG. 1 depicts a bar graph demonstrating the results of an experiment to measure IgG yield in a flow-through eluate of a null CHO-S feed with added polyclonal IgG for each of the various commercially available adsorptive media that were evaluated, i.e., activated carbon (AC); an agarose cation exchange resin, SP Sepharose™ Fastflow (SPFF); a polymeric cation exchange resin, ProRes™-S; an agarose anion exchange resin, Q Sepharose™ (QFF); and an agarose HIC resin, Phenyl Sepharose™ 6 Fastflow (ph FF). As demonstrated in FIG. 1, except for the HIC resin which shows up to ~5% loss in IgG yield, all other media screened demonstrated no detectable yield loss.

The present invention provides novel and improved processes for purifying a protein of interest from a sample containing the protein of interest and one or more impurities.

Activated carbon has previously been used in water purification processes. In addition, activated carbon has been used to remove small molecule impurities, such as fatty acids and bilirubin, from serum album (see, e.g., Chen et al., J. Biol. Chem., 242: 173-181 (1967); Nakano et al., Anal Biochem., 129: 64-71 (1983); Nikolaev et al., Int. J. Art. Org., 14:179-185 (1991)). Activated carbon has also been used to remove pigments as well as host proteins, proteases, and ribonucleases during the purification of plant viruses (see, e.g., Price, Am. J. Botany, 33: 45-54 (1946); Corbett, Virology, 15:8-15 (1961); McLeana et al., Virology, 31: 585-591 (1967).

Accordingly, in general, activated carbon has been reported to non-specifically bind to molecules in solution (e.g., impurities in a water sample).

The present invention is based, at least in part, on the unexpected and surprising finding that activated carbon can selectively remove populations of proteinaceous impurities and DNA, thereby making it useful in the purification of proteins produced via recombinant expression in cells.

As demonstrated in the Examples herein, activated carbon can be used for selective removal of host cell protein (HCP) and DNA impurities during protein purification processes without significantly affecting the yield of the target protein. Further, as demonstrated in the Examples set forth herein, when activated carbon is used in a protein purification process in flow-through mode, either alone or in a mixture with one or more chromatography media of various types, it results in a significant reduction in the level of one or more impurities in the protein containing sample as well as reduces the burden of downstream chromatography columns. Further, in certain instances, activated carbon decreases the number of steps that may be used in a purification process, thereby reducing the overall operational costs and saving time. Further, as demonstrated in the Examples set forth herein, activated carbon can be used before or after a capture step, thereby to reduce the level of one or more impurities in a sample containing the protein of interest.

In some embodiments described herein, activated carbon is used in a flow-through purification step of an overall process for purifying a target molecule, where the overall process as well as the flow-through purification step are performed in a continuous manner.

In order that the present disclosure may be more readily understood, certain terms are first defined. Additional definitions are set forth throughout the detailed description.

I. Definitions

The term "carbonaceous material," as used herein, refers to any substance composed of carbon or containing carbon. In some embodiments, carbonaceous material used in the methods according to the claimed invention is active or activated carbon. In some embodiments, activated carbon comprises activated charcoal. In some embodiments, activated carbon is incorporated into a cellulose media.

The term "active carbon" or "activated carbon," as used interchangeably herein, refers to a carbonaceous material which has been subjected to a process to enhance its pore structure. Activated carbons are porous solids with very high surface areas. They can be derived from a variety of sources including coal, wood, coconut husk, nutshells, and peat. Activated carbon can be produced from these materials using physical activation involving heating under a controlled atmosphere or chemical activation using strong acids, bases, or oxidants. The activation processes produce a porous structure with high surface areas that give activated carbon high capacities for impurity removal. Activation processes can be modified to control the acidity of the surface.

Typical activation processes involve subjecting a carbon source, such as, resin wastes, coal, coal coke, petroleum coke, lignites, polymeric materials, and lignocellulosic materials including pulp and paper, residues from pulp production, wood (like wood chips, sawdust, and wood flour), nut shell (like almond shell and coconut shell), kernel, and fruit pits (like olive and cherry stones) to a thermal process (e.g., with an oxidizing gas) or a chemical process (e.g., with phosphoric acid or metal salts, such as zinc chloride). An exemplary chemical activation of wood-based carbon with phosphoric acid ($H_3PO_4$) is disclosed in U.S. Pat. No. Re. 31,093, which resulted in an improvement in the carbon's decolorizing and gas adsorbing abilities. Also, U.S. Pat. No. 5,162,286 teaches phosphoric acid activation of wood-based material which is particularly dense and which contains a relatively high (30%) lignin content, such as nut shell, fruit stone, and kernel. Phosphoric acid activation of lignocellulose material is also discussed in U.S. Pat. No. 5,204,310, as a step in preparing carbons of high activity and high density. The teachings of each of the patents listed in this paragraph are incorporated by reference herein in their entirety.

In contrast to most other adsorbing materials, activated carbon is believed to interact with molecules using relatively weak van der Waals or London dispersion forces. Typical commercial activated carbon products exhibit a surface area of at least 300 m$^2$/g, as measured by the nitrogen adsorption based Brunauer-Emmett-Teller ("BET") method, which is method well known in the art.

Although, active or activated carbon has been previously employed in processes for purifying liquids and gases, it has not been previously employed in processes for purifying a recombinantly expressed protein from one or more proteinaceous impurities.

The term "immunoglobulin," "Ig" or "IgG" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions". "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. Immunoglobulins or antibodies may also include multispecific antibodies (e.g., bispecific antibodies), and antibody fragments so long as they retain, or are modified to comprise, a ligand-specific binding domain. The term "fragment" or "functional fragment" of an antibody refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments. Exemplary fusion proteins include Fc fusion proteins.

In a particular embodiment, methods according to the claimed invention are used for purifying a fragment of an antibody which is an Fc-region containing fragment.

The term "Fc region" and "Fc region containing protein" means that the protein contains heavy and/or light chain constant regions or domains (CH and CL regions as defined previously) of an immunoglobulin. Proteins containing an "Fc region" can possess the effector functions of an immunoglobulin constant domain. An "Fc region" such as $CH_2$/$CH_3$ regions, can bind selectively to affinity ligands such as Protein A or functional variants thereof. In some embodiments, an Fc region containing protein specifically binds Protein A or a functional derivative, variant or fragment thereof. In other embodiments, an Fc region containing protein specifically binds Protein G or Protein L, or functional derivatives, variants or fragments thereof.

As discussed above, in some embodiments, a target protein is an Fc region containing protein, e.g., an immunoglobulin. In some embodiments, an Fc region containing protein is a recombinant protein which includes the Fc region of an immunoglobulin fused to another polypeptide or a fragment thereof.

Generally, an immunoglobulin or antibody is directed against an "antigen" of interest. Preferably, the antigen is a biologically important polypeptide and administration of the antibody to a mammal suffering from a disease or disorder can result in a therapeutic benefit in that mammal.

The term "monoclonal antibody" or "Mab," as used interchangeably herein, refers to an antibody obtained from a population of substantially homogeneous antibodies, i.e., the individual antibodies in the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). "Monoclonal antibodies" may also be isolated from phage antibody libraries using the techniques described in Clackson et al., Nature 352:624-628 (1991) and Marks et al., J. Mol. Biol. 222:581-597 (1991).

Monoclonal antibodies may further include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (2) and 89-97 (13) in the light chain variable domain and 31-35 (H1), 50-65 (H2) and 95-102 (H3) in the heavy chain variable domain; Kabat et al., Sequences of Proteins of Immunological Interest, $5^{th}$ Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody may comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

The terms "polynucleotide" and "nucleic acid molecule," used interchangeably herein, refer to polymeric forms of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically or biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de now using a DNA polymerase with an appropriate primer. A nucleic acid molecule can take many different forms, e.g., a gene or gene fragment, one or more exons, one or more introns, mRNA, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T. C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

The term "solution," "composition" or "sample," as used herein, refers to a mixture of a protein of interest or target protein (e.g., an Fc region containing protein such as an antibody) and one or more impurities. In some embodiments, the sample is subjected to a clarification step prior to being subjected to the methods according to the claimed invention. In some embodiments, the sample comprises cell culture feed, for example, feed from a mammalian cell culture (e.g., CHO cells). However, samples also encompass non-mammalian expression systems used for producing a protein of interest.

The term "non-mammalian expression systems" as used herein refers to all host cells or organisms employed to generate therapeutic proteins, where the host cells or organisms are of non-mammalian origin. Non-limiting examples of non-mammalian expression systems are *E. coli* and *Pichia pastoris*.

The term "UV active species" as used herein, refers to the composition of the flow-through fraction of a clarified cell culture following subjecting the culture to a Protein A analytical column, as monitored by a UV spectrophotometer. In some embodiments, the UV spectrophotometer monitors the fraction at 280 nm. This fraction generally consists of impurities such as, dyes (such as pH indicators), host cell proteins, DNA, and other cell culture media components that need to be removed from the fraction, which also contains the protein of interest (e.g., an antibody). The flow-through impurity peak is integrated manually or by a preset algorithm and is used to quantity the total impurity level.

As used herein, the term "polypeptide" refers generally to peptides and proteins having more than about ten amino acids. The terms "protein of interest" and "target protein," as used interchangeably herein, refer to a protein or polypeptide, including but not limited to, an Fc region containing protein such as an antibody that is to be purified by a method of the invention, from one or more impurities.

Exemplary polypeptides include, e.g., renin; a growth hormone, including human growth hormone and bovine growth hormone; growth hormone releasing factor; parathyroid hormone; thyroid stimulating hormone; lipoproteins; α-1-antitrypsin; insulin α-chain; insulin β-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-α and -β; enkephalinase; RANTES (regulated on activation normally T-cell expressed and secreted); human macrophage inflammatory protein (MIP-1-α); a serum albumin such as human serum albumin; Muellerian-inhibiting substance; relaxin α-chain; relaxin β-chain; prorelaxin; mouse gonadotropin-associated peptide; a microbial protein, such as β-lactamase; DNase; IgE; a cytotoxic T-lymphocyte associated antigen (CTLA) (e.g., CTLA-4); inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(1-3)-IGF-1 (brain IGF-I), insulin-like growth factor binding proteins (IGFBPs); CD proteins such as CD3, CD4, CD8, CD19, CD20, CD34, and CD40; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments and/or variants of any of the above-listed polypeptides. In addition, a protein or polypeptide of the invention is an antibody, fragment or variant thereof, that binds specifically to any of the above-listed polypeptides.

The terms "contaminant," "impurity," and "debris," as used interchangeably herein, refer to any foreign or objectionable molecule, including a biological macromolecule such as a DNA, an RNA, one or more host cell proteins (HCP), endotoxins, lipids and one or more additives which may be present in a sample containing the target protein that is being separated from one or more of the foreign or objectionable molecules using a process of the present invention. Additionally, such a contaminant may include any reagent which is used or generated in a step which may occur prior to the purification process, such as leached protein A in cases where a protein A affinity chromatography step is employed.

The terms "Chinese hamster ovary cell protein" and "CHOP" are used interchangeably to refer to a mixture of host cell proteins ("HCP") derived from a Chinese hamster ovary ("CHO") cell culture. The HCP or CHOP is generally present as an impurity in a cell culture medium or lysate (e.g., a harvested cell culture fluid ("HCCF")) comprising a protein of interest such as an antibody or immunoadhesin expressed in a CHO cell). The amount of CHOP present in a mixture comprising a protein of interest provides a measure of the degree of purity for the protein of interest. HCP or CHOP includes, but is not limited to, a protein of interest expressed by the host cell, such as a CHO host cell. Typically, the amount of CHOP in a protein mixture is expressed in parts per million relative to the amount of the protein of interest in the mixture. It is understood that where the host cell is another cell type, e.g., a mammalian cell besides CHO, an *E. coli*, a yeast, an insect cell, or a plant cell, HCP refers to the proteins, other than target protein, found in a lysate of the host cell.

The term "parts per million" or "ppm" are used interchangeably herein to refer to a measure of purity of a target protein purified by a method of the invention. The units ppm refer to the amount of HCP or CHOP in nanograms/milligrams of protein of interest or in milligrams/milliliter (i.e., CHOP ppm=(CHOP ng/ml)/(protein of interest mg/ml), where the proteins are in solution).

The terms "purifying," "separating," or "isolating," as used interchangeably herein, refer to increasing the degree of purity of a polypeptide or protein of interest or a target protein from a composition or sample comprising the protein of interest and one or more impurities. Typically, the degree of purity of the protein of interest is increased by removing (completely or partially) at least one impurity from the composition. A "purification step" may be part of an overall purification process resulting in a "homogeneous" composition or sample, which is used herein to refer to a composition or sample comprising less than 100 ppm HCP in a composition comprising the protein of interest, alternatively less than 90 ppm, less than 80 ppm, less than 70 ppm, less than 60 ppm, less than 50 ppm, less than 40 ppm, less than 30 ppm, less than 20 ppm, less than 10 ppm, less than 5 ppm, or less than 3 ppm of HCP.

The term "protein phase," as used herein, refers to the part of a sample where the concentration of the target protein has been substantially increased relative to the initial concentration of target protein in the sample. The concentration process may involve protein adsorption on a solid porous or non-porous support; protein adsorption at a liquid-air or liquid-gas interface; protein adsorption at the interface between two immiscible or partially miscible liquids; protein precipitation as a pure component or as a result of complex formation with one or more other molecules or polymers; or using protein crystallization.

The term "liquid phase" as used herein, refers to that part of a sample where the concentration of target protein has been substantially reduced compared to initial concentration of protein in the sample. The liquid phase can be created at the same time as the protein phase defined above.

The terms "flow-through process," "flow-through mode," and "flow-through chromatography," as used interchangeably herein, refer to a product separation technique in which at least one product in a sample is intended to flow through a chromatographic resin or media, while at least one potential component binds to the chromatographic resin or media.

The sample intended to flow through is generally referred to as the "mobile phase." The "flow-through mode" is generally an isocratic operation (i.e., a chromatography process during which the composition of the mobile phase is not changed). The media used for flow-through is usually pre-equilibrated with the same buffer solution that contains the target protein molecule. After purification, the media can be flushed with additional quantity of the same buffer to increase the product recovery. In some embodiments, the mobile phase of the "flow-through mode" is a cell culture feed containing the product of interest. In some instances, the pH or conductivity of the feed is adjusted in order to maximize impurity removal using the flow-through process.

In some embodiments according to the claimed methods and as described in the Examples set forth herein, the methods employ an anion exchange step which is performed in a flow-through mode.

The terms "bind and elute mode" and "bind and elute process," as used interchangeably herein, refer to a product separation technique in which at least one product contained in a sample binds to a chromatographic resin or media and is subsequently eluted.

The term "chromatography" refers to any kind of technique which separates an analyte of interest (e.g., an Fc region containing protein such as an immunoglobulin) from other molecules present in a mixture where the analyte of interest is separated from other molecules as a result of differences in rates at which the individual molecules of the mixture migrate through a stationary medium under the influence of a moving phase, or in bind and elute processes.

The term "chromatography resin" or "chromatography media" are used interchangeably herein and refer to any kind of porous or non-porous solid phase which separates an analyte of interest (e.g., an Fc region containing protein such as an immunoglobulin) from other molecules present in a mixture. Usually, the analyte of interest is separated from other molecules as a result of differences in rates at which the individual molecules of the mixture migrate through a stationary solid phase under the influence of a moving phase, or in bind and elute processes. Non-limiting examples include resins with cationic, anionic. HIC, or mixed mode surface modifications; membranes with cationic, anionic, HIC, or mixed mode surface modifications, woven or non-woven fibers with cationic, anionic, HIC, or mixed mode surface modifications; and monoliths with cationic, anionic, HIC, or mixed mode surface modifications.

The term "affinity separation," or "affinity purification," as used herein, refers to any purification or assaying technique which involves the contacting a sample containing a target analyte (e.g., an Fc region containing protein such as an immunoglobulin) with an affinity media (e.g., a solid support carrying on it an affinity ligand known to bind the analyte such as, for example, e.g., Protein A or a variant thereof) known to bind the target analyte.

The terms "affinity chromatography" and "protein affinity chromatography," as used interchangeably herein, refer to a protein separation technique in which a target protein (e.g., an Fc region containing protein of interest or an antibody) is specifically bound to a ligand which is specific for the target protein. In some embodiments, such a ligand is Protein A or Protein G or a functional variant thereof, which is covalently attached to a chromatographic solid phase material and is accessible to the target protein in solution as the solution contacts the chromatographic solid phase material. The target protein generally retains its specific binding affinity for the ligand during the chromatographic steps, while other solutes and/or proteins in the mixture do not bind appreciably or specifically to the ligand. Binding of the target protein to the immobilized ligand allows contaminating proteins or protein impurities to be passed through the chromatographic medium while the target protein remains specifically bound to the immobilized ligand on the solid phase material. The specifically bound target protein is then removed in active form from the immobilized ligand under suitable conditions (e.g., low pH, high pH, high salt, competing ligand etc.), and passed through the chromatographic column with the elution buffer, free of the contaminating proteins or protein impurities that were earlier allowed to pass through the column. Any component can be used as a ligand for purifying its respective specific binding protein, e.g. antibody. However, in various methods according to the present invention, Protein A is used as a ligand for an Fc region containing target protein or an antibody. The conditions for elution from the ligand (e.g., Protein A) of the target protein (e.g., an Fc region containing protein) can be readily determined by one of ordinary skill in the art. In some embodiments, Protein G or a functional variant may be used as a ligand. In some embodiments, a ligand such as Protein A is used at a pH range of 5-9 for binding to an Fc region containing protein, washing or re-equilibrating the ligand/target protein conjugate, followed by elution with a buffer having pH about or below 4.

Although, affinity chromatography is specific for binding the protein of interest, affinity chromatography employing use of ligands such as Protein A and Protein G tends to be quite expensive and rapid fouling of the chromatography columns by non-specific materials (e.g., one or more impurities) poses a huge problem in the industry. The methods according to the present invention provide a solution to this problem by use of materials (e.g., activated carbon) which reduce the burden of chromatography columns by removing one or more of such non-specific materials from the sample, thereby decreasing the overall cost as well as increasing the lifespan of the columns. Further, some of the methods according to the claimed invention result in the use of fewer chromatography steps following the affinity chromatography step, thereby increasing the efficiency of the overall process.

In a multi-step purification of recombinantly-produced proteins, it is usually beneficial to isolate the target protein from a diverse array of soluble impurities present in the cell culture fluid early in the process. This isolation can be achieved either by chromatographic capture or by non-chromatographic isolation of target protein.

A chromatographic "capture" step, as used herein, consists of binding target protein to a chromatography media positioned just downstream of the harvested feedstock produced either by a bacterial fermentation or by cell culture expression. Typically, the harvested feedstock is clarified, however capture can be accomplished from unclarified feedstock as well. The primary function of this step is to bind the target protein from solution using the smallest amount of resin possible, while allowing the impurities to flow through. The target protein is then eluted into a significantly smaller volume of buffer for further downstream processing. The chromatography media is selected which has the best combination of dynamic binding capacity, mass recovery, and retention of the target's biological activity. For antibodies containing Fc binding region, the use of an affinity chromatography media, such as those based on Protein A or Protein G, is common.

The chromatography media used for capture is chosen from the group comprising porous resin, membrane, monolith, woven or non-woven porous materials.

Non-chromatographic isolation of the target protein can be accomplished by one or more of the following steps: protein adsorption on a solid porous or non-porous support; protein adsorption at a liquid-air or liquid-gas interface; protein adsorption at the interface between two immiscible or partially miscible liquids; protein precipitation as a pure component or as a result of complex formation with one or more other molecules or polymers; or by using protein crystallization.

The term "ion-exchange" and "ion-exchange chromatography" refers to the chromatographic process in which a solute or analyte of interest (e.g., an Fc region containing target protein) in a mixture interacts with a charged compound linked by, e.g., covalent attachment, to a solid phase ion exchange material such that the solute or analyte of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest. "Ion-exchange chromatography" specifically includes cation exchange, anion exchange, and mixed mode ion exchange chromatography. For example, cation exchange chromatography can bind the target molecule (e.g., an Fc region containing target protein) followed by elution (cation exchange bind and elution chromatography or "CIEX") or can predominately bind the impurities while the target molecule "flows through" the column (cation exchange flow through chromatography FT-CIEX). Anion exchange chromatography can bind the target molecule (e.g., an Fc region containing target protein) followed by elution or can predominately bind the impurities while the target molecule "flows through" the column. In some embodiments and as demonstrated in the Examples set forth herein, the anion exchange chromatography step is performed in a flow through mode. In a particular embodiment, the anion exchange chromatography step employs the use of a porous sorptive media comprising a porous substrate and a porous coating on the substrate, where the coating comprising one or more polymeric primary amines or copolymers thereof.

The term "mixed-mode chromatography" or "multi-modal chromatography," as used herein, refers to a process employing a chromatography stationary phase that carries at least two distinct types of functional groups, each capable of interacting with a molecule of interest. An example of mixed mode chromatography media is Capto™ Adhere (GE Healthcare), which is an AEX mixed mode resin. Mixed-mode chromatography generally employs a ligand with more than one mode of interaction with a target protein and/or impurities. The ligand typically includes at least two different but co-operative sites which interact with the substance to be bound. For example, one of these sites may have a charge-charge type interaction with the substance of interest, whereas the other site may have an electron acceptor-donor type interaction and/or hydrophobic and/or hydrophilic interactions with the substance of interest. Electron donor-acceptor interaction types include hydrogen-bonding, π-π, cation-π, charge transfer, dipole-dipole and induced dipole interactions. Generally, based on the differences of the sum of interactions, a target protein and one or more impurities may be separated under a range of conditions.

The term "hydrophobic interaction chromatography" or "HIC," as used herein, refers to a process for separating molecules based on their hydrophobicity, i.e., their ability to adsorb to hydrophobic surfaces from aqueous solutions. HIC is usually differentiated from the Reverse Phase (RP) chromatography by specially designed HIC resins that typically have a lower hydrophobicity, or density of hydrophobic ligands compared to RP resins.

HIC chromatography typically relies on the differences in hydrophobic groups on the surface of solute molecules. These hydrophobic groups tend to bind to hydrophobic groups on the surface of an insoluble matrix. Because HIC employs a more polar, less denaturing environment than reversed phase liquid chromatography, it is becoming increasing popular for protein purification, often in combination with ion exchange or gel filtration chromatography.

The terms "ion exchange resin," "ion exchange media," and "ion exchange material" refer to a solid phase that is negatively charged (i.e. a cation exchange resin) or positively charged (i.e. an anion exchange resin). The charge may be provided by attaching one or more charged ligands to the solid phase, e.g. by covalent linking or non-covalent coating or adsorption. Alternatively, or in addition, the charge may be an inherent property of the solid phase.

The terms "CEX," "cation exchange media," "cation exchange resin" and "cation exchange material," as used herein, refer to a solid phase which is negatively charged, and which thus has free cations for exchange with cations in an aqueous solution passed over or through the solid phase. A negatively charged ligand attached to the solid phase to form the cation exchange resin may, e.g., be a carboxylate or sulfonate. Commercially available cation exchange resins include carboxy-methyl-cellulose, sulphopropyl (SP) immobilized on agarose (e.g., SP-SEPHAROSE FAST FLOW™ or SP-SEPHAROSE HIGH PERFORMANCE™, from Pharmacia) and sulphonyl immobilized on agarose (e.g. S-SEPHAROSE FAST FLOW™ from Pharmacia).

The terms "mixed mode media," "mixed mode resin" and "mixed mode ion exchange resin." as used herein, refer to a solid phase which is covalently modified with cationic, anionic, and hydrophobic moieties. A commercially available mixed mode ion exchange resin is BAKERBOND ABX™ (J. T. Baker, Phillipsburg, N.J.) containing weak cation exchange groups, a low concentration of anion exchange groups, and hydrophobic ligands attached to a silica gel solid phase support matrix.

The term "HIC media" or "HIC resin" or "HIC material." as used herein, refers to a chromatography material used for HIC separation. HIC media is usually derived from porous chromatography resin modified with hydrophobic ligands, such as short aliphatic or aromatic groups. Examples of HIC media include Butyl Sepharose FF and Phenyl Sepharose FF, both commercially available from GE Healthcare. Additional examples of commercial HIC resins include Fractogel® Phenyl and Fractogel® Propyl (MERCK KGA, Darmstadt, Germany), Butyl Sepharose® and Phenyl Sepharose® (GE HEALTHCARE).

The terms "AEX," "anion exchange media," "anion exchange resin" and "anion exchange material," as used herein, refer to a solid phase which is positively charged, e.g. having one or more positively charged ligands, such as primary, secondary, tertiary, or quaternary amino groups, attached thereto. Commercially available anion exchange resins include DEAE cellulose, QAE SEPHADEX™ and FAST Q SEPHAROSE™ (PHARMACIA).

The terms "Protein A" and "ProA" are used interchangeably herein and encompasses Protein A recovered from a native source thereof. Protein A produced synthetically (e.g., by peptide synthesis or by recombinant techniques), and variants thereof which retain the ability to bind proteins which have a $CH_2/CH_3$ region, such as an Fc region. Protein A can be purchased commercially from Repligen, GE Healthcare and Lonza. Protein A is generally immobilized on a solid phase support material. The term "ProA" also refers to an affinity chromatography resin or column containing chromatographic solid support matrix to which is covalently attached Protein A.

A functional derivative, fragment or variant of Protein A used in the methods according to the present invention may be characterized by a binding constant of at least $K=10^{-8}$ M, and preferably $K=10^{-9}$ M, for the Fc region of mouse IgG2a or human IgG1. An interaction compliant with such value for the binding constant is termed "high affinity binding" in the present context. Preferably, such functional derivative or variant of Protein A comprises at least part of a functional IgG binding domain of wild-type Protein A, selected from the natural domains E, D, A, B, C or engineered mutants thereof which have retained IgG binding functionality.

A "contaminant Protein A" according to the present invention is any type of functional, IgG binding offspring of a Protein A or a functional derivative thereof as defined above which is obtained upon eluting bound antibody from a Protein A affinity chromatography column. Such contaminant Protein A species may result e.g. from hydrolysis of peptide bonds which is very likely to occur by means of enzyme action in particular in industrial manufacturing. Protein A chromatography is applied as an early step in downstream processing when the crudely purified, fresh product solution still harbors considerable protease activity. Dying cells in the cell culture broth or cells disrupted in initial centrifugation or filtration steps are likely to have set free proteases; for regulatory purposes, supplementation of the cell culture broth with protease inhibitors prior or in the course of downstream processing is usually not accomplished, in contrast to biochemical research practice. Examples are Phenyl-methyl-sulfonyl-chloride (PMSF) or e-caproic acid. Such chemical agents are undesirable as additives in the production of biopharmaceuticals. It is further possible that recombinant functional derivatives or fragments of Protein A are less protease resistant than wild-type Protein A, depending on the tertiary structure of the protein fold. Amino acid segments linking individual IgG binding domains might be exposed once the total number of binding domains is reduced. Interdomain contacts may possible contribute to the stability of domain folding. It might also be that binding of antibody by Protein A or said functional derivatives thereof influences or facilitates susceptibility to protease action, due to conformational changes induced upon binding of the antibody.

"Binding" a molecule to a chromatography resin is meant exposing the molecule to chromatography resin under appropriate conditions (pH/conductivity) such that the molecule is reversibly immobilized in or on the chromatography resin by virtue of ligand-protein interactions. Non-limiting examples include ionic interactions between the molecule and a charged group or charged groups of the ion exchange material and a biospecific interaction between Protein A and an immunoglobulin.

The term "wash buffer" or "equilibration buffer" are used interchangeably herein, refers to a buffer used to wash or re-equilibrate the chromatography resin prior to eluting the polypeptide molecule of interest. In some cases, the wash buffer and loading buffer may be the same. "Washing" a chromatography media is meant to encompass passing an appropriate buffer through or over the media.

An "elution buffer" is used to elute the target protein from the solid phase. The conductivity and/or pH of the elution buffer is/are usually such that the target protein is eluted from the chromatography resin.

To "elute" a molecule (e.g., a polypeptide of interest or an impurity) from chromatography resin is meant to remove the molecule therefrom by altering the solution conditions such that buffer competes with the molecule of interest for binding to the chromatography resin. A non-limiting example is to elute a molecule from an ion exchange resin by altering the ionic strength of the buffer surrounding the ion exchange material such that the buffer competes with the molecule for the charged sites on the ion exchange material.

The term "eluate," as used herein, refers to a solution containing a molecule of interest obtained via elution as well as the flow-through fraction containing target protein of interest obtained as a result of flow-through purification. In some embodiments, the term "eluate" refers to the elution pool from a bind and elute chromatography step (e.g., a Protein A affinity chromatography step). In some embodiments, the eluate from a Protein A affinity chromatography step flows into a flow-through purification process which employs activated carbon, with or without an intervening virus inactivation step.

The term "solid phase" or "porous substrate" or "base matrix" refers to a non-aqueous material to which one or more charged ligands can adhere. The solid phase may be a purification column, a discontinuous phase of discrete particles that is porous or non-porous, a membrane, a woven or non-woven fibers, a monolith or a filter etc. Examples of materials for forming the solid phase include polysaccharides (such as agarose and cellulose); and other mechanically stable matrices such as silica (e.g. controlled pore glass), poly(styrenedivinyl)benzene, polyacrylamide, polyvinyl ether, nylon, high molecular weight polyethylene (HDPE), polyethersulfone, ceramic, and derivatives of any of the above.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). In some steps of the methods of the claimed invention, a buffer has a pH in the range from 2.0 to 4.0, or from 2.8 to 3.8. In other steps of the claimed invention, a buffer has a pH in the range of 5.0 to 9.0. In other steps of the claimed invention, a buffer has a pH in the range of 4.0 to 6.5. In yet other steps of the methods of the claimed invention, a buffer has a pH lower than 4.0. Non-limiting examples of buffers that will control the pH in this range include MES, MOPS, MOPSO, Tris, HEPES, phosphate, acetate, citrate, succinate, and ammonium buffers, as well as combinations of these.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSiemens per centimeter (mS/cm or mS), and can be measured using a commercially available conductivity meter (e.g., sold by Orion). The conductivity of a solution may be altered by changing the concentration of ions therein. For example, the concentration of a buffering agent and/or concentration of a salt (e.g. NaCl or KCl) in the solution may be altered in order to achieve the desired conductivity. Preferably, the salt concentration of the various buffers is modified to achieve the desired conductivity as in the Examples below.

The "pI" or "isoelectric point" of a polypeptide refer to the pH at which the polypeptide's positive charge balances its negative charge. pI can be calculated from the net charge of the amino acid residues or sialic acid residues of attached carbohydrates of the polypeptide or can be determined by isoelectric focusing.

As used herein, "filtrate" refers to that portion of a sample that passes through a media.

As used herein, "retentate" refers to that portion of a sample that is substantially retained by the media.

The term "clarification" as used herein, refers to a process for reducing turbidity, as measured in NTU, of a protein-containing solution, by removing suspended particles. Clarification can be achieved by a variety of means, including batch and continuous centrifugation, depth filtration, normal and tangential flow filtration, and precipitation, including flocculation with small molecule and polymeric species, or any combinations of methods thereof.

The phrase "reducing the burden of chromatography column" refers to a treatment or processing of a protein containing sample, which treatment or processing results in decreasing the fouling of a chromatography column onto which the protein sample is subsequently loaded. In a typical chromatography experiment, there could be non-eluting substances or impurities left behind on the stationary phase, thereby resulting in fouling of a chromatography column. This problem is further intensified during scale up, where the degree of column fouling is greater due to greater level of impurities being present. Fouling of columns also results in significantly diminishing the life span of the columns, which are usually quite expensive. The methods according to the present invention provide improved methods for significantly reducing the burden of chromatography columns, thereby increasing the life span of the columns as well resulting in greater yield of protein. The methods according to the present invention result in removal of significant amounts of impurities before loading the sample onto a chromatography column, thereby reducing the burden of the column. Typical impurities include host cell protein. DNA, fatty acid (from cell debris), dye molecule, defoaming agent, etc.

The term "process step" or "unit operation," as used interchangeably herein, refers to the use of one or more methods or devices to achieve a certain result in a purification process. Examples of process steps or unit operations which may be employed in the processes and systems described herein include, but are not limited to clarification, bind and elute chromatography capture, virus inactivation, flow-through purification and formulation. It is understood that each of the process steps or unit operations may employ more than one step or method or device to achieve the intended result of that process step or unit operation. For example, in some embodiments, the flow-through purification step, as described herein, may employ more than one step or method or device to achieve that process step or unit operation, where at least one such step involves activated carbon. In some embodiments, one or more devices which are used to perform a process step or unit operation are single use or disposable and can be removed and/or replaced without having to replace any other devices in the process or even having to stop a process run.

As used herein, the term "pool tank" refers to any container, vessel, reservoir, tank or bag, which is generally used between process steps and has a size/volume to enable collection of the entire volume of output from a process step. Pool tanks may be used for holding or storing or manipulating solution conditions of the entire volume of output from a process step. In some embodiments, the processes and described herein obviate the need to use one or more pool tanks.

The term "surge tank" as used herein refers to any container or vessel or bag, which is used between process steps or within a process step (e.g., when a single process step comprises more than one step); where the output from one step flows through the surge tank onto the next step. Accordingly, a surge tank is different from a pool tank, in that it is not intended to hold or collect the entire volume of output from a step; but instead enables continuous flow of output from one step to the next. In some embodiments, the volume of a surge tank used between two process steps or within a process step in a process or system described herein, is no more than 25% of the entire volume of the output from the process step. In another embodiment, the volume of a surge tank is no more than 10% of the entire volume of the output from a process step. In some other embodiments, the volume of a surge tank is less than 35%, or less than 30%, or less than 25%, or less than 20%, or less than 15%, or less than 10% of the entire volume of a cell culture in a bioreactor, which constitutes the starting material from which a target molecule is to be purified. In some embodiments, a surge tank is employed during a flow-through purification process step which uses activated carbon followed by AEX chromatography followed by CEX chromatography followed by virus filtration, where the surge tank is used to perform solution change after the AEX chromatography step.

The term "continuous process," as used herein, refers to a process for purifying a target molecule, which includes two or more process steps (or unit operations), such that the output from one process step flows directly into the next process step in the process, without interruption, and where two or more process steps can be performed concurrently for at least a portion of their duration. In other words, a continuous process obviates the need for completing a process step before performing the next process step in the purification process. The term "continuous process" also applies to steps within a process step, in which case, during the performance of a process step including multiple steps, the sample flows continuously through the various steps that are necessary to perform the process step. Accordingly, in some embodiments, a flow-through purification step employing activated carbon is performed in a continuous manner, where the eluate from a bind and elute chromatography step (e.g., Protein A chromatography capture step), which precedes the flow-through purification step, flows into an activated carbon (packed in cellulose media) step followed by an AEX chromatography step followed by a CEX chromatography step and followed by a virus filtration step.

The term "static mixer" refers to a device for mixing two fluid materials, typically liquids. The device generally consists of mixer elements (also referred to as non-moving elements) contained in a cylindrical (tube) housing. As the streams move through the static mixer, the non-moving elements continuously blend the materials. Complete mixing depends on many variables including the properties of the fluids, inner diameter of the tube, number of mixer elements and their design etc. In some embodiments described herein, one or more static mixers are used in the processes described herein, e.g., between an AEX chromatography step and a CEX chromatography step.

This invention is further illustrated by the following examples which should not be construed as limiting. The contents of all references, patents and published patent applications cited throughout this application, as well as the Figures, are incorporated herein by reference.

II. Exemplary Carbonaceous Materials for Use in the Claimed Methods

In methods according to the present invention, certain carbonaceous materials such as, activated carbon, are used in the purification of proteins. Activated carbon can be described as a porous solid with a very high surface area. In some embodiments, activated carbon comprises activated charcoal. Activated carbon can be derived from a variety of sources including, but not limited to, coal, wood, coconut husk, nutshells, and peat. Activated carbon can be produced from these materials by physical activation involving heat under a controlled atmosphere or by chemical activation using strong acids, bases, or oxidants. The activation processes produce a porous structure with a high surface area that gives activated carbon a greater capacity for impurity removal. Activation processes can be modified to control the acidity of the surface.

Activated carbon is available from a wide variety of commercial sources and comes in a number of grades and formats. Some of the commercial suppliers of activated carbon include companies such as MeadWestVaco Corp., Richmond, Va., USA; Norit Americas Inc., Marshall, Tex., USA; Calgon Carbon Corp., Pittsburgh, Pa., USA.

Two major formats of activated carbon are powdered and granular. Powdered activated carbon contains small and usually less than 1 mm diameter particles, and is most commonly used for purification of liquids. Granular activated carbon has a larger particle size and consequently a smaller surface area, so it is preferred for use in gas purification where the rate of diffusion is faster.

An important consideration for safety with use of activated carbon in consumer applications (such as water, food, beverage, and pharmaceutical purification) is reduction and control of extractable compounds. Activated carbon intended for drinking water and food contact applications is usually made in compliance with safety standard ANSI/NSF Standard 61 that covers all indirect additives to water. Also, ASTM standard test method D6385 describes determining acid extractable content in activated carbon by ashing and could be used to study and minimize the level of extractables from activated carbon.

A range of activated carbon types is available for various applications. For example, MeadWestVaco Corp. supplies at least twelve types of powdered activated carbon that vary by their capacity, surface acidity, pore accessibility to target molecules, and intended application. It is generally desirable to maximize the capacity of activated carbon for impurity removal.

In some embodiments described herein, activated carbon is incorporated in a cellulose media.

III. Conventional Flow-Through Purification Processes

Most conventional flow-through purification processes rely distinctly on different surface interactions between the target protein of interest and the impurity to be removed. For example, conventional AEX flow-through purification of monoclonal antibodies relies on the fact that isoelectric point of most antibodies is higher than other proteins and nucleic acids and is usually above 7. Thus, AEX flow-through purification processes are carried out at a pH that is lower than the pI of the antibody being purified in order to make sure that the stationary phase and the antibody have the same charge and thus the antibody flows through the media without significantly binding to the surface. On the other hand, many proteinaceous impurities nucleic acids, and endotoxins have a pI lower than an antibody, which is usually below 7, and accordingly, they bind to the surface of an AEX media.

Like most ion-exchange chromatography processes. AEX flow-through purification is generally sensitive to solution conductivity and is generally less effective at higher salinity. In a typical purification process of a monoclonal antibody, AEX flow-through purification, sometimes referred to as the "polishing step," follows one or more bind and elute column chromatography steps.

Two most commonly used process templates are shown below:

1) Protein A capture→CEX bind and elute purification and concentration→Dilution→AEX flow-through
2) Protein A capture→AEX flow-through→CEX bind and elute purification and concentration In addition to these commonly employed process templates, other purification schemes are sometimes employed, including CEX capture and the use of mixed-mode and inorganic bind and elute resins (such as Ceramic Hydroxyapatite, CHT). In general, the goal of flow-through purification is to remove trace levels of impurities, whereas the bulk of purification is done using bind and elute steps. However, a shift from using primarily bind and elute steps to a flow-through purification process can be a very cost-effective solution that saves time, reagents as well as operational costs. Accordingly, the processes described herein provide a viable solution to the conventional processes in that they are more cost-effective and reduce the overall manufacturing and operational costs.

In some embodiments described herein, improved flow-through purification processes are provided which enable flow-through purification to be performed in a continuous manner.

IV. Use of Carbonaceous Material in Purification Processes

As discussed above, the present invention provides novel and improved purification processes which employ activated carbon. Activated carbon can be added directly to a purification step and can subsequently be removed by sedimentation or filtration, or by passing solution or gas through a device containing activated carbon. Activated carbon can either be packed independently into a suitable device or it may be blended with other materials that enhance its mechanical, flow, or separation properties. For example, activated carbon can be incorporated into a wet-laid fibrous media containing cellulose, and then sealed inside a disposable device such as Millistak+® Pod CR available from Millipore Corporation, or Seitz® AKS Filter Media available from Pall Corporation, Port Washington, N.Y., USA. Another format of activated carbon is an activated carbon block, where activated carbon is incorporated into a porous monolith by pressing together with thermoplastic powder. Granular form of activated carbon can also be packed into columns, similar to chromatography media, or it may be packed into a suitable device. It is generally accepted that activated carbon media is used for decolorization, removal of small molecule impurities, etc. For example, there are several grades of activated carbon media available from Pall Corporation, that can be selected based on molecular weight of targeted impurities. Three molecular weight ranges are available: 200-400, 400-1,000, and 400-1,500 Daltons, the latter being the largest. However, none of the commercially available activated carbon media have been described for the selective removal of much larger impurities from biological samples, ranging from 2000 to 200,000 Daltons in molecular weight.

The present invention is based, at least in part, on the surprising discovery that activated carbon is capable of selectively binding undesirable impurities (e.g., HCPs and DNA), while at the same time showing negligible binding to a target protein.

This invention also recognizes the fact that, similar to all adsorptive material, the adsorptive capacity of activated carbon is not unlimited. For example, in the case of CHO-S feed, activated carbon has shown to effectively remove both HCP and DNA when these species were present at concentrations that were observed in representative feeds as shown in Example 1. However, addition of DNA to an unusually high level was found to suppress the HCP removal efficiency of activated carbon as shown in the Example 2.

Activated carbon can also be highly beneficial in removing potential components of cell culture media that may be present in the solution of target protein, both before and after target protein capture step. Typical components of cell culture media include surfactants (e.g., Pluronic® F68), insulin, antibiotics, methotrexate, and antifoam. Due to a risk that some of these components will be carried over into a purified target protein, it is advantageous to incorporate a step into a protein purification train that is capable of removing these components. Activated carbon may be used in a purification process to remove such components, as further evidenced by Examples herein.

The following are examples of protein purification processes that incorporate activated carbon as one or more intermediate steps, which is shown by underline in the following Table I below. It is understood that many variations of these processes can be used.

TABLE I

|  | Step 1 | Step 2 | Step 3 | Step 4 | Step 5 |
|---|---|---|---|---|---|
| Process A | Provide Clarified Cell Culture Fluid | Flow through activated carbon | Bind and elute with Affinity media | Bind and elute with CEX media | Flow through AEX media |
| Process B | Provide Clarified Cell Culture Fluid | Bind and elute with Affinity media | Flow through activated carbon | Bind and elute with CEX media | Flow through AEX media |

TABLE I-continued

| | Step 1 | Step 2 | Step 3 | Step 4 | Step 5 |
|---|---|---|---|---|---|
| Process C | Provide Clarified Cell Culture Fluid | Bind and elute with Affinity media | Bind and elute with CEX media | Flow through activated carbon | Flow through AEX media |
| Process D | Provide Clarified Cell Culture Fluid | Bind and elute with Affinity media | Bind and elute with CEX media | Flow through AEX media | Flow through activated carbon |
| Process E | Provide Clarified Cell Culture Fluid | Bind and elute with Affinity media | Flow through activated carbon | Flow through AEX media | |
| Process F | Provide Clarified Cell Culture Fluid | Bind and elute with CEX media | Flow through activated carbon | Flow through AEX media | |
| Process G | Provide Clarified Cell Culture Fluid | Bind and Elute with Affinity media | Flow through activated carbon | Flow through AEX media | Flow through CEX media |

In general, in the Table above, the step of Bind and Elute with Affinity media, and/or Bind and Elute with CEX media can be operated in any of three modes: (1) batch mode, where the media is loaded with target protein, loading is stopped, media is washed and eluted, and the pool is collected; (2) semi-continuous mode, where the loading is performed continuously, while the elution is intermittent (e.g., in case of continuous multicolumn chromatography); and (3) full continuous mode, where both loading and elution are performed continuously.

In some embodiments, one or more processes described in the Table above, a virus inactivation step may be performed after the bind and elute step and before subjecting the eluate to a flow-through purification step, as described herein.

It is understood that the processes described herein and in the Table above may further employ additional steps as well as steps for changing solution conditions in-line or via a surge tank. In some embodiments described herein, a process includes the following steps: clarification; bind and elute with Protein A affinity media; in-line virus inactivation; flow-through purification as follows: activated carbon followed by flow-through AEX media followed by a solution change using an in-line static mixer and/or surge tank, followed by flow-through CEX media followed by virus filtration; and formulation.

V. Assaying for Reduced Levels of One or More Impurities

The present invention provides processes for reducing the level of one or more impurities present in a sample containing a protein of interest. Typical impurities contained in a protein sample derived from a biological source include host cell proteins (HCP) and nucleic acids (DNA). When a host cell is Chinese Hamster Ovary (CHO), the HCP is commonly referred to as CHO HCP or CHOP. Immunological methods using antibodies to HCPs such as Western Blot and ELISA are conventionally used for detection of such impurities. Microtiter plate immunoenzymetric assays (ELISA) are also routinely employed in order to provide a high sensitivity of analysis. Such assays are simple to use, objective, and powerful tools for measuring the level of one or more impurities during purification processes.

Some of the ELISA kits for measuring HCP are commercially available from vendors such as, e.g., Cygnus Technologies of Southport, N.C., USA. Some of such kits are "generic" in the sense that they are intended to react with essentially all of the HCPs that could contaminate the product independent of the purification process that was used. In some embodiments, commercially available kits may be used for detecting the level of one or more impurities in a sample.

This invention is further illustrated by the following examples which should not be construed as limiting. The contents of all references, patents and published patent applications cited throughout this application, as well as the Figures, are incorporated herein by reference.

EXAMPLES

Example 1. Evaluation of Various Materials for Impurity Removal in Flow-Through Mode In this experiment, different materials were evaluated for their ability to remove impurities from a clarified CHO feed. Materials, shown in Table II, were tested for impurity removal in flow-through mode. Phosphate buffer saline (PBS, 10 mM phosphate, pH 7.4) was used as an equilibrium and wash buffer.

TABLE II

| Material | Acronym | Description | Vendor/Catalog |
|---|---|---|---|
| Activated carbon | AC | RGC 80 | MeadWestVado |
| SP sepharose FastFlow | SP FF | Agarose cation exchange chromatography (CIEX) resin | GE Healthcare |
| ProRes ™-S | ProRes ™-S | Polymeric cation exchange chromatography (CIEX) resin | Millipore Corporation |
| Q sepharose FastFlow | Q FF | Agarose anion exchange chromatography (AIEX) resin | GE Healthcare |
| Phenyl Sepharose FastFlow | Ph FF | Agarose hydrophobic interaction chromatography (HIC) resin | GE Healthcare |

Gravity flow-through (FT) test method was used to test resin impurity removal. One ml of each material listed in Table II (1 ml) was allowed to settle and packed into a 5 ml disposable chromatography column (Evergreen Scientific, LA, Calif.). The columns were equilibrated with 5 column volumes (CVs) of equilibrium buffer (PBS), loaded with 20 CVs of feed and washed with 5 CVs of wash buffer (PBS) again. The flow-through eluant fractions were collected. Untreated clarified null CHO-S feed with the addition of a polyclonal IgG (~2.6 mg/ml, SeraCare) was used.

Flow-through eluant and the corresponding feed were tested for IgG yield, UV active species (280 nm) removal, HCP removal and DNA removal. IgG yield was quantified on a Waters Alliance HPLC (Milford, Mass.) using Poros Protein A 2.1 mm×30 mm analytical column (LIFE TECHNOLOGIES, Palo Alto, Calif.) per vendor's instructions. UV active species at 280 nm was quantified using peak area of the non-retaining species that are shown as the flow through peak on the Protein A chromatogram. Host cell protein was detected using the CHO-CM HCP ELISA kit (CYGNUS TECHNOLOGIES, Southport, N.C.). DNA was detected using Quant-iT™ PicoGreen® dsDNA Reagent (LIFE TECHNOLOGIES. Foster City, Calif.). All assays were done according to manufactures protocols. The results are depicted in FIGS. 1-4.

As depicted in FIG. 1, except for HIC resin, which shows ~5% IgG yield loss, all other media screened, i.e., activated carbon, SPFF, ProRes™-S, and QFF demonstrated no detectable loss of yield.

Figure 2:
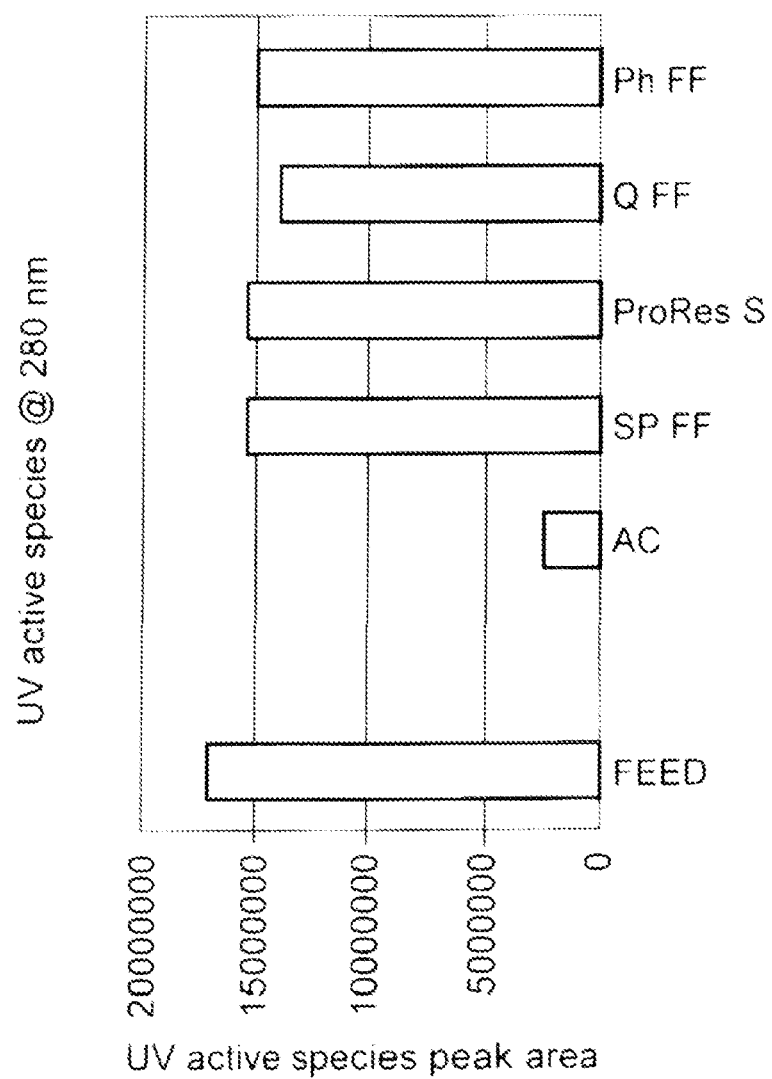
FIG. 2 depicts a bar graph demonstrating the results of an experiment to measure the amount of UV 280 nm active species in a flow-through eluate of a null CHO-S feed with added polyclonal IgG, for each of the various commercially available adsorptive media that were evaluated, i.e., an activated carbon, Nuchar® RGC, (AC), SPFF, ProRes™-S, QFF and ph FF as well as the untreated clarified feed. As demonstrated in FIG. 2, activated carbon significantly reduced the amount of colored species compared with the other adsorptive media.
Figure 3:
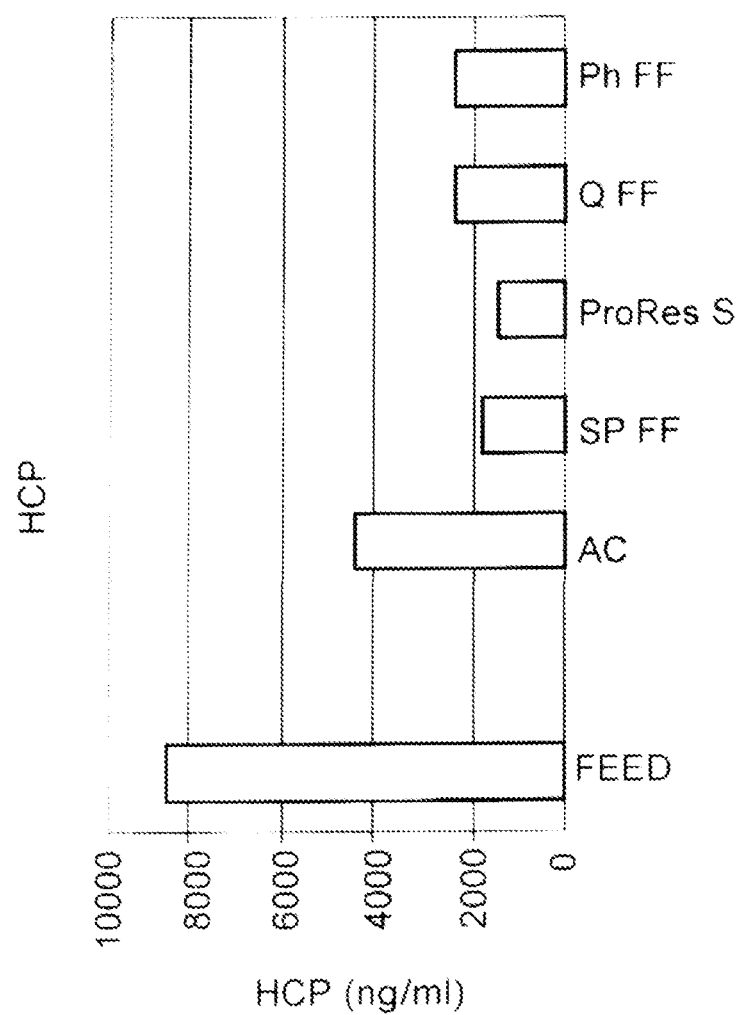
FIG. 3 depicts a bar graph demonstrating the results of an experiment to measure the concentration of host cell protein (HCP) in a flow-through eluate of a null CHO-S feed with added polyclonal IgG, for each of the commercially available adsorptive media listed above, as well as the untreated clarified feed. The HCP concentration was measured in ng/mL using a Cygnus CHO-CM HCP ELISA kit. As demonstrated in FIG. 3, all the media screened, including activated carbon, removed HCP to some extent. However, the cationic resins SPFF and ProRes™-S, removed HCP most effectively.
Figure 4:
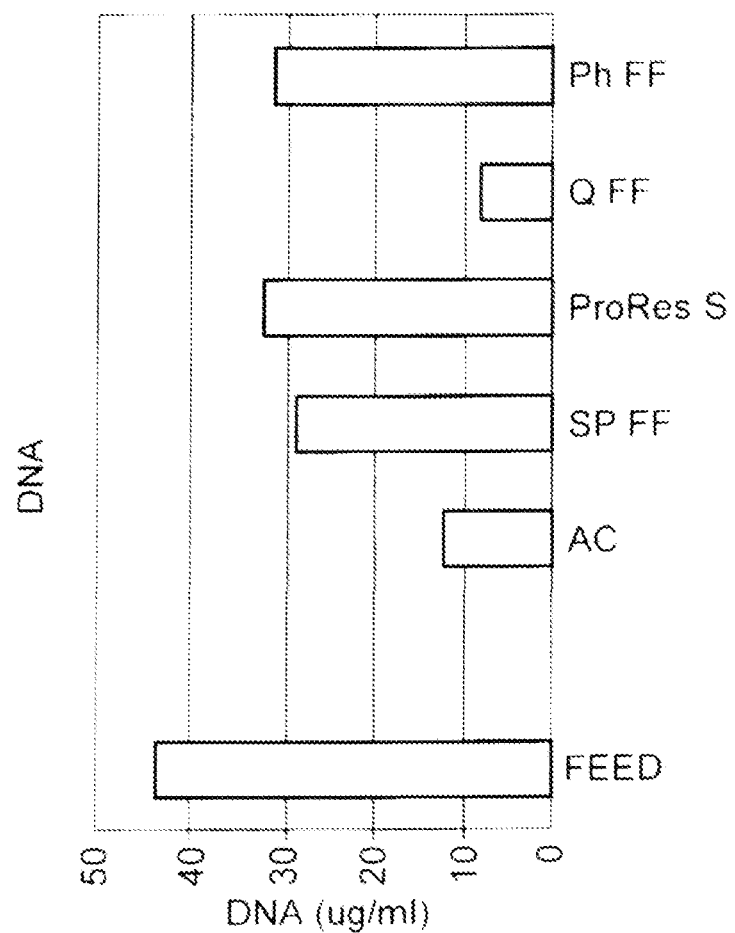
FIG. 4 depicts a bar graph demonstrating the results of an experiment to measure the DNA concentration in a flow-through eluate of a null CHO-S feed with added polyclonal IgG, for each of the media listed above, as well as the untreated clarified feed. DNA concentration (µg/mL) was measured using a PicoGreen assay. As demonstrated in FIG. 4, each of the media removes DNA to some extent. However, the anion exchange media removes DNA most effectively, followed by activated carbon.

Further, as depicted in FIGS. 2, 3 and 4, activated carbon resulted in a significant reduction in the levels of UV active species at 280 nm. This includes pH indicators, some population of HCP, DNA and some residual cell culture components. In the case where polyclonal IgG was used, this fraction also includes the IgG 3 population that Protein A does not bind. While all materials appeared to remove HCP to some degree, including activated carbon, the two materials with cation exchange functionality, Sepharose Fast-Flow and ProRes™-S, removed the most HCP. As for DNA removal, while it was not surprising to see significant DNA removal by anion exchange resin, Q FastFlow, it was unexpected to see that activated carbon removed DNA in similar capacity. All other material removed DNA to a lesser degree.

Data from this example demonstrates that activated carbon, as well as materials with cation exchange, anion exchange and hydrophobic interaction functional groups, can remove impurities (HCP, DNA and UV active species) to various degrees without significant yield loss in flow through mode from a CHO feed.

Example 2. Flow-Through Impurity Removal Capacity

In a representative experiment, the amount of impurities removed by different materials per unit volume was evaluated. The level of DNA in the CHO-S feed was increased through the addition of commercially available Herring Sperm DNA to understand the effect of adsorption competition between DNA and HCP. The materials that were evaluated for impurity removal are listed in Table III below.

TABLE III

| Material | Acronym | Description | Vendor/Catlog |
|---|---|---|---|
| Activated carbon | AC | activated carbon | MeadWestVaco RGC 80 |
| SP sepharose FastFlow | SP FF | cation exchange chromatography (CIEX) resin, agarose base matrix | GE Healthcare, Cat# 17-0729-01 |
| ProRes ™-S | ProRes ™-S | cation exchange chromatography (CIEX) resin, polymeric base matrix | Millipore Corporation |
| Q sepharose FastFlow | Q FF | Anion exchange chromatography (AIEX) resin, agarose base matrix | GE Healthcare, Cat# 17-0510-01 |

Each of the materials listed in Table III (1 ml) were packed into an Omnifit column (0.66 cm i.d.). Columns were equilibrated with 5 CVs PBS, loaded with 100 CV of null untreated clarified CHO-S feed with the addition of polyclonal IgG and Herring sperm DNA and washed with 20 column volumes PBS on a BioCad (APPLIED BIOSYSTEMS, Palo Alto, Calif.). The flow-through eluant fractions during loading step were collected at every 10 column volumes. Flow-through eluant fractions and the corresponding feeds were assayed for IgG yield. UV active species, HCP and DNA removal using the same methods as described in Example 1.

Figure 5:
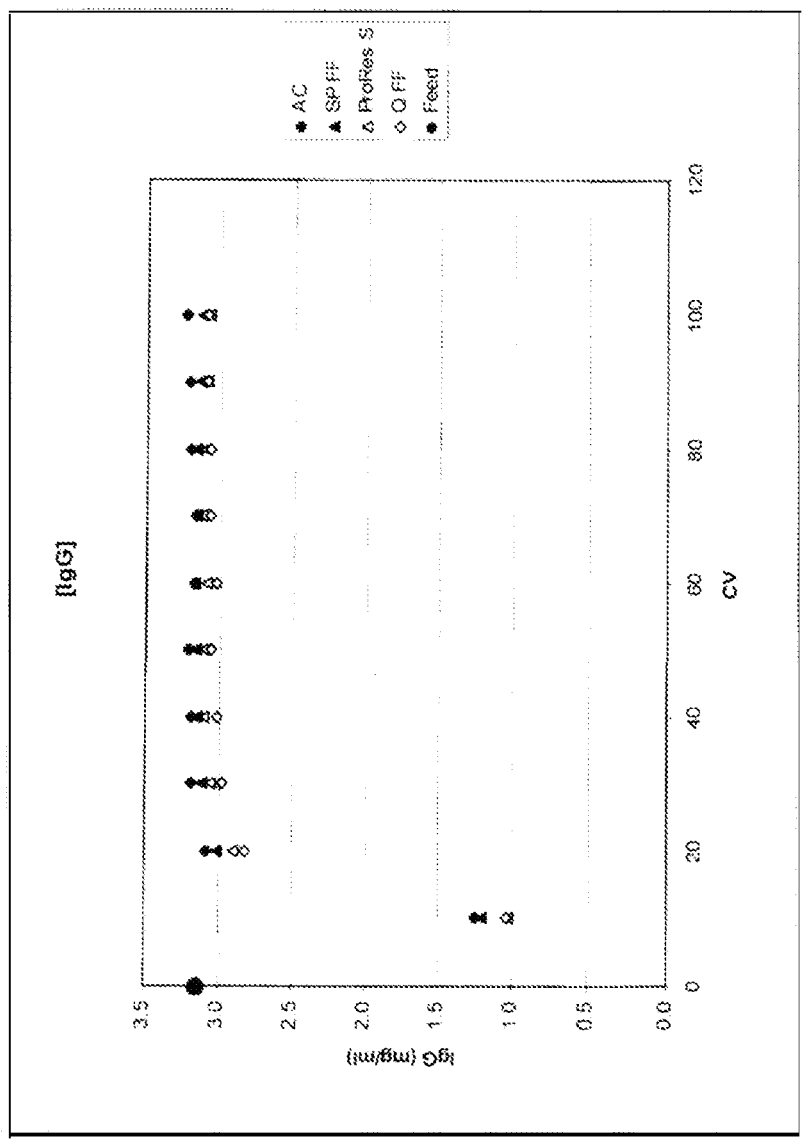
FIG. 5 depicts an x-y scatter plot demonstrating the results of an experiment to measure the concentration of IgG in a flow-through eluate of a null CHO-S feed with added polyclonal IgG and Herring sperm DNA, for each of the media evaluated listed above, at every 10 CV of feed loaded, up to 100 CV, including the untreated clarified feed. Column volume (CV) is shown on the x-axis and IgG concentration in mg/mL is shown on the y-axis. All of the media evaluated, including AC, SPFF, ProRes™-S and QFF, showed no significant loss of IgG up to a loading of 100 CV of untreated clarified feed.
Figure 6:
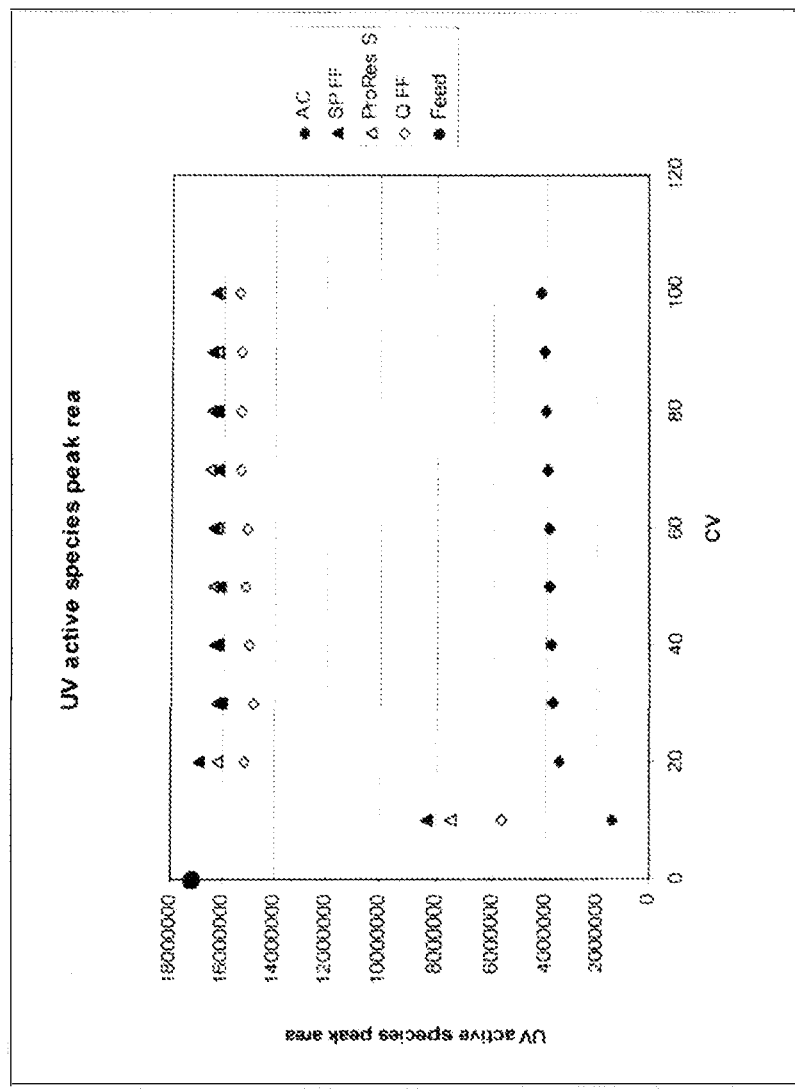
FIG. 6 depicts an x-y scatter plot demonstrating the results of an experiment to measure the UV active species peak area (corresponding to the quantity of UV active species) in a flow-through eluate of a null CHO-S feed added polyclonal IgG and Herring sperm DNA, for each of the media evaluated, at every 10 CV of feed loaded, up to 100 CV, including the untreated clarified feed. Column volume (CV) is shown on the x-axis and UV active species peak area in the flow-through of Protein A analytical column is shown on the y-axis. Of all the materials evaluated, AC removed more than 70% of the UV active species throughout the 100 CV; QFF removed about 10% of UV active species throughout the 100 CV; and the two cation exchange resins, SPFF and ProRes™-S removed minimal amount of UV active species.
Figure 7:
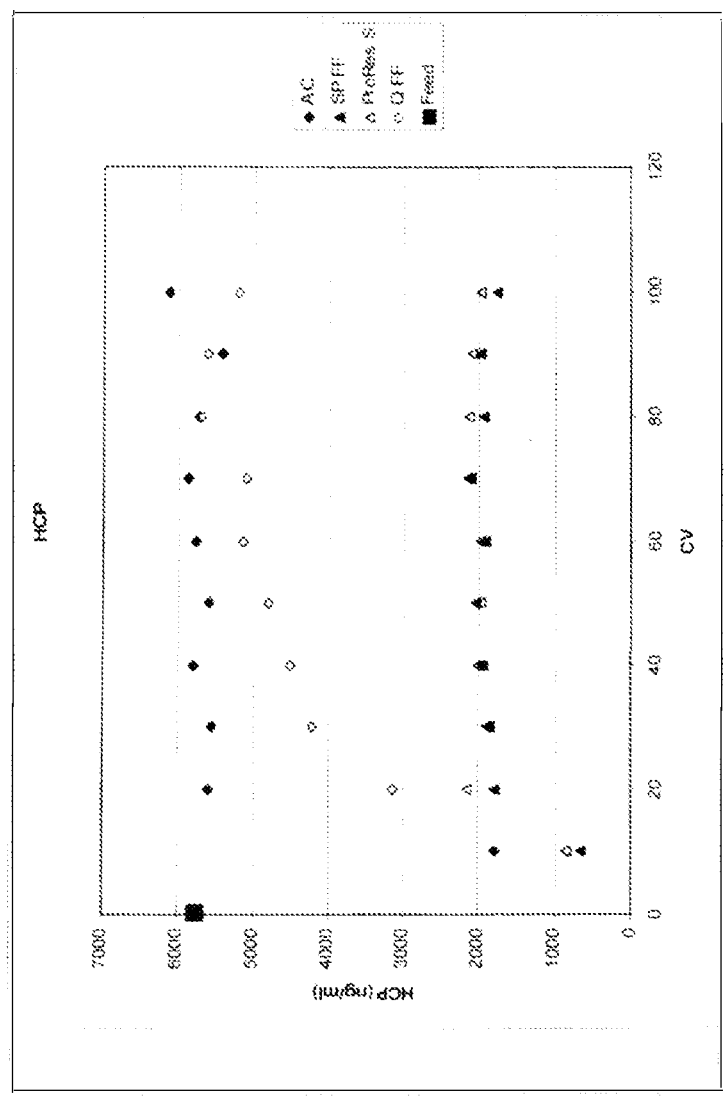
FIG. 7 depicts an x-y scatter plot demonstrating the results of an experiment to measure the host cell protein (HCP) concentration in a flow-through eluate of a null CHO-S feed with added polyclonal IgG and Herring sperm DNA, for each of the media evaluated and listed above, at every 10 CV of feed loaded up to 100 CV, including the untreated clarified feed. Column volume (CV) is shown on the x-axis and HCP concentration in ng/mL is shown on they-axis. SPFF and ProRes S removed the most HCP throughout the 100 CV. QFF removed some HCP but broke through quickly. For this specific feed which had a high concentration of DNA, activated carbon removed the least amount of HCP.
Figure 8:
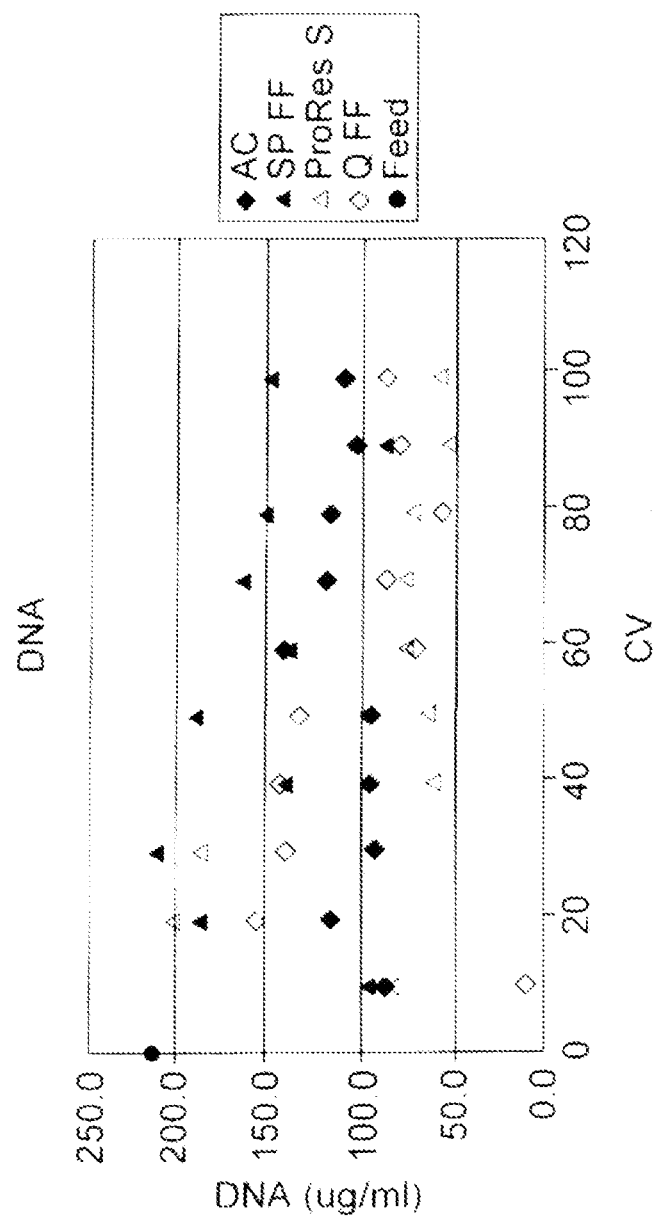
FIG. 8 depicts an x-y scatter plot demonstrating the result of an experiment to measure DNA concentration in a flow-through eluate of a null CHO-S feed with added polyclonal IgG and Herring sperm DNA, for each of the media evaluated and listed above, at every 10 CV of feed loaded up to 100 CV, including the untreated clarified feed. Column volume (CV) is shown on the x-axis and DNA concentration in µg/mL is shown on the y-axis. Each of the media evaluated, including AC, SPFF, ProRes™-S and QFF, removed DNA throughout the 100 CV, however, to different degrees.

As depicted in FIG. 5, all materials screened showed no significant loss of IgG yield over 100 column volumes loading of feed. As depicted in FIG. 6, activated carbon removed the most UV active species throughout the 100 CVs. Anion exchange material also removed UV active species to some degree throughout the 100 CVs. Further, as depicted in FIG. 7. HCP removal capacity by anion exchange resin, Q FastFlow, was limited as it breaks through from early fractions. However, cation exchange materials, Q FastFlow and ProRes™-S, removed a significant amount of HCP throughout the 100 column volumes. With the high DNA concentration (i.e., an additional 195 g/mL) in this specific experiment, activated carbon removed less HCP compared to the feeds without the added DNA. For example, in a similar experiment with the original null CHO-S feed without the addition of DNA, activated carbon removed close to 20% HCP throughout the 100 CVs (data not shown). This demonstrated some degree of competition of DNA and HCP for the adsorption to activated carbon. Further, as depicted in FIG. 8, all materials removed DNA to some extent.

Data from this example demonstrates that activated carbon, as well as materials with cation exchange, anion exchange and hydrophobic interaction functional groups, can remove impurities (HCP, DNA and UV active species) to various degrees over 100 column volumes, without significant yield loss in flow through mode from a CHO cell feed.

Example 3. Effect of Combinations of Different Materials on Impurity Removal

Figure 9:
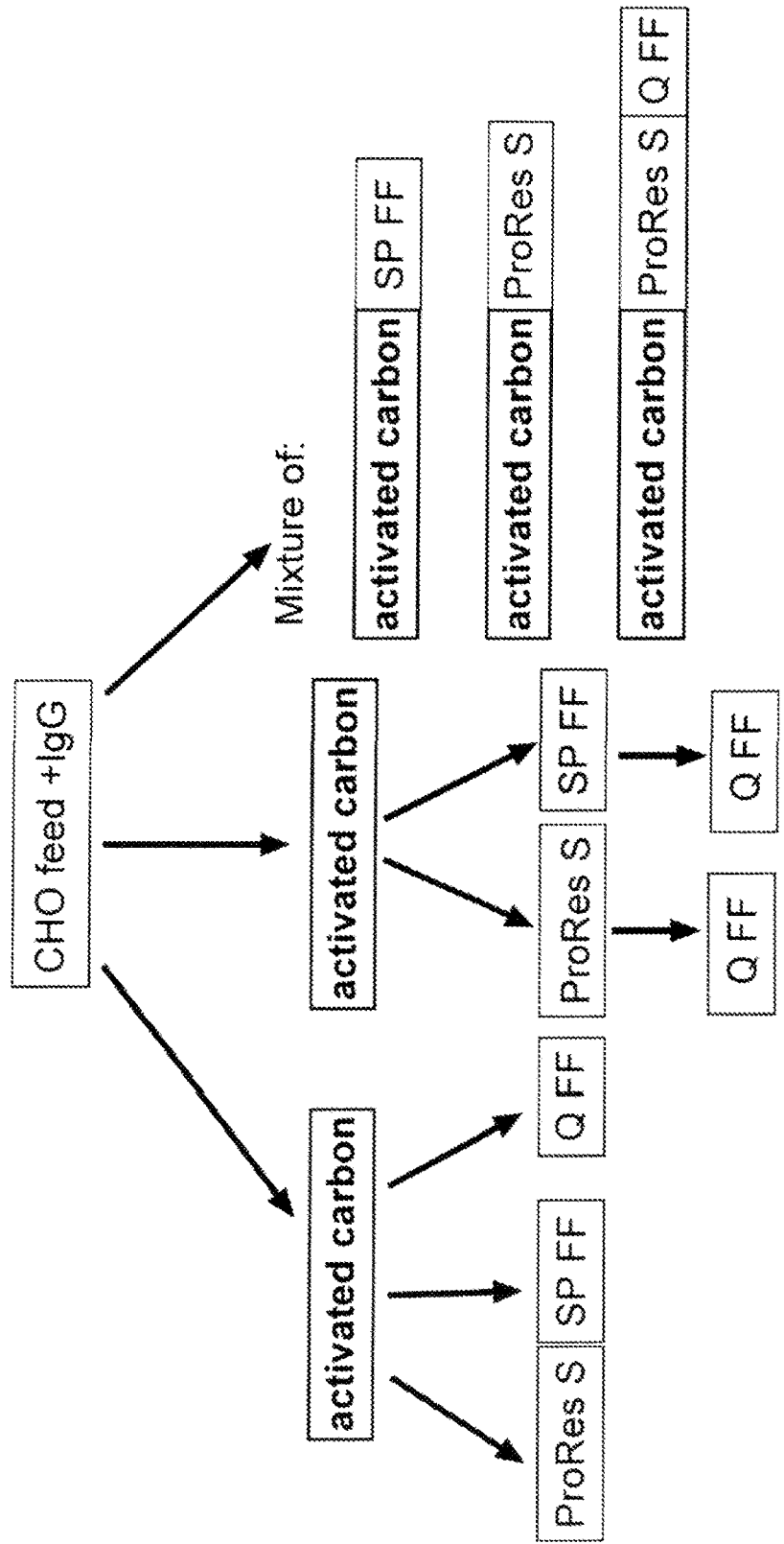
FIG. 9 is a schematic of the different exemplary modes of operation which may be used for impurity removal. The flow chart on the left depicts a representative experiment where the untreated clarified feed is loaded onto a column containing AC, followed by a column containing SPFF, ProRes™-S or QFF media. The flow chart in the middle depicts a representative experiment where the untreated clarified feed is loaded onto a column containing AC, followed by a column containing SPFF or ProRes™-S and then followed by QFF. The flow chart on the right depicts a representative experiment where untreated clarified feed is loaded onto a column containing a 1:1 (v/v) mixture of AC and SPFF; or a 1:1 (v/v) mixture of AC and ProRes™-S; or a 1:1:1 (v/v/v) mixture of AC and ProRes™-S and QFF.

In another experiment, different combinations of materials, shown in the work flow depicted in FIG. 9, were evaluated for impurity removal. The materials (1 ml) were allowed to settle and packed into a 5 ml disposable chromatography column. Columns were equilibrated with 5 CVs of PBS, loaded with 20 CVs feed and washed with 5 CVs of PBS.

Figure 11:
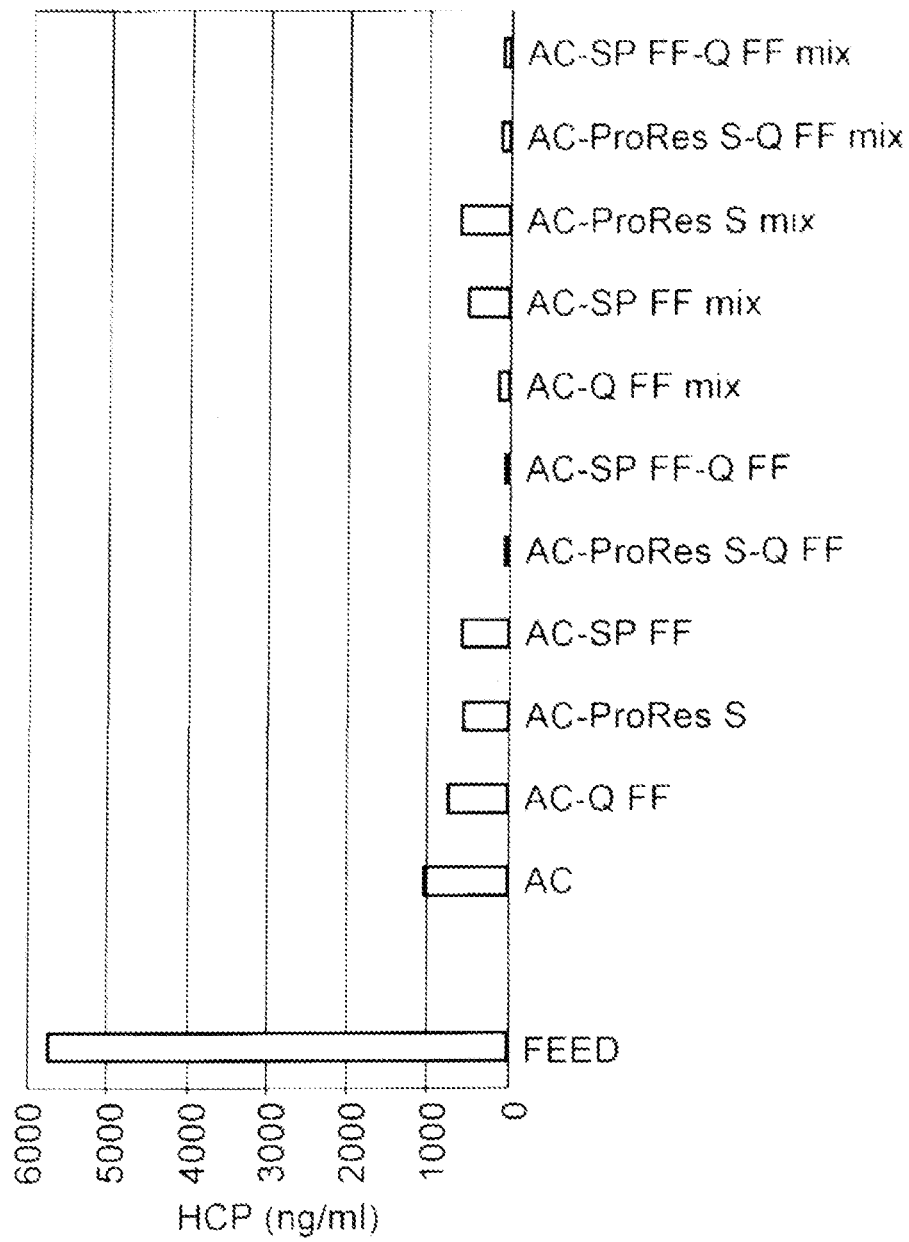
FIG. 11 depicts a bar graph which shows the host cell protein (HCP) concentration in a flow-through eluate of a null CHO-S feed with added polyclonal IgG, for each of the material combinations shown in FIG. 9, including untreated clarified feed. All materials removed HCP to some degree; however, when activated carbon was used in a process along with a cationic resin, such as, SPFF or ProRes™-S, or with an anionic resin, such as, QFF, either when used sequentially with a resin or as a mixture with a resin, removed HCP most effectively, indicating a synergetic effect of different materials.
Figure 12:
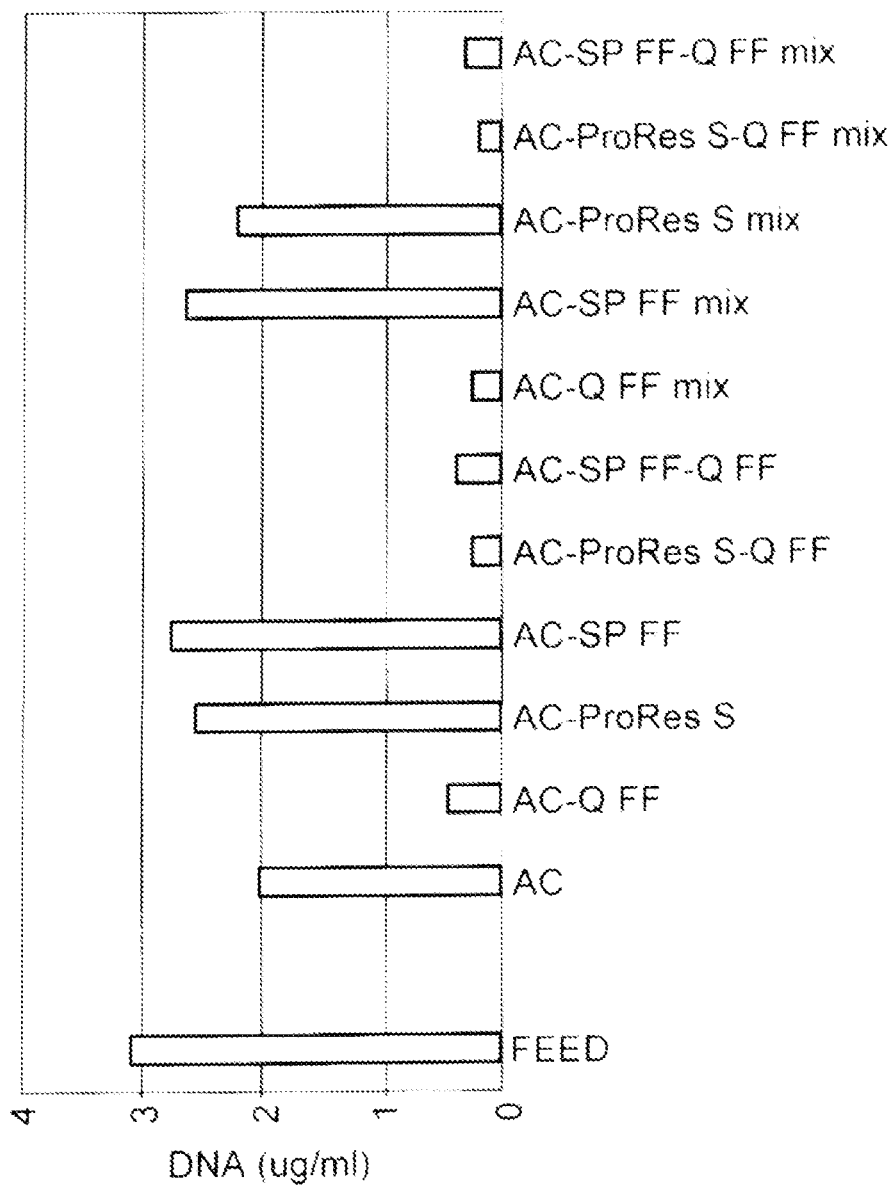
FIG. 12 depicts a bar graph which shows the DNA concentration in a flow-through eluate of a null CHO-S feed with added polyclonal IgG, for each of the material combinations shown in FIG. 9, including untreated clarified feed. All materials removed DNA to some degree; however, when activated carbon was used either sequentially with QFF or used as a mixture with QFF, it was most effective in DNA removal compared to the other materials and combinations evaluated.

The flow-through eluant fraction was further loaded on o the next disposable column of the selected media (as shown in the two workflows depicted on the left in FIG. 9). The last flow-through eluant in the work flow was analyzed. In case of the work flow depicted on the right, in which a feed went through a mixture of media, the eluant was analyzed directly. Feed was prepared using non-expressing CHO-S feed with addition of polyclonal IgG (~2.5 mg/ml) from SeraCare. Flow-through eluant fractions and the corresponding feeds were assayed for IgG yield, UV active species, HCP and DNA removal using the same methods described above in Example 1. Results are shown in FIGS. 10-12.

Figure 10:
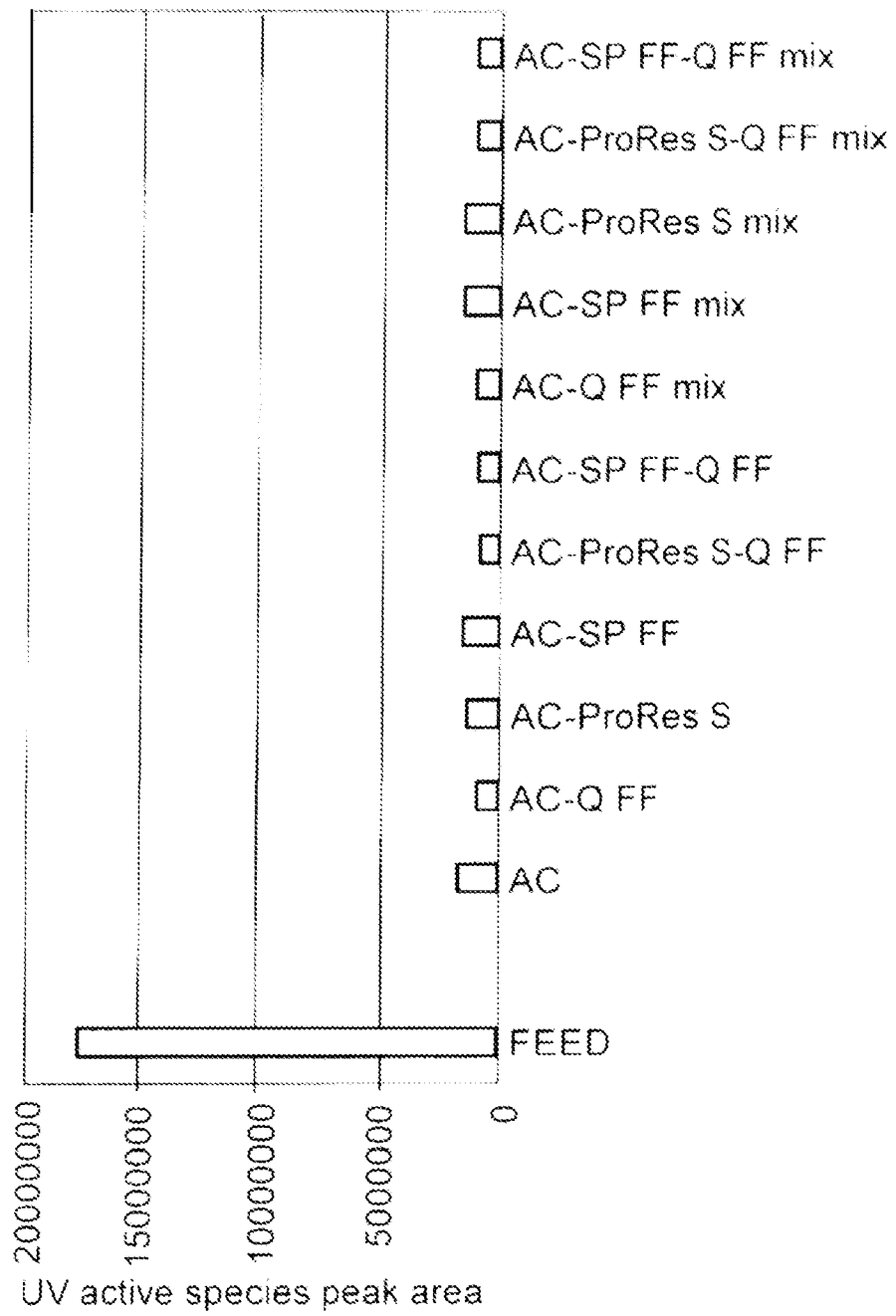
FIG. 10 depicts a bar graph demonstrating UV active species peak area (which corresponds to the quantity of UV active species) in a flow-through eluate of a null CHO-S feed with added polyclonal IgG, for each of the material combinations shown in FIG. 9, including untreated clarified feed. Activated carbon and mixtures which contain activated carbon significantly reduced the UV active species. In the cases where activated carbon and an anion exchange resin were both used in a process, either when used sequentially or as a mixture, more UV active species were removed, demonstrating a synergetic effect of different materials.

As depicted in FIG. 10, activated carbon and mixtures which contain activated carbon significantly reduced the level of UV active species. Further, while all materials exhibited HCP removal to some extent, activated carbon mixture in combination with a cationic resin showed most effective removal of HCP, as depicted in FIG. 11. Also, as depicted in FIG. 12, while all materials removed DNA to some extent, combination of activated carbon and anion exchange resin showed most effective removal of DNA.

Data from this example demonstrates that combination of activated carbon and materials with cation exchange, anion exchange and hydrophobic interaction functional groups can remove impurities (HCP, DNA and UV active species) more effectively than any single component in flow through mode from a CHO feed.

Example 4. Impurity Removal of a Protein A Elution Pool

In another experiment, standard gravity flow-through test method was used to investigate impurity removal in a post Protein A pool. Materials screened in Example 1, i.e., activated carbon, cation exchange resins (SP FF and Pro-Res™-S), anion exchange resin, Q FF, and HIC resin, Phenyl FastFlow and different combinations of these materials, were evaluated. Activated carbon or resin material (1 ml) was allowed to settle and packed into a disposable chromatography column from Evergreen. Each column was equilibrated with 5 CVs of PBS, loaded with 20 CVs of feed and washed with 5 CVs of PBS. The flow-through eluant fractions during loading step were collected. The feed used was Protein A (ProSep Ultra Plus) elution pool (~3.2 mg/ml IgG) after adjusting pH to 7.0. The feed for Protein A column was a non-expressing CHO-S spiked with polyclonal IgG.

Flow-through eluant fractions and the Protein A elution pool were evaluated for IgG yield, UV active species removal, HCP removal and DNA removal. All assays were performed as described in Example 1, except that in case of HCP, CHO-3G HCP ELISA kit (CYGNUS TECHNOLOGIES, Southport, N.C.) was used.

Figure 13:
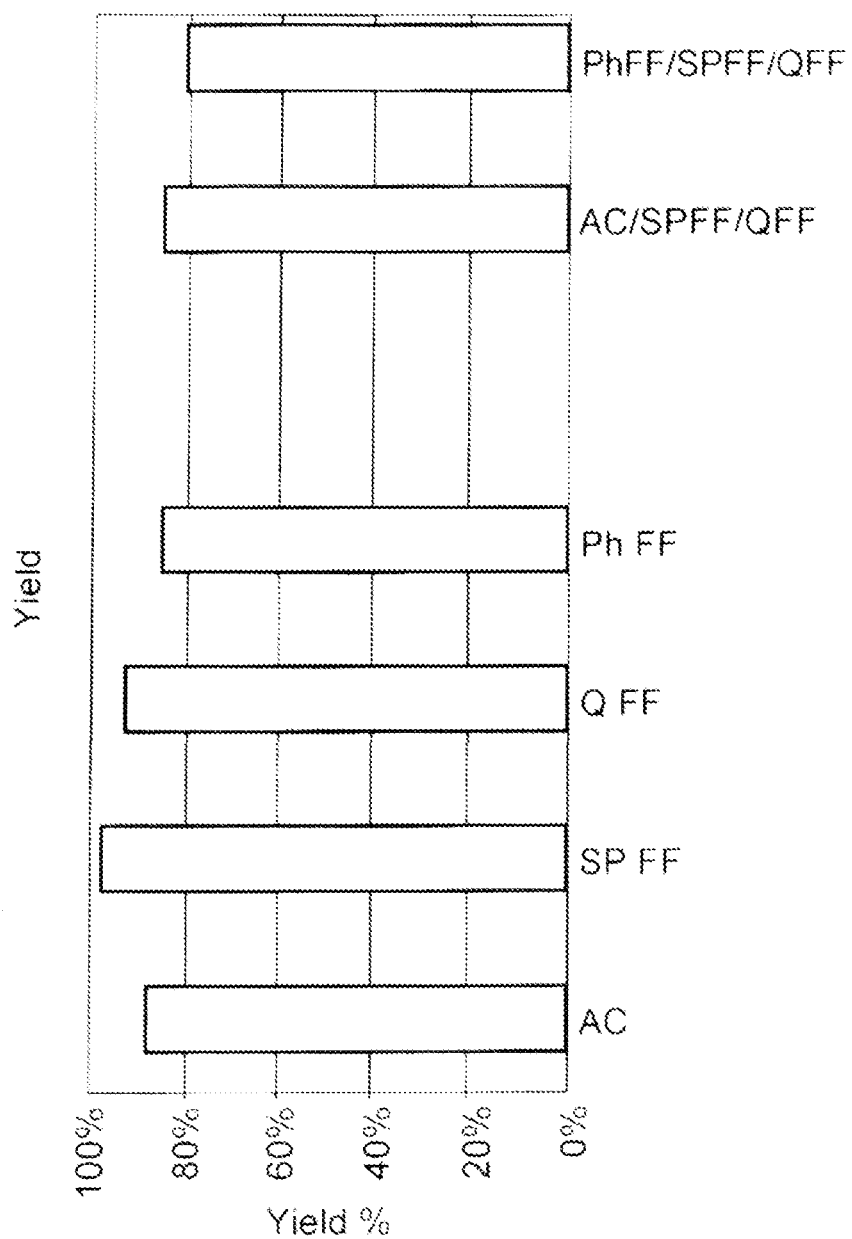
FIG. 13 depicts a bar graph demonstrating the results of an experiment to measure IgG yield in a flow-through eluate of a Protein A column elution pool for each of the materials evaluated i.e., AC; SPFF; QFF; ph FF, as well as two material combinations, a 1:1:1 (v/v/v) mixture of AC/SPFF/QFF, and a 1:1:1 (v/v/v) mixture of PhFF/SPFF/QFF. The feed for the flow-through eluate of different materials evaluated was a Protein A column elution pool generated using Prosep Ultra Plus Protein A resin from a null CHO-S feed with added polyclonal IgG. All materials screened showed higher than 80% yield.
Figure 14:
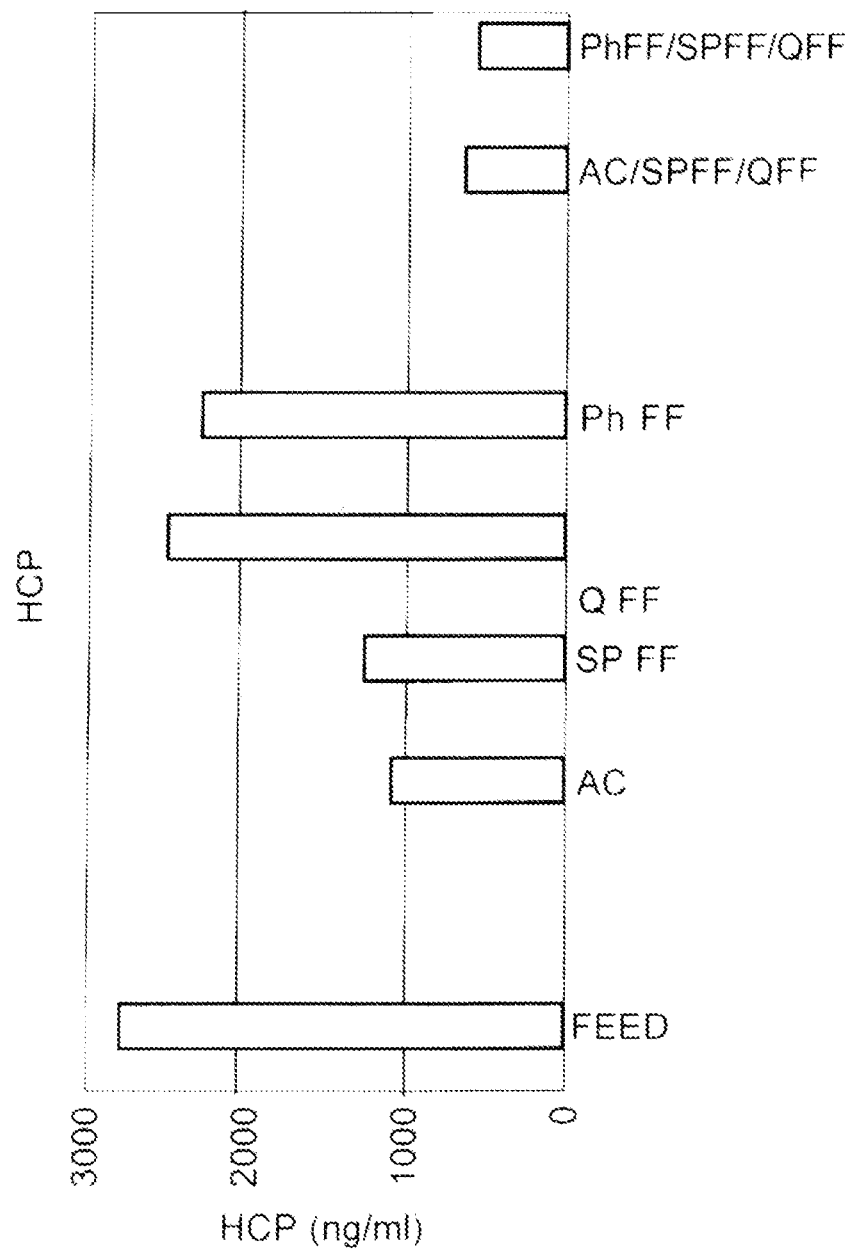
FIG. 14 depicts a bar graph demonstrating the results of an experiment to measure host cell protein (HCP) concentration in a flow-through eluate of a Protein A column elution pool for each of the materials evaluated, i.e., AC; SPFF; QFF; ph FF, as well as two material combinations, a 1:1:1 (v/v/v) mixture of AC/SPFF/QFF and a 1:1:1 (v/v/v) mixture of PhFF/SPFF/QFF. The feed for flow-through eluate of different materials evaluated was a Protein A column elution pool generated using Prosep Ultra Plus Protein A resin from a null CHO-S feed with added polyclonal IgG. All materials or material mixtures removed certain amount of HCP from the Protein A elution pool; however, activated carbon and cation exchange resin were the more effective, when used alone. When used as a mixture, AC/SPFF/QFF and PhFF/SPFF/QFF removed more HCP than any single component alone. QFF and PhFF, when used alone, removed the least amount of HCP.
Figure 15:
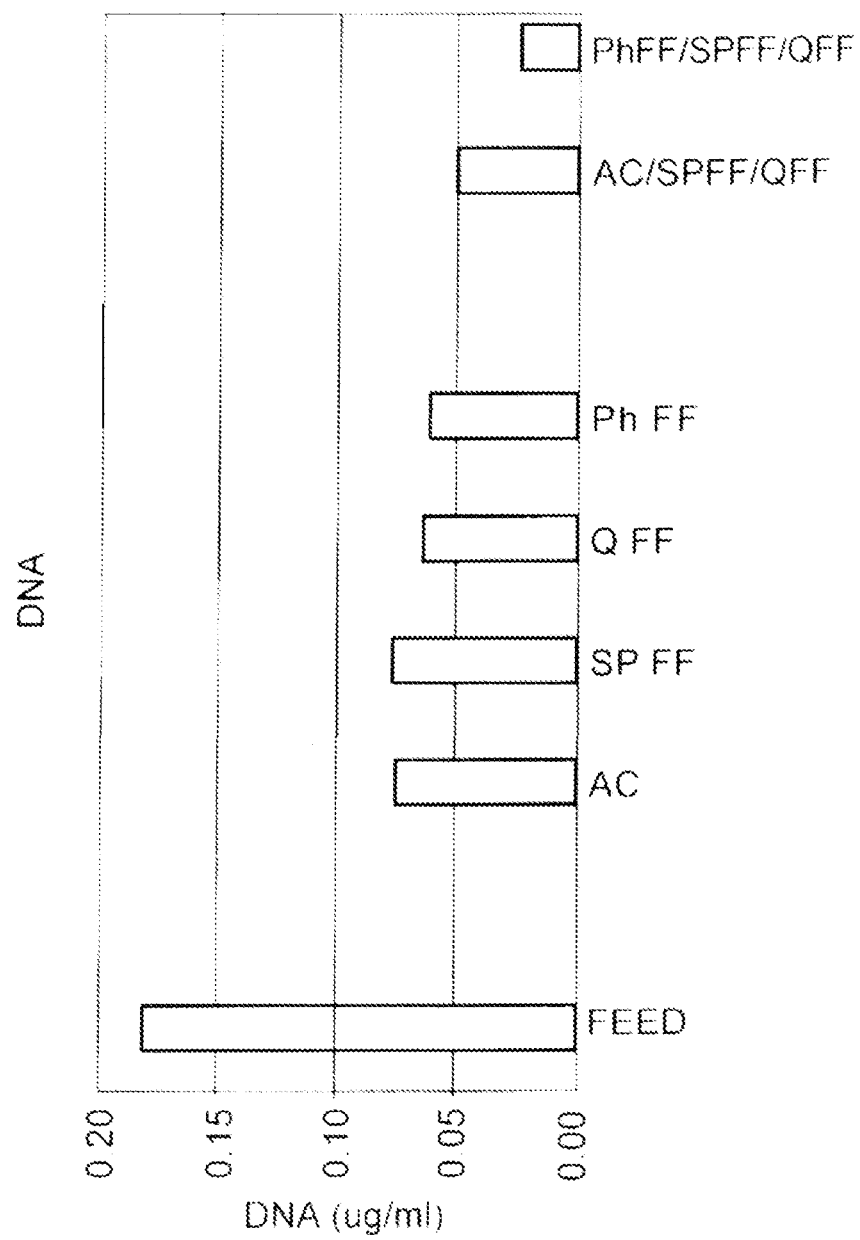
FIG. 15 a bar graph demonstrating the results of an experiment to measure DNA concentration in a flow-through eluate of a Protein A column elution pool for each of the materials evaluated, i.e., AC; SPFF; QFF; and ph FF, as well as two material combinations, a 1:1:1 mixture of AC/SPFF/QFF and a 1:1:1 mixture of PhFF/SPFF/QFF. The feed for flow-through eluate of different materials evaluated was a Protein A column elution pool generated using Prosep Ultra Plus Protein A resin from a null CHO-S feed with added polyclonal IgG. All material or material mixtures removed certain amount of DNA from Protein A elution pool with the resin mixtures AC/SPFF/QFF and PhFF/SPFF/QFF showing slight advantage over any single component.

As depicted in FIG. 13, all materials screened generated ~85% or higher yield. Activated carbon, cation exchange resin, SP FastFlow, removed the most HCP as a single material. The mixture of different materials provided the highest HCP removal, as depicted in FIG. 14. FIG. 15 depicts the fact that all material removes significant amount of DNA, partly because of the low level in the feed. Overall, mixtures of materials were generally more effective in impurity removal compared to single materials.

Data from this example demonstrates that activated carbon and materials with cation exchange, anion exchange and hydrophobic interaction functional groups, as well as the mixture of these materials can remove impurities (HCP, DNA and UV active species) to different degrees in flow through mode from a Protein A elution pool generated from a CHO feed.

Example 5. Preparation of a Representative Affinity Based (Protein A) Captured MAb Feed to Evaluate the Performance of Activated Carbon for the Purification of MAb A partially purified monoclonal antibody, referred to as MAb I, was produced using a CHO cell line culture for use as a representative affinity (Protein A) captured monoclonal antibody feed to evaluate the performance of activated carbon for purifying proteins. The cell culture was first clarified directly from a bioreactor using depth filtration media, available as Millistak+® POD filters (MILLIPORE CORPORATION, Billerica, Mass., USA). Cell culture fluid was filtered through a series of two filters, D0HC and X0HC to a final turbidity of <10 NTU, and subsequently sterile filtered with Millipore Express® SHC capsule filter.

An acrylic Quick-Scale® 14 cm ID column from Millipore Corporation, Billerica, Mass., USA was packed with Millipore ProSep-vA High Capacity Protein A media to a bed volume of approximately 3.2 L. The column was packed using a combination of flow packing with PBS and vibration. All chromatography steps were performed on a Millipore K-Prime 40-I system with detection performed using UV absorption at a wavelength of 280 nm. The column was used for MAb I purification for at least five cycles and was stored in PBS at 4° C. Prior to using the column, the column was flushed with at least 2 column volumes (CVs) of 0.15 M phosphoric acid pH 1.5-1.7 and then equilibrated with PBS until the pH was stabilized (at least 3 CVs). Typically, the day following the clarification, the sterile filtered clarified cell culture was loaded onto the Protein A column at a residence time of at least 5 minutes (i.e., at a flow rate of 500-600 mL min$^{-1}$). The column was loaded to ensure that the maximum capacity of the column was not exceeded, which was defined as 30 g of MAb I per liter of media.

Following loading of the column, the column was flushed with PBS at the same residence time until the UV trace reached baseline, typically within three CVs. The column was then washed with 20 mM sodium acetate with 0.5 M NaCl at pH 6 for at least three CVs, but for no more than five CVs. The product was then eluted using a step change to 20 mM acetic acid pH 3.0, where the capture of the elution peak was performed manually to reduce the dilution of the elution peak. The eluate was left to incubate at room temperature (20-25° C.) for at least 30 minutes to a maximum of 1.5 hours. Following incubation, the pH of the elution pool was titrated to pH 5±0.2 using 2 M Tris base at pH 10 or higher. The starting pH of the elution pool was typically near pH 4.0 and required less than 5% volume addition of the Tris base solution. During the titration of the elution pool visible precipitates were observed. The removal of the precipitates was performed using a Millipore Millistak+® X0HC lab scale POD prior to sterile filtration of the elution pool, where at least two 0.027 m$^2$ PODs were required to clear the precipitates of the entire elution pool. Following the depth filtration, the eluate was sterile filtered using Millipore Express Plus Stericup filter units and stored at 4° C. until used.

Example 6. Preparation of a Representative Non-Affinity Based (Cation Exchange) Captured MAb Feed to Evaluate the Performance of Activated Carbon for the Purification of MAb A partially purified monoclonal antibody, referred to as MAb I, was produced using a CHO cell line culture for use as a representative non-affinity (cation exchange) captured monoclonal antibody feed to evaluate the performance of activated carbon for purifying proteins. A MAb I clarified cell culture fluid was made as discussed in Example 5. Cell culture fluid was filtered through a series of two filters, D0HC and X0HC to a final turbidity of <10 NTU, and subsequently sterile filtered with Millipore Express® SHC capsule filter.

A 22 cm ID glass Vantage® laboratory column from Millipore Corporation, Billerica, Mass., USA was packed with the cation-exchange (CEX) media Fractogel® SO$_3^-$ (M). The column was packed using PBS on an Äkta® Explorer 100 (GE HEALTHCARE, Uppsala, Sweden) with superficial linear velocities of approximately 1000 cm hr$^{-1}$. The pressure drop across the column was kept below three bar during packing and all subsequent column runs. The bed compression of the column was approximately 15% with a packed bed volume of 75 mL. The packing efficiency of the column was measured using a pulse injection of 500 µL of 25 mM Tris, 1 M NaCl, 3% (v/v) acetone at pH 6.9 at a superficial linear velocity of 100 cm hr$^{-1}$ using PBS as the running buffer. The height equivalent to a theoretical plate (HETP) was calculated using the acetone peak using standard methods after accounting for the dead volume of the system and was calculated as 0.053 cm with an asymmetry of the peak of 1.3, indicating the column was packed sufficiently. The NaCl peak showed a larger level of peak tailing, but this is likely related to the interaction of the salt ions with the media and not a representation of the column efficiency.

Prior to the first use of the column, a complete blank run was performed without a protein load so as to reduce and/or eliminate any solution related interactions with the base media. Prior to loading, the column was equilibrated with 20 mM sodium acetate pH 5 for at least five CVs. The column was loaded with a clarified cell culture containing MAb I that had the pH lowered to pH 5 using glacial acetic acid. When lowering the pH of the cell culture, precipitates were often observed and were removed using a combination of centrifugation and depth filtration using a Millipore Millistak+® X0HC lab scale POD.

The loading solution was sterile filtered prior to loading using Millipore Express Plus Stericup filter units. The sterile filtered load was loaded onto the column using a residence time of 10 min in an effort to maximize the column capacity (approximately 45 g MAb I per L of media), while minimizing the pressure drop across the column. Following loading, the column was flushed with equilibration buffer for five CVs. The column was then washed with 20 mM sodium acetate, 0.1 M NaCl pH 5.0 buffer for five CVs. The elution from the column was performed with a step change to 20 mM sodium acetate, 0.25 M NaCl pH 6.0 for at least five CVs. The eluate was fractionated and the peak fractions were pooled and stored at 4° C. for further use. The column was then washed with 20 mM sodium acetate, 1 M NaCl pH 6.0 to remove strongly bound proteins, which were determined to be mostly host cell proteins (HCP). The column was then washed with 0.5 N NaOH for five CVs at a slower flow rate equivalent to a 30 minute residence time. The column was then washed with five CVs of the equilibration buffer and stored at room temperature (20-25° C.) for future use.

Example 7. Evaluation of Various Adsorbers by Flow-Through Treatment of an Affinity Captured MAb Eluate Activated carbon was compared in a flow-through application to several different commercially available adsorbent media that are commonly used for the purification of proteins including anion exchange (ChromaSorb™), cation exchange (HiTrap SP FF, HiTrap CM FF), and hydrophobic interaction (HiTrap Phenyl FF, HiTrap Butyl FF) chemistries for the purification of an affinity (Protein A) captured monoclonal antibody eluate to demonstrate that the activated carbon is unique and unexpectedly efficient for the removal of impurities from protein solutions.

A partially purified MAb I affinity (Protein A) captured eluate was prepared according to Example 5. The eluate of MAb I was adjusted from approximately pH 5 to pH 7 with Tris base (2 M) and filtered through a 0.22 micron Millipore Express Plus Stericup filter unit. The solution is referred to herein as the MAb I Protein A eluate.

Nuchar HD and HD Nuchar activated carbon are used herein interchangeably and refer to the grade of powdered activated carbon obtained from MeadWestVaco Corporation, Richmond, Va., USA. Glass Omnifit Chromatography Columns (10 mm diameter, 100 mm length) were loaded with 250 mg of HD Nuchar activated carbon slurried in water to give a packed column volume of 1 mL. 0.2 mL ChromaSorb membrane devices were manufactured using 0.65 micron-rated polyethylene membrane modified with polyallyl amine, available from Millipore Corporation, Billerica, Mass., USA, in devices of various sizes. The membrane was cut in 25 mm discs; 5 discs were stacked and sealed in an overmolded polypropylene device of the same type as the OptiScale 25 disposable capsule filter devices commercially available from Millipore Corporation. The devices include an air vent to prevent air locking, and have an effective filtration area of 3.5 $cm^2$ and volume of 0.2 mL.

1 mL pre-packed chromatography columns HiTrap SP FF, HiTrap CM FF, HiTrap Phenyl FF (high sub), and HiTrap Butyl FF were purchased from GE Healthcare, Pittsburgh, Pa., USA, and equilibrated with buffer solution (Tris-HCl buffer, 25 mM, pH 7) prior to use. Six flow-through purification trains were assembled: a) activated carbon, b) ChromaSorb, c) HiTrap SP FF, d) HiTrap CM FF, e) HiTrap Phenyl FF, and f) HiTrap Butyl FF. Subsequently, 96 mL of the MAb I Protein A eluate was passed through each setup at a flow rate of 0.25 mL/min. After passing through the purification trains, the solutions were analyzed for host cell protein (HCP), IgG concentration, and residual Protein A. HCP analysis was performed using a commercially available ELISA kit from Cygnus Technologies, Southport, N.C., USA, catalog number F550, following kit manufacturer's protocol. IgG concentration was measured using an Agilent HPLC system equipped with a Poros® A Protein A analytical column. Protein A analysis was performed using a commercially available ELISA kit from Meridian Life Sciences, Saco, Me., USA, Kit C0Z51-188. Results are summarized in Table IV.

The results show that activated carbon removed the greatest amount of impurities with a log reduction value (LRV) of host cell protein (HCP) of 0.87. The LRV of HCP value for activated carbon was significantly higher in comparison to the commercially available media (anion exchange, cation exchange, hydrophobic interaction) examined, which had LRV of HCP that ranged from 0.19 to 0.35. The residual Protein A from affinity capture step was also efficiently removed below the detectable limit by activated carbon. The only commercially available media that was observed to remove any significant amount of residual Protein A was the anion exchange media (ChromaSorb™), which also lowered the concentration of residual Protein A below the detectable limit. Despite the higher amounts of impurities removed by the activated carbon it still had excellent recovery (96%) of the monoclonal antibody product (MAb I), which was similar to the product recoveries (82-100%) observed for the commercially available media that were examined.

TABLE IV

| flow-through adsorber | MAb I (mg/mL) | Recovery MAb I | HCP (ng/mL) | HCP (ppm) | LRV of HCP | Protein A (ng/mL) | Protein A (ppm) |
|---|---|---|---|---|---|---|---|
| Untreated (control) | 7.18 | NA | 869 | 121 | NA | 4.61 | 0.62 |

TABLE IV-continued

| flow-through adsorber | MAb I (mg/mL) | Recovery MAb I | HCP (ng/mL) | HCP (ppm) | LRV of HCP | Protein A (ng/mL) | Protein A (ppm) |
|---|---|---|---|---|---|---|---|
| Activated carbon | 6.88 | 96% | 112 | 16 | 0.87 | ND | ND |
| ChromaSorb | 5.92 | 82% | 320 | 54 | 0.35 | ND | ND |
| HiTrap SP FF | 6.09 | 85% | 364 | 60 | 0.31 | 2.95 | 0.48 |
| HiTrap CM FF | 6.28 | 87% | 463 | 74 | 0.22 | 2.72 | 0.43 |
| HiTrap Phenyl FF | 6.89 | 96% | 385 | 56 | 0.33 | 3.21 | 0.47 |
| HiTrap Butyl FF | 7.21 | 100% | 563 | 78 | 0.19 | 4.25 | 0.59 |

ND—Not Detected
NA—Not Applicable

Example 8. Static Soak Treatment of an Affinity Captured Eluate of a MAb with Activated Carbon and/or Anion Exchange Media Activated carbon alone and in combination with an anion exchange media was examined for the removal of impurities from an affinity (Protein A) captured monoclonal antibody eluate to demonstrate a unique and unexpectedly effective method for the removal of impurities.

A partially purified MAb I affinity (Protein A) captured eluate was prepared according to Example 5. The eluate of MAb I was adjusted from approximately pH 5 to pH 7 with Tris base (2 M) and filtered through a 0.22 micron Millipore Express Plus Stericup filter unit. The solution is referred to herein as the MAb I Protein A eluate.

Nuchar RGC and RGC Nuchar activated carbon are used herein interchangeably and refer to the grade of powdered activated carbon obtained from MeadWestVaco Corporation, Richmond, Va., USA. In a representative experiment, a 7 mm diameter circular portion (5 µL) of the ChromaSorb™ membrane and/or 10 mg of ROC Nuchar activated carbon were added to a 1.5 mL centrifuge tube along with Tris-HCl buffer, 25 mM, pH 7 to equilibrate the adsorbent media. The tubes were centrifuged and the supernatant equilibration buffer was removed. Subsequently, a 1 mL volume of the MAb I Protein A eluate was added to a 1.5 mL centrifuge tube containing the equilibrated adsorbent(s). The adsorbent media and the eluate were allowed to interact for 18 hours at room temperature under gentle rotation. The tubes were then subjected to centrifugation and the supernatant solutions were analyzed for host cell protein (HCP) and IgG concentration.

HCP analysis was performed using a commercially available ELISA kit from Cygnus Technologies, Southport, N.C., USA, catalog number F550, following kit manufacturer's protocol. IgG concentration was measured using an Agilent HPLC system equipped with a Poros® A Protein A analytical column. Results of one such experiment are summarized in Table V.

The results show that activated carbon alone and in combination with an anion exchange media was unexpectedly effective for the removal of impurities from the monoclonal antibody solution. The combination of activated carbon and the anion exchange media (ChromaSorb) removed the greatest amount of impurities with a log reduction value (LRV) of host cell protein (HCP) of 1.43. The individual activated carbon and anion exchange media had LRVs of HCP of 1.21 and 0.36 respectively. The activated carbon alone and in combination with an anion exchange media both had excellent recoveries of the monoclonal antibody product of 95% and 95% respectively.

TABLE V

| Adsorbent media | MAb I (mg/mL) | Recovery MAb I | HCP (ng/mL) | HCP (ppm) | LRV of HCP |
|---|---|---|---|---|---|
| Control (nothing added) | 6.92 | NA | 1748 | 252 | NA |
| Activated Carbon | 6.58 | 95% | 102 | 16 | 1.21 |
| ChromaSorb | 6.74 | 97% | 743 | 110 | 0.36 |
| Activated Carbon and ChromaSorb | 6.58 | 95% | 62 | 9 | 1.43 |

NA—Not Applicable

Example 9. Static Soak Treatment of an Affinity Captured Eluate of a MAb with Activated Carbon and/or an Anion Exchange Media Activated carbon alone and in combination with an anion exchange media was examined for the removal of impurities from an affinity (Protein A) captured monoclonal antibody eluate that contains a different monoclonal antibody than MAb I (referred to as MAb II) to demonstrate that activated carbon alone and in combination with an anion exchange media provides a unique and unexpectedly effective method that can be applied to purification of a variety of different monoclonal antibodies.

A second partially purified MAb II affinity (Protein A) captured eluate was prepared according to Example 5. The eluate of MAb II was adjusted from approximately pH 5 to pH 7 with Tris base (2 M) and filtered through a 0.22 micron Millipore Express Plus Stericup filter unit. The solution is referred to herein as the MAb II Protein A eluate.

A 7 mm diameter circular portion (5 µL) of the ChromaSorb membrane and/or 10 mg of RGC Nuchar activated carbon were added to a 1.5 mL centrifuge tube along with Tris-HCl buffer, 25 mM, pH 7 in order to equilibrate the adsorbent media. The tubes were centrifuged and the supernatant equilibration buffer was removed. Subsequently, 1 mL volume of the pH adjusted MAb II Protein A eluate was added to a 1.5 mL centrifuge tube containing the equilibrated adsorbent(s). The adsorbent media and the eluate were allowed to interact for 18 hours at room temperature under gentle rotation. The tubes were then subjected to centrifugation and the supernatant solutions were analyzed for host cell protein (HCP) and IgG concentration. HCP analysis was performed using a commercially available ELISA kit from Cygnus Technologies, Southport, N.C., USA (catalog number F550), following kit manufacturer's protocol. IgG concentration was measured using an Agilent HPLC system equipped with a Poros® A Protein A analytical column. Results are summarized in Table VI.

The results show that activated carbon alone and in combination with an anion exchange media was unexpectedly effective for the removal of impurities from a solution containing a second type of monoclonal antibody. The combination of activated carbon and the anion exchange media (ChromaSorb™) removed the greatest amount of impurities with a log reduction value (LRV) of host cell protein (HCP) of 1.78. The individual activated carbon and anion exchange media had LRVs of HCP of 1.08 and 0.64 respectively. The activated carbon alone and in combination with an anion exchange media both had good recoveries of the monoclonal antibody product of 87% and 85% respectively.

TABLE VI

| Adsorbent media | MAb II (mg/mL) | Recovery MAb II | HCP (ng/mL) | HCP (ppm) | LRV of HCP |
|---|---|---|---|---|---|
| Control (nothing added) | 18.19 | NA | 23418 | 1287 | NA |
| Activated Carbon | 15.89 | 87% | 4681 | 295 | 0.64 |
| ChromaSorb | 16.08 | 88% | 1711 | 106 | 1.08 |
| Activated Carbon and ChromaSorb | 15.44 | 85% | 329 | 21 | 1.78 |

NA—Not Applicable

Example 10. Static Soak Treatment of a Non-Affinity Captured Eluate of MAb I with Activated Carbon and/or an Anion Exchange Media Activated carbon alone and in combination with an anion exchange media was examined for the removal of impurities from a non-affinity (cation exchange) captured monoclonal antibody eluate to demonstrate that activated carbon alone and in combination with an anion exchange media provides a unique and unexpectedly effective method for the removal of impurities. Relative to affinity (Protein A) captured eluate the non-affinity (cation exchange) captured eluate contains different types of impurities at significantly higher levels. The application of activated carbon for the purification of a non-affinity captured eluate demonstrates that this method is general and can be applied to the purification of a variety of different protein eluates.

In a separate experiment, partially purified MAb I CEX eluate was prepared as described in Example 6. The eluate was diluted by a factor of 4 with a buffer solution (Tris-HCl buffer, 25 mM, pH 7) and then filtered through a 0.22 micron Millipore Express Plus Stericup filter unit. The solution is referred to herein as the MAb I CEX eluate.

Two 10 mm diameter circular portions (19.6 µL) of the ChromaSorb membrane and/or 20 mg of RGC Nuchar activated carbon were added to a 1.5 mL centrifuge tube along with Tris-HCl buffer, 25 mM, pH 7 in order to equilibrate the adsorbent media. The tubes were centrifuged and the supernatant equilibration buffer was removed. Subsequently, a 1 mL volume of the MAb I CEX eluate was added to a 1.5 mL centrifuge tube containing the equilibrated adsorbent(s). The adsorbent media and the eluate were allowed to interact for 18 hours at room temperature under gentle rotation. The tubes were then subjected to centrifugation and the supernatant solutions were analyzed for host cell protein (HCP) and IgG concentration. HCP analysis was performed using a commercially available ELISA kit from Cygnus Technologies. Southport, N.C., USA, catalog number F550, following kit manufacturer's protocol. IgG concentration was measured using an Agilent HPLC system equipped with a Poros® A Protein A analytical column. Results are summarized in Table VII.

The results show that activated carbon alone and in combination with an anion exchange media was unexpectedly effective for the removal of impurities from a monoclonal antibody solution that was captured from cell culture using a non-affinity (cation exchange) chromatography. Non-affinity (cation exchange) based capture media binds more impurities along with the monoclonal antibody than the more specific affinity (Protein A) based capture media. Therefore non-affinity captured eluate contains different types of impurities at significantly higher levels. The combination of activated carbon and the anion exchange membrane (ChromaSorb™) removed the greatest amount of impurities with a log reduction value (LRV) of host cell protein (HCP) of 1.45. The individual activated carbon and anion exchange media had LRVs of HCP of 1.20 and 0.55 respectively. The activated carbon alone and in combination with an anion exchange media both had good recoveries of the monoclonal antibody product of 95% and 74% respectively.

TABLE VII

| | MAb I (mg/mL) | recovery of MAb I | HCP (ng/mL) | HCP (ppm) | LRV of HCP |
|---|---|---|---|---|---|
| Control | 3.14 | NA | 64,254 | 20,463 | NA |
| activated carbon | 2.99 | 95% | 17,091 | 5,716 | 0.55 |
| ChromaSorb | 2.93 | 93% | 3,817 | 1,303 | 1.20 |
| activated carbon and ChromaSorb | 2.32 | 74% | 1,676 | 722 | 1.45 |

NA—Not Applicable

Example 11. Static Soak Treatment of an Affinity Captured Eluate of MAb I with Activated Carbon at Different pH Values Activated carbon was examined for the removal of impurities from an affinity (Protein A) captured monoclonal antibody eluate at different solution pHs to demonstrate that activated carbon is effective over a variety of different solution conditions.

In a separate experiment, a partially purified MAb I affinity (Protein A) captured eluate was prepared according to Example 5. The eluate of MAb I was adjusted from approximately pH 5 to pH 7 with Tris base (2 M) and filtered through a 0.22 micron Millipore Express Plus Stericup filter unit. The solution is referred to herein as the MAb I Protein A eluate.

The pH of MAb I Protein A eluate (20 mL) was adjusted to 5, 6, 7, or 8 by the addition of Tris base (2 M) or acetic acid (3 M). The resulting pH adjusted MAb I Protein A eluates were subsequently sterile filtered using Millipore Express® 0.22 micron membrane to remove any cloudiness. RGC Nuchar activated carbon (10 mg) was then added to a 1.5 mL centrifuge tubes along with Tris-HCl buffer, 25 mM, pH 7 in order to equilibrate the activated carbon. The tubes were centrifuged and the supernatant equilibration buffer was removed. 1 mL of the pH adjusted MAb I Protein A eluates were subsequently added to the tubes. The adsorbent media and the eluates were allowed to interact for 18 hours at room temperature under gentle rotation. The tubes were then subjected to centrifugation and 0.5 mL of the supernatant was removed and analyzed for host cell protein (HCP) and IgG concentration. HCP analysis was performed using a commercially available ELISA kit from Cygnus Technologies, Southport, N.C., USA, catalog number F550, following kit manufacturer's protocol. IgG concentration was measured using an Agilent HPLC system equipped with a Poros® A Protein A analytical column. Results are summarized in Table VIII.

The results show that activated carbon was unexpectedly effective for the removal of impurities from a monoclonal antibody solution over a wide pH range. The log reduction value (LRV) of host cell protein (HCP) was very similar for pH 6, pH 7, and pH 8 ranging from 1.27 to 1.30 LRV of HCP. Activated carbon still provided selective impurity removal at pH 5 although the LRV of HCP was reduced to 0.70. The activated carbon had excellent recoveries of the monoclonal antibody product ranging from 90% to 95% for all the pH conditions examined.

TABLE VIII

| pH | MAb I (mg/mL) control | MAb I (mg/mL) After A.C. | Recovery of MAb I | HCP (ng/mL) control | HCP (ng/mL) after A.C. | HCP (ppm) control | HCP (ppm) after A.C. | LRV of HCP |
|---|---|---|---|---|---|---|---|---|
| 5 | 7.31 | 6.97 | 95% | 5,505 | 1,048 | 753 | 150 | 0.70 |
| 6 | 7.26 | 6.88 | 95% | 1,986 | 101 | 274 | 15 | 1.27 |
| 7 | 7.04 | 6.79 | 96% | 1,889 | 91 | 268 | 13 | 1.30 |
| 8 | 8.63 | 7.76 | 90% | 1,556 | 75 | 180 | 10 | 1.27 |

Example 12. Flow-Through Treatment of an Affinity Captured Eluate of MAb I with Activated Carbon and/or Anion Exchange Media Activated carbon alone and in combination with an anion exchange media was examined in a flow-through application for the removal of impurities from an affinity (Protein A) captured monoclonal antibody eluate to demonstrate that activated carbon alone and in combination with an anion exchange media provides a unique and unexpectedly effective method for the removal of impurities under flow-through conditions commonly used for large scale purification of proteins.

A partially purified MAb I affinity (Protein A) captured eluate was prepared according to Example 5. The eluate of MAb I was adjusted from approximately pH 5 to pH 7 with Tris base (2 M) and filtered through a 0.22 micron Millipore Express Plus Stericup filter unit. The solution is referred to herein as the MAb I Protein A eluate.

Glass Omnifit Chromatography Columns (10 mm diameter, 100 mm length) were loaded with 250 mg of HD Nuchar activated carbon slurried in water to give a packed column volume of 1 mL. The columns were equilibrated with buffer solution (Tris-HCl buffer, 25 mM, pH 7). A 0.2 mL ChromaSorb device, fabricated as described above in Example 7, was also equilibrated with buffer solution (Tris-HCl buffer, 25 mM, pH 7). Three purification trains were subsequently assembled. The first consisting of a ChromaSorb device, the second consisting of an activated carbon column, and the third consisting of an activated carbon column followed by a ChromaSorb device. 100 mL of the MAb I Protein A eluate was passed through each set up at a flow rate of 0.25 mL/min. Ten 10 mL fractions of the eluate were collected. Pooled samples of all ten as well as selected individual fractions were analyzed for host cell protein (HCP) and IgG concentration. HCP analysis was performed using a commercially available ELISA kit from Cygnus Technologies, Southport, N.C., USA, catalog number F550, following kit manufacturer's protocol. IgG concentration was measured using an Agilent HPLC system equipped with a Poros® A Protein A analytical column. Results are summarized in Table IX.

Figure 16:
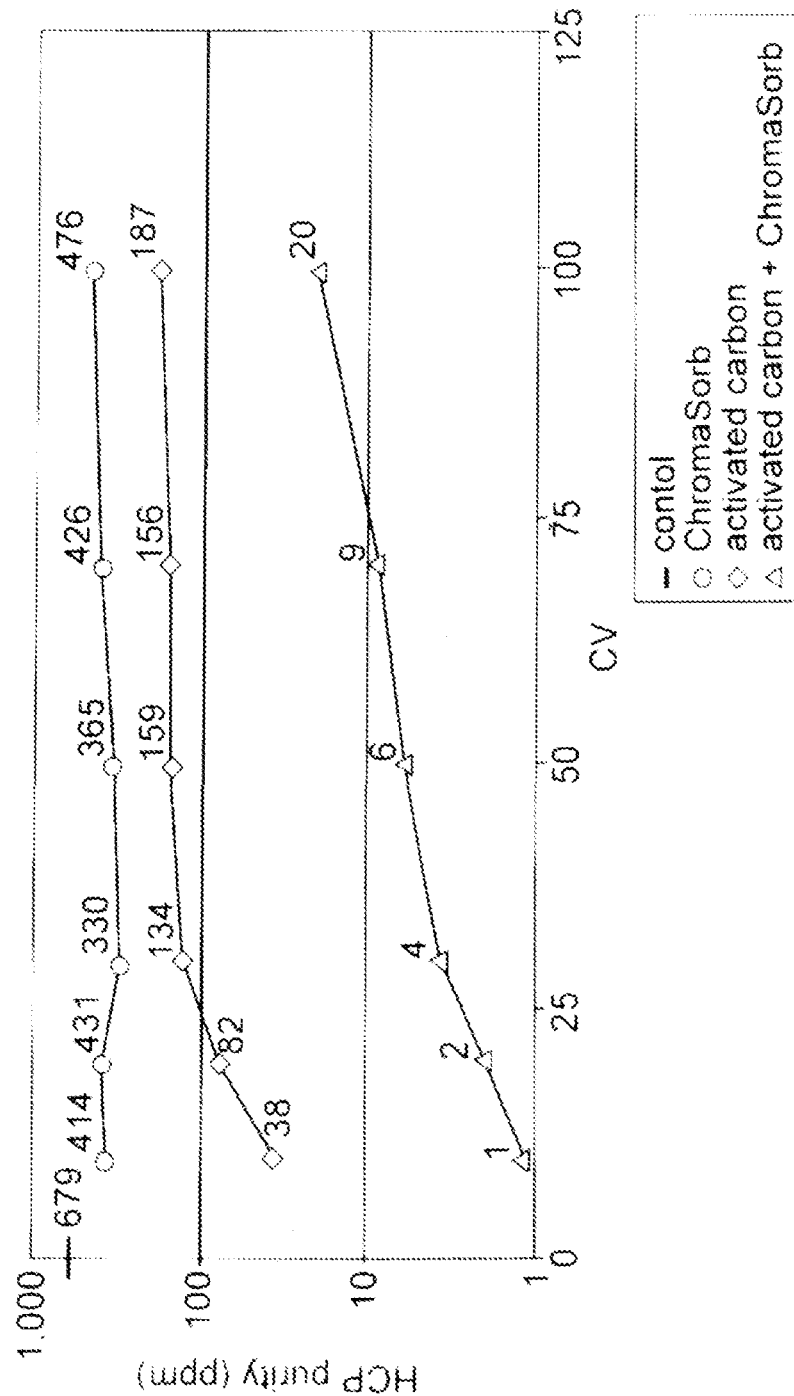
FIG. 16 is a graph demonstrating the results of an experiment to measure the concentration of HCP relative to that of the product (i.e., a monoclonal antibody) in ppm for the individual fractions of a monoclonal antibody solution, where the solution was captured from clarified cell culture using Protein A chromatography (referred to as Protein A eluate) and was subsequently subjected to three separate flow-through purification trains. The first train employed a 0.2 mL ChromaSorb™ anion-exchange membrane device composed of 5 layers; the second train employed a 1 mL packed column of HD Nuchar activated carbon; and the third train employed a 1 mL activated carbon column followed by a 0.2 mL ChromaSorb™ anion-exchange membrane. Ten 10 mL fractions of the eluate were collected from each purification train and select fractions were analyzed for host cell protein (HCP) and IgG concentration. The X-axis of the graph depicts the end point of collection for the 10 mL fraction in column volumes (CVs) of the eluate from the activated carbon column. The Y-axis of the graph depicts the concentration of HCP relative to that of the product (i.e., a monoclonal antibody) in ppm for the individual fractions of an activated carbon eluate. The graph demonstrates that the flow-through treatment of the affinity captured eluate with activated carbon alone and in combination with an anion exchange media was unexpectedly effective for the removal of impurities from the monoclonal antibody solution.
Figure 17:
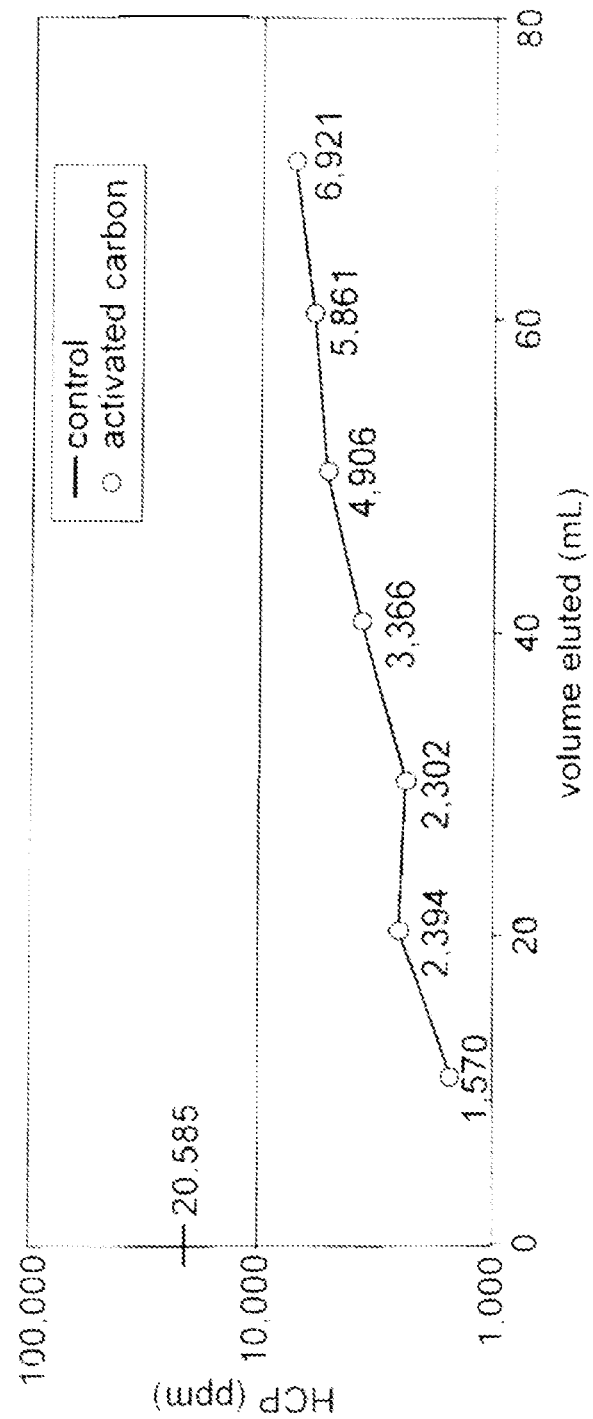
FIG. 17 is a graph demonstrating the results of an experiment to measure the concentration of HCP relative to that of the product (i.e., a monoclonal antibody) in ppm for the individual fractions of a monoclonal antibody solution, where the solution was captured from clarified cell culture using cation exchange (CEX) chromatography (referred to as CEX eluate) and was subsequently subjected to purification with a 1 mL packed column of HD Nuchar activated carbon. Seven 10 mL fractions of the eluate were collected, which were analyzed for host cell protein (HCP) and IgG concentration. The X-axis of the graph depicts the end point of collection for the 10 mL fraction in eluted volume (mL) of the eluate from the activated carbon column. The Y-axis of the graph depicts the concentration of HCP relative to that of the product (i.e., a monoclonal antibody) in ppm for the individual fractions. The graph demonstrates that activated carbon can be used to remove impurities from a variety of different protein solutions.

As depicted in FIG. 16 and summarized in Table IX, the results show that flow-through treatment of the affinity captured eluate with activated carbon alone and in combination with an anion exchange media was unexpectedly effective for the removal of impurities from the monoclonal antibody solution. The combination of activated carbon and the anion exchange membrane (ChromaSorb) removed the greatest amount of impurities with a log reduction value (LRV) of host cell protein (HCP) of 1.95. The individual activated carbon and anion exchange media had LRVs of HCP of 0.96 and 0.23 respectively. The activated carbon alone and in combination with an anion exchange media both had excellent recoveries of the monoclonal antibody product ranging of 96% and 98% respectively.

TABLE IX

| Flow-through train | MAb I (mg/mL) | recovery of MAb I | HCP (ng/mL) | HCP (ppm) | LRV of HCP |
|---|---|---|---|---|---|
| untreated (control) | 9.21 | NA | 6,259 | 679 | NA |
| ChromaSorb only | 8.92 | 97% | 3,538 | 397 | 0.23 |
| Activated Carbon only | 9.03 | 98% | 1,330 | 148 | 0.96 |
| Activated Carbon followed by ChromaSorb | 8.81 | 96% | 67 | 8 | 1.95 |

NA—Not Applicable

Example 13. Flow-Through Treatment of an Affinity Captured Eluate of MAb I with Various Anion Exchange Media Alone or after Treatment with Activated Carbon Activated carbon was examined alone and in combination with a variety of different commercially available anion exchange media for the removal of impurities from an affinity (Protein A) captured monoclonal antibody eluate to demonstrate activated carbon can be combined with various different anion exchange media. The commercially available anion exchange media examined included primary amines (ChomaSorb) and quaternary amines (Sartobind Q, Mustang Q, HiTrap Q FF). The commercially available anion exchange chemistries were examined supported on a membrane (ChomaSorb, Sartobind Q, Mustang Q) and on a resin (HiTrap Q FF).

A partially purified MAb I affinity (Protein A) captured eluate was prepared according to Example 5. The eluate of MAb I was adjusted from approximately pH 5 to pH 7 with Tris base (2 M) and filtered through a 0.22 micron Millipore Express Plus Stericup filter unit. The solution is referred to herein as the MAb I Protein A eluate.

Glass Omnifit Chromatography Columns (10 mm diameter, 100 mm length) were loaded with 250 mg of HD Nuchar activated carbon slurried in water to give a packed column volume of 1 mL. The columns were equilibrated with buffer solution (Tris-HCl buffer, 25 mM, pH 7). 3-layer, 0.26 mL Sartobind Q membrane devices were manufactured using commercially available Sartobind Q membrane disks (SIGMA-ALDRICH. St. Louis, Mo., USA) (0.26 mL, 3 sheets) and the device housing and process used to produce 0.2 mL ChromaSorb devices fabricated as described above in Example 7. 0.18 mL Acrodisc® Units with Mustang Q membrane were purchased from Thermo Fisher Scientific, Waltham, Mass., USA. These devices, along with 1 mL HiTrap Q FF prepacked column (GE Healthcare, Pittsburgh, Pa. USA) and 0.2 mL ChromaSorb device, were equilibrated with buffer solution (Tris-HCl buffer, 25 mM, pH 7).

Nine flow-through purification trains were assembled: a) activated carbon, b) ChromaSorb, c) activated carbon followed by ChromaSorb, d) Sartobind Q, e) activated carbon followed by Sartobind Q, f) Mustang Q, g) activated carbon followed by Mustang Q, h) HiTrap Q FF, i) activated carbon followed by HiTrap Q FF. 96 mL of the MAb I Protein A eluate was subsequently passed through each set up at a flow rate of 0.25 mL/min. After passing through the purification trains, the solutions were analyzed for host cell protein (HCP) and IgG concentration. HCP analysis was performed using a commercially available ELISA kit from Cygnus Technologies, Southport, N.C., USA, catalog number F550, following kit manufacturer's protocol. IgG concentration was measured using an Agilent HPLC system equipped with a Poros® A Protein A analytical column. Results are summarized in Table X.

The results show that the flow-through treatment of an affinity (Protein A) captured monoclonal antibody eluate with the combination of activated carbon with a variety of different anion exchange media was unexpectedly effective for the removal of impurities. The log reduction value (LRV) of host cell protein (HCP) was 0.91 for activated carbon alone. The different commercially available anion exchange media alone had very similar LRV of HCP ranging from 0.17 to 0.23. The combination of activated carbon followed by the different commercially available anion exchange media had much higher LRV of HCP ranging from 1.70 to 1.93. The combination of activated carbon followed by the different anion exchange media had excellent recoveries of the monoclonal antibody product ranging from 96% to 97%. The data demonstrates that activated carbon is unexpectedly effective for the purification of antibodies in combination with a variety of different commercially available anion exchange media including primary amines (ChomaSorb™) and quaternary amines (Sartobind Q. Mustang Q, HiTrap Q FF). The combination of activated carbon was highly effective in combination with commercially available anion exchange chemistries that were supported on a membrane (ChomaSorb, Sartobind Q, Mustang Q) and on a resin (HiTrap Q FF).

Example 14. Flow-Through Treatment of an Affinity Captured Eluate of MAb I with Activated Carbon Followed by Anion Exchange Media or with an Anion Exchange Media Followed by Activated Carbon The order of activated carbon and an anion exchange media for the flow-through removal of impurities from an affinity (Protein A) captured monoclonal antibody eluate was examined to demonstrate that the order of the two adsorbers unexpectedly influences their effectiveness. The experiment illustrates that the placement of activated carbon before the anion exchange media is important to maximize the ability of the combination of adsorbers to remove impurities from protein solutions.

A partially purified MAb I affinity (Protein A) captured eluate was prepared according to Example 5. The eluate of MAb I was adjusted from approximately pH 5 to pH 7 with Tris base (2 M) and filtered through a 0.22 micron Millipore Express Plus Stericup filter unit. The solution is referred to herein as the MAb I Protein A eluate.

Glass Omnifit Chromatography Columns (10 mm diameter, 100 mm length) were loaded with 250 mg of HD Nuchar activated carbon slurried in water to give a packed column volume of 1 mL. The columns were equilibrated with buffer solution (Tris-HCl buffer, 25 mM, pH 7). A 0.2 mL ChromaSorb membrane device fabricated as described above in Example 7 was also equilibrated with buffer solution (Tris-HCl buffer, 25 mM, pH 7). Two flow-through trains were assembled. The first had the activated carbon column followed by the ChromaSorb membrane device while the second had the reverse order with the ChromaSorb membrane device followed by the activated carbon column. 96 mL of the MAb I Protein A eluate was passed through each set up at a flow rate of 0.25 mL/min. After passing through the purification trains, the solutions were analyzed for host cell protein (HCP) and IgG concentration. HCP analysis was performed using a commercially available ELISA kit from Cygnus Technologies, Southport, N.C., USA, catalog number F550, following kit manufacturer's protocol. IgG concentration was measured using an Agilent HPLC system equipped with a Poros® A Protein A analytical column. Results are summarized in Table XI.

The results show the unexpected result that the order of the activated carbon and an anion exchange media (ChromaSorb) are important to the effectiveness of the flow-through purification of an affinity (Protein A) captured eluate. The log reduction value (LRV) of host cell protein (HCP) was 1.87 when activated carbon was placed in front of anion exchange media. The LRV of HCP was reduced to 1.38 when the anion exchange media was place in front of

TABLE X

| AEX Media | MAb I (mg/mL) | | Recovery of MAb I | | HCP (ng/mL) | | HCP (ppm) | | LRV of HCP | |
|---|---|---|---|---|---|---|---|---|---|---|
| | AEX Alone | AEX then A.C. | AEX alone | AEX then A.C. | AEX alone | AEX then A.C. | AEX alone | AEX then A.C. | AEX alone | AEX then A.C. |
| no AEX media | NA | 8.82 | NA | 96% | 5.701 | 738 | 618 | 84 | NA | 0.91 |
| ChromaSorb | 9.20 | 8.89 | 100% | 96% | 3,660 | 70 | 398 | 8 | 0.23 | 1.93 |
| Sartobind Q | 9.26 | 8.99 | 100% | 97% | 4,103 | 98 | 443 | 11 | 0.19 | 1.80 |
| Mustang Q | 9.17 | 8.86 | 99% | 96% | 4,001 | 120 | 436 | 14 | 0.19 | 1.70 |
| Q Fast Flow | 9.20 | 8.76 | 100% | 95% | 4,245 | 81 | 462 | 9 | 0.17 | 1.86 |

NA—Not Applicable the activated carbon. The order of the activated carbon and the anion exchange media had no influence on the recovery of the antibody, which was 97% for both orders of the adsorbers. The results reveal an important understanding that placing the activated carbon before the anion exchange media is important to maximize the effectiveness of the combination of two adsorbers to remove impurities from protein solutions.

TABLE XI

| Flow-through train | MAb I (mg/mL) | recovery of MAb I | HCP (ng/mL) | HCP (ppm) | LRV of HCP |
|---|---|---|---|---|---|
| untreated (control) | 9.24 | NA | 4,986 | 540 | NA |
| ChromaSorb followed by activated carbon | 8.95 | 97% | 202 | 23 | 1.38 |
| activated carbon followed by ChromaSorb | 8.95 | 97% | 65 | 7 | 1.87 |

NA—Not Applicable

Example 15. Flow-Through Treatment of a Non-Affinity Captured Eluate of MAb I with Activated Carbon Activated carbon was examined in a flow-through application for the removal of impurities from a non-affinity (cation exchange) captured monoclonal antibody eluate to demonstrate that activated carbon provides a unique and unexpectedly effective method for the removal of impurities. Relative to an affinity (Protein A) captured eluate the non-affinity (cation exchange) captured eluate contains different types of impurities at significantly higher levels. The application of activated carbon for the purification of a non-affinity captured eluate demonstrates that this method is general and can be applied to the purification of a variety of different protein solutions.

A partially purified MAb I CEX eluate was prepared as described in Example 6. The eluate was diluted by a factor of 4 with a buffer solution (Tris-HCl buffer, 25 mM, pH 7). The diluted eluate of MAb I was adjusted from approximately pH 6 to pH 7 with Tris base (2 M) and filtered through a 0.22 micron Millipore Express Plus Stericup filter unit. The solution is referred to herein as the MAb I CEX eluate.

Glass Omnifit Chromatography Column (10 mm diameter, 100 mm length) was loaded with 250 mg of HD Nuchar activated carbon slurried in water to give a packed column volume of 1 mL. The column was equilibrated with a buffer solution (Tris-HCl buffer, 25 mM, pH 7).

70 mL of the MAb I CEX eluate was then passed through the column of activated carbon at a flow rate of 0.25 mL/min. Seven 10 mL fractions of the eluate were collected. Pooled samples of all seven as well as selected individual fractions were analyzed for host cell protein (HCP) and IgG concentration. HCP analysis was performed using a commercially available ELISA kit from Cygnus Technologies, Southport, N.C. USA, catalog number F550, following kit manufacturer's protocol. IgG concentration was measured using an Agilent HPLC system equipped with a Poros® A Protein A analytical column. Results are summarized in Table XI.

As depicted in FIG. 16 and summarized in Table XII below, the results show that flow-through purification with activated carbon was unexpectedly effective for the removal of impurities from a non-affinity (cation exchange) captured monoclonal antibody eluate. Non-affinity (cation exchange) based capture media binds more impurities along with the monoclonal antibody than the more specific affinity (Protein A) based capture media. Therefore non-affinity captured eluate contains different types of impurities at significantly higher levels. Activated carbon provided a log reduction value (LRV) of host cell protein (HCP) of 0.76 and had 89% recovery of the monoclonal antibody product. These results suggest that activated carbon can be used to remove impurities from a variety of different protein solutions.

TABLE XII

| Flow-through train | MAb I (mg/mL) | recovery of MAb I | HCP (ng/mL) | HCP (ppm) | LRV of HCP |
|---|---|---|---|---|---|
| untreated (control) | 3.13 | NA | 66,269 | 21,172 | NA |
| activated carbon column | 2.79 | 89% | 10,343 | 3,707 | 0.76 |

NA—Not Applicable

Example 16. Flow-Through Purification of an Affinity Captured Eluate of MAb I with Activated Carbon Packed Column and an Activated Carbon-Cellulose Device Activated carbon packed in a column or blended into a cellulose sheet was examined in a flow-through application for the removal of impurities from an affinity (Protein A) captured monoclonal antibody eluate to demonstrate that the activated carbon provides a unique and unexpectedly effective method for the removal of impurities in different formats.

A partially purified MAb I affinity (Protein A) captured eluate was prepared according to Example 5. The eluate of MAb I was adjusted from approximately pH 5 to pH 7 with Tris base (2 M) and filtered through a 0.22 micron Millipore Express Plus Stericup filter unit. The solution is referred to herein as the MAb I Protein A eluate.

Glass Omnifit Chromatography Columns (15 mm diameter, 100 mm length) were loaded with 600 mg of HD Nuchar activated carbon slurried in water to give a packed column volume of 2.4 mL. Activated carbon-impregnated cellulose sheet media, commercially available in a Millistak+ Pod CR device from Millipore Corporation, Billerica, Mass., was placed in an overmolded polypropylene syringe device, internal filtration area 25 mm, 4.6 mL bed volume, equipped with Luer connectors for inlet and outlet.

The column and the activated carbon-cellulose device were equilibrated with buffer solution (Tris-HCl buffer, 25 mM, pH 7). Two flow-through trains were assembled. The first had the activated carbon column while the second had the activated carbon-cellulose device. 315 mL, of the MAb I Protein A eluate was subsequently passed through each set up, at a flow rate of 0.75 mL/min. After passing through the purification trains, the solutions were analyzed for host cell protein (HCP) and IgG concentration. HCP analysis was performed using a commercially available ELISA kit from Cygnus Technologies, Southport, N.C., USA (catalog number F550), following kit manufacturer's protocol. IgG concentration was measured using an Agilent HPLC system equipped with a Poros® A Protein A analytical column. Results are summarized in Table XIII.

The results show that the flow-through purification with activated carbon was unexpectedly effective for the removal of impurities from an affinity (Protein A) captured monoclonal antibody eluate when packed into column or blended into a cellulose sheet. Activated carbon packed into a column or blended into a cellulose sheet both gave very similar log reduction values (LRV) of host cell protein (HCP) of 0.95 and 0.97 respectively. They also had very similar recoveries of the monoclonal antibody product of 91% for the column and 87% for the cellulose sheet. These results suggest that activated carbon can be used effectively for the removal of impurities from protein solutions when blended into a cellulose sheet.

TABLE XIII

| Flow-through train | MAb I (mg/mL) | recovery of MAb I | HCP (ng/mL) | HCP (ppm) | LRV of HCP |
|---|---|---|---|---|---|
| untreated (control) | 9.79 | NA | 6,229 | 642 | NA |
| HD Nuchar activated carbon Column | 8.92 | 91% | 682 | 76 | 0.95 |
| activated carbon-cellulose device | 8.53 | 87% | 620 | 73 | 0.97 |

NA—Not Applicable

Example 17. Flow-Through Purification of an Affinity Captured Eluate of MAb I with Two Other Types of Activated Carbon Two other types of commercially available activated carbon were examined in a flow-through application for the removal of impurities from an affinity (Protein A) captured monoclonal antibody eluate to demonstrate the unexpected result that a variety of different activated carbons can be used for the removal of impurities from protein solutions.

A partially purified MAb I affinity (Protein A) captured eluate was prepared according to Example 5. The eluate of MAb I was adjusted from approximately pH 5 to pH 7 with Tris base (2 M) and filtered through a 0.22 micron Millipore Express Plus Stericup filter unit. The solution is referred to herein as the MAb I Protein A eluate.

Glass Omnifit Chromatography Columns (5 mm diameter, 100 mm length) were loaded with 125 mg of Chemviron Pulsorb PGC activated carbon (Chemviron Carbon, Feluy, Belgium) or Norit A Supra USP activated carbon (Norit Americas Inc., Marshall, Tex. USA) slurried in water to give a packed column volume of 0.24 mL. The columns were equilibrated with buffer solution (Tris-HCl buffer, 25 mM, pH 7). Two flow-through trains were assembled. The first had the Chemviron Pulsorb PGC activated carbon column while the second had the Norit A Supra USP activated carbon column. 96 mL of the MAb I Protein A eluate was passed through each set up at a flow rate of 0.25 mL/min. After passing through the purification trains, the solutions were analyzed for host cell protein (HCP) and IgG concentration. HCP analysis was performed using a commercially available ELISA kit from Cygnus Technologies, Southport, N.C., USA (catalog number F550), following the kit manufacturer's protocol. IgG concentration was measured using an Agilent HPLC system equipped with a Poros® A Protein A analytical column. Results are summarized in Table XIV.

The results show that the flow-through purification with two other types of activated carbon were unexpectedly effective for the removal of impurities from an affinity (Protein A) captured monoclonal antibody eluate. The Chemviron Pulsorb PSG and Norit A Supra USP both removed impurities with log reduction values (LRV) of host cell protein (HCP) of 0.40 and 0.48 respectively. They also had excellent recoveries of the monoclonal antibody product of 100% for Chemviron Pulsorb PSG and 100% for Norit A Supra USP. These results suggest that several different types of activated carbon can be used for the removal of impurities from protein solutions.

TABLE XIV

| Flow-through train | MAb I (mg/mL) | recovery of MAb | HCP (ng/mL) | HCP (ppm) | LRV of HCP |
|---|---|---|---|---|---|
| untreated (control) | 7.15 | NA | 1026 | 144 | NA |
| Chemviron Pulsorb PGC | 7.18 | 100% | 409 | 57 | 0.40 |
| Norit A Supra USP | 7.17 | 100% | 341 | 48 | 0.48 |

NA—Not Applicable

Example 18. Flow-Through Purification of an Affinity Captured Eluate of MAb I in the Presence of Different Buffer Salts Activated carbon was examined in a flow-through application for the removal of impurities from an affinity (Protein A) captured monoclonal antibody eluate with various different salts added to demonstrate that activated carbon provides a unique and unexpectedly effective method for the removal of impurities in the presence of many different salts. The investigation illustrates that this method is general and can be applied to the purification of proteins in a variety of different buffer salts.

A partially purified MAb I affinity (Protein A) captured eluate was prepared according to Example 5. The eluate of MAb I was adjusted from approximately pH 5 to pH 7 with Tris base (2 M) and filtered through a 0.22 micron Millipore Express Plus Stericup filter unit. The solution is referred to herein as the MAb I Protein A eluate.

To a 50 mL portion of the MAb I Protein A eluate, 10 mL aqueous solution containing of 300 mM of various salts was added, where the salts were ammonium sulfate, ethylenediaminetetraacetic acid disodium salt dehydrate (EDTA), 2-(N-morpholino)ethanesulfonic acid (MES), sodium chloride, Trisodium citrate dehydrate, sodium phosphate dibasic heptahydrate, and Trizma® Pre-set crystals, pH 7.0 (Tris-HCl).

A solution diluted with 10 mL water was used as a control. The pH of the salt spiked Protein A eluate were adjusted back to 7 with 2 M Tris base or 3 M acetic acid. The solution is referred to herein as the salt spiked MAb I Protein A eluate.

Glass Omnifit Chromatography Columns (5 mm diameter, 100 mm length) were loaded with 125 mg of HD Nuchar activated carbon slurried in water to give a packed column volume of 0.5 mL. The columns were equilibrated with buffer solution (Tris-HCl buffer, 25 mM, pH 7). 40 mL of the salt spiked MAb I Protein A eluate was then passed through the columns of activated carbon at a flow rate of 0.125 mL/min. After passing through the columns, the solutions were analyzed for host cell protein (HCP) and IgG concentration. HCP analysis was performed using a commercially available ELISA kit from Cygnus Technologies. Southport, N.C., USA (catalog number F550), following the kit manufacturer's protocol. IgG concentration was measured using an Agilent HPLC system equipped with a Poros® A Protein A analytical column. Results are summarized in Table XV.

The results show that the flow-through purification of an affinity (Protein A) captured monoclonal antibody eluate with activated carbon was unexpectedly effective for the removal of impurities in the presence of a variety of different salt additives. The activated carbon removed impurities in the presence of all the added salts with log reduction values (LRV) of host cell protein (HCP) ranging from 0.63 to 1.00. They also had excellent recoveries of the monoclonal antibody product ranging from 92% to 96%. These results suggest that activated carbon can be used for the removal of impurities from protein solutions in a variety of different salt buffers.

TABLE XV

| spiked salt | MAb I (mg/mL) before A.C. | MAb I (mg/mL) after A.C. | Recovery of MAb I | HCP (ng/mL) before A.C. | HCP (ng/mL) after A.C. | HCP (ppm) before A.C. | HCP (ppm) after A.C. | LRV of HCP |
|---|---|---|---|---|---|---|---|---|
| water only (control) | 7.33 | 6.86 | 94% | 987 | 76 | 135 | 11 | 1.08 |
| Tris | 6.99 | 6.68 | 96% | 1,194 | 119 | 171 | 18 | 0.98 |
| sodium chloride | 6.58 | 6.33 | 96% | 1,151 | 111 | 175 | 17 | 1.00 |
| ammonium sulfate | 6.93 | 6.66 | 96% | 1,359 | 177 | 196 | 27 | 0.87 |
| disodium phosphate | 6.92 | 6.59 | 95% | 1,293 | 153 | 187 | 23 | 0.90 |
| sodium citrate | 6.53 | 6.03 | 92% | 1,351 | 241 | 207 | 40 | 0.71 |
| EDTA | 6.71 | 6.39 | 95% | 1,304 | 293 | 194 | 46 | 0.63 |
| MES | 6.90 | 6.54 | 94% | 1,110 | 132 | 161 | 20 | 0.90 |

Example 19. Flow-Through Purification of Protein A Eluate at pH 5 and pH 7

Activated carbon was examined in a flow-through application for the removal of impurities from an affinity (Protein A) captured monoclonal antibody eluate at two different pH conditions to demonstrate that activated carbon provides a unique and unexpectedly effective method for the flow-through removal of impurities at different solution pH conditions. The investigation illustrates that this method is general and can be applied to the purification of proteins under different pH conditions.

A partially purified MAb I affinity (Protein A) captured eluate was prepared according to Example 5. The solution is referred to herein as the pH 5 MAb I Protein A eluate.

A portion of the eluate of MAb I prepared according to Example 5 was adjusted from approximately pH 5 to pH 7 with Tris base (2 M) and filtered through a 0.22 micron Millipore Express Plus Stericup filter unit. The solution is referred to herein as the pH 7 MAb I Protein A eluate.

Glass Omnifit Chromatography Columns (15 mm diameter, 100 mm length) were loaded with 1.25 g of HD Nuchar activated carbon slurried in water to give a packed column volume of 5 mL. The columns were equilibrated with buffer solution (Tris-HCl buffer, 25 mM, pH 7). Then 500 mL of the pH 5 MAb I Protein A eluate or the pH 7 MAb I Protein A eluate was passed through the activated column at a flow rate of 1.25 ml/min. After passing through the purification trains, the solutions were analyzed for host cell protein (HCP) and IgG concentration. HCP analysis was performed using a commercially available ELISA kit from Cygnus Technologies, Southport, N.C., USA (catalog number F550), following the kit manufacturer's instructions. IgG concentration was measured using an Agilent HPLC system equipped with a Poros® A Protein A analytical column. Results are summarized in Table XVI.

The results show that the flow-through purification of an affinity (Protein A) captured monoclonal antibody eluate with activated carbon was unexpectedly effective for the removal of impurities at both pH 5 and pH 7. The activated carbon removed impurities with log reduction values (LRV) of host cell protein (HCP) of 0.85 at pH 5 and 1.15 at pH 7. Activated carbon also had excellent recoveries of the monoclonal antibody with 97% at pH 5 and 101% at pH 7. These results suggest that activated carbon can be used for the removal of impurities for protein solutions at different pH conditions.

TABLE XVI

| pH | MAb I (mg/mL) before A.C. | MAb I (mg/mL) after A.C. | Recovery of MAb I | HCP (ng/mL) before A.C. | HCP (ng/mL) after A.C. | HCP (ppm) before A.C. | HCP (ppm) after A.C. | LRV of HCP |
|---|---|---|---|---|---|---|---|---|
| 5 | 9.22 | 8.98 | 97% | 3,429 | 486 | 371 | 54 | 0.85 |
| 7 | 8.61 | 8.68 | 101% | 1,774 | 124 | 206 | 14 | 1.15 |

Example 20. Flow-Through Purification of a Protein A Eluate Prepared Using Continuous Chromatography This representative experiment demonstrates that Activated Carbon and an anion-exchange chromatography device can be used to purify a Protein A eluate obtained using Continuous multicolumn chromatography (CMC).

In this example, a monoclonal antibody (MAb II) is purified using a three column continuous multicolumn chromatography (CMC) method using Prosep® Ultra Plus Protein A resin, as described in co-pending European Patent Application No. EPI2002828.7, incorporated by reference herein. The Protein A eluate is pooled and processed through an activated carbon device followed by an anion exchange chromatography device (i.e., ChromaSorb™), as described in Example 12.

Figure 18:
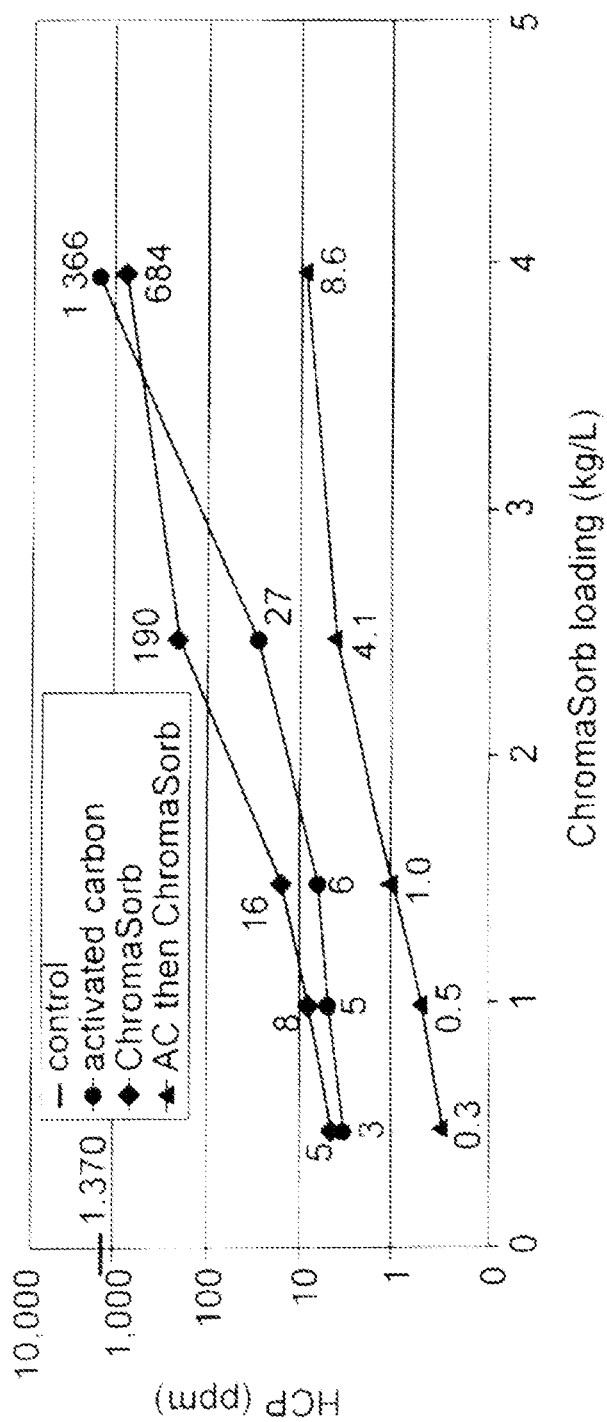
FIG. 18 is a graph demonstrating the results of an experiment to measure the concentration of HCP relative to that of the product (i.e., a monoclonal antibody, MAb II) in ppm for the individual fractions of a monoclonal antibody solution, where the solution is captured from clarified cell culture using a three-column continuous multi-chromatography chromatography (CMC) system equipped with Protein A columns, and subsequently purified with of HD Nuchar activated carbon packed into a column followed by an anion exchange chromatography device (e.g., ChromaSorb™). The X-axis of the graph depicts the end point of fraction collection, measured in the weight of antibody loaded per unit volume of the anion exchange device (kg/L). The Y-axis of the graph depicts the concentration of HCP relative to that of the product (i.e., a monoclonal antibody) in ppm for the individual fractions. The graph demonstrates that while both activated carbon and ChromaSorb™ remove a significant portion of HCP when used alone, when used in combination, they increase the purity of the starting solution from 1,370 ppm HCP to under 10 ppm.

As demonstrated in FIG. 18, successful purification of the monoclonal antibody is obtained, as measured by the reduction of HCP concentration below 10 ppm, when a combination of activated carbon and an anion exchange chromatography device are used.

Example 21. Connecting Several Flow-Through Impurity Removal Steps

In this representative experiment, the feasibility of connecting several impurity removal steps in flow-through mode to operate as a single unit operation or process step is demonstrated, while meeting product purity and yield targets.

In this example, individual devices, namely, an activated carbon device, an anion exchange chromatography device (i.e., ChromaSorb™), a cation exchange chromatography device and a virus filtration device (i.e., Viresolve® Pro) are connected to operate in a flow-through mode. Further, an in-line static mixer and/or a surge tank are positioned between the anion exchange chromatography and the cation exchange chromatography devices, in order to achieve a pH change. Lastly, an optional depth filter is positioned upstream of the activated carbon device, in case the sample being purified is turbid.

Figure 19:
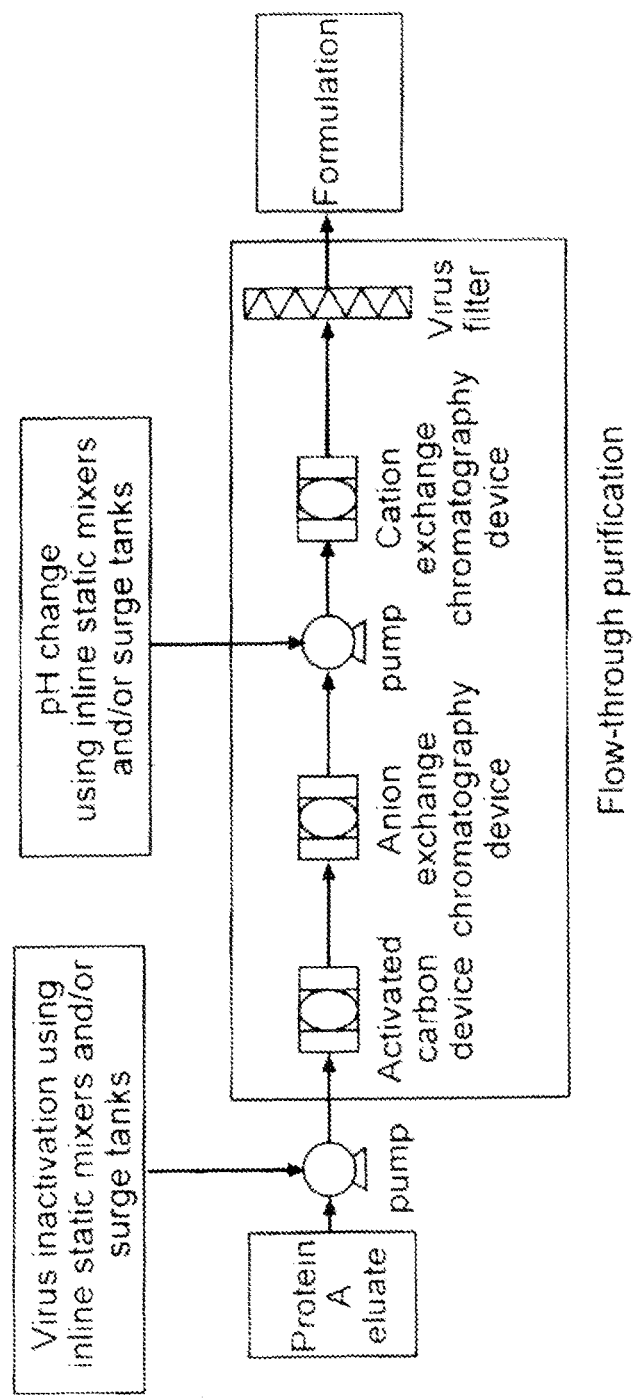
FIG. 19 demonstrates a schematic of the connected flow-through purification process step, as described herein. An activated carbon containing device is connected directly to an anion-exchange device. The effluent from the anion-exchange device passes through a static mixer, where an aqueous acid is added to reduce pH, and then goes through a cation-exchange flow-through device and a virus filter.

FIG. 19 depicts a schematic representation of the experimental set up to perform a flow-through purification process step, which includes the following described devices.

Additionally, the necessary pumps, valves, sensors etc. may also be included in such a set up.

All devices are individually wetted at a different station, and then assembled. The devices are wetted and pre-treated according to the manufacturer's protocol. Briefly, the depth filter (A1HC grade) is flushed with 100 L/m² of water followed by 5 volumes of equilibration buffer 1 (EB1; Protein A elution buffer adjusted to pH 7.5 with 1 M Tris-base, pH 11). 2.5 mL of activated carbon is packed into a 2.5 cm Omnifit column as described in Example 12, to produce antibody loading of 0.55 kg/L. The column is flushed with 10 CV water, and then equilibrated with EB1 until the pH is stabilized to pH 7.5. Two ChromaSorb devices (0.2 and 0.12 mL) are connected in series to get a loading of 4.3 kg/L. The devices are wetted with water at 12.5 CV/min for at least 10 min, followed by 5 DV (Device Volumes) EB1. A disposable helical static mixer (Koflo Corporation, Cary, Ill.) with 12 elements is used to perform in-line pH adjustments. Two 1.2 mL cation-exchange flow-through devices for aggregate removal are connected in parallel to remove aggregates. The MAb loading on the CEX devices is about 570 mg/mL. These devices are wetted with 10 DV water, followed by 5 DV equilibration buffer 2 (EB2; EB1 Adjusted to pH 5.0 using 1 M acetic acid). The devices are further treated with 5 DV (device volumes) of EB2+1 M NaCl, and then equilibrated with 5 DV EB2. A 3.1 cm² ViResolve® Pro device is wetted with water pressurized at 30 psi for at least 10 min. The flow rate is then monitored every minute until the flow rate remains constant for 3 consecutive minutes. After all the devices are wetted and equilibrated, they are connected to as shown in FIG. 19. EB1 is run through the entire system until all pressure readings, and pH readings are stabilized. Following equilibration, the feed is passed through the flow-through train. During the run, samples are collected before the surge tank and after Viresolve® Pro to monitor IgG concentration and impurity levels (HCP, DNA, leached PrA and aggregates). After the feed is processed, the system is flushed with 3 dead volumes of EB1 to recover protein in the devices and in the plumbing.

The feed for the connected flow-through process is protein A eluate of MAb II, produced in a batch protein A process. The natural level of aggregates in this MAb does not exceed 1%, so a special procedure was developed to increase the level of aggregates. The solution pH is raised to 11 with aqueous NaOH, with gentle stirring, and held for 1 hour. The pH is then lowered slowly to pH 5 with aqueous HCl under gentle stirring. The pH cycle is repeated 4 more times. The final level of aggregates is about 5%, mostly consisting of MAb dimers and trimers as measured by SEC. The feed is then dialyzed into Tris-HCl buffer, pH 7.5, conductivity about 3 mS/cm.

The amount of MAb feed processed for this run is 102 mL of 13.5 mg/mL MAb at a flow rate of 0.6 mL/min.

Figure 20:
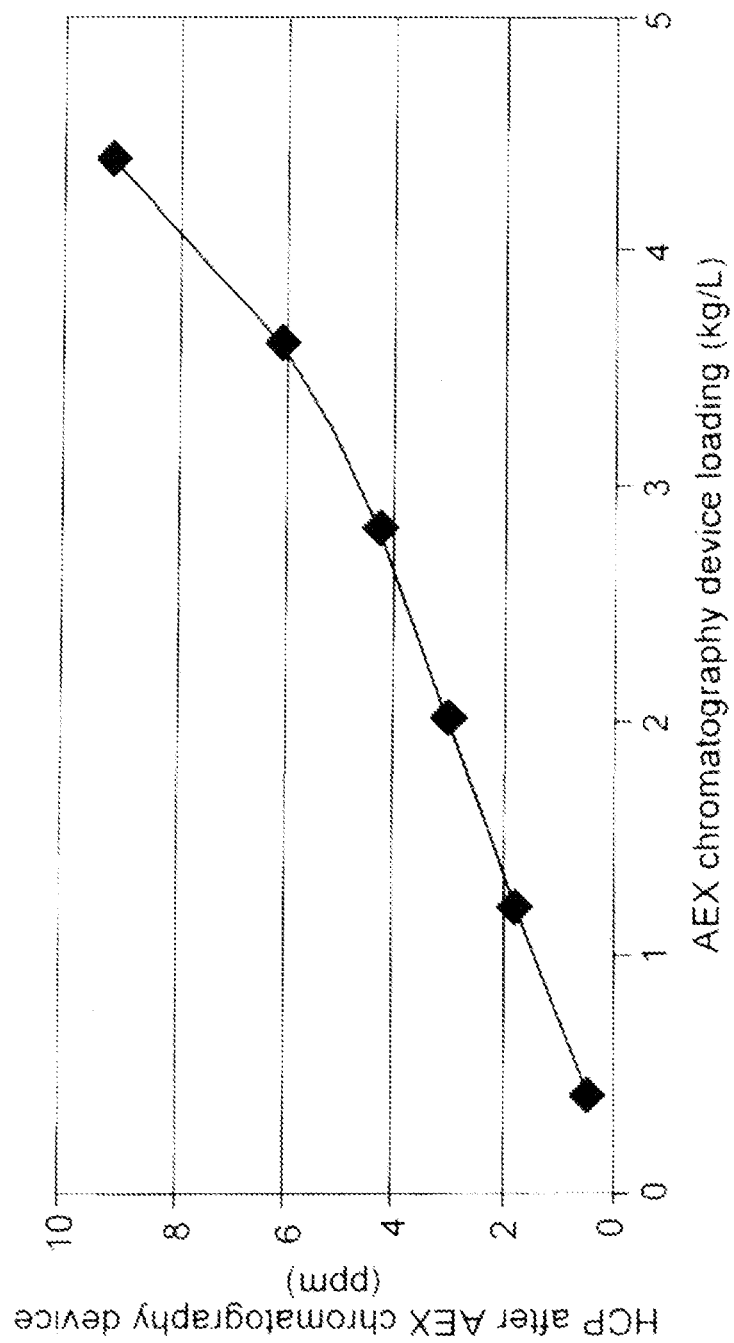
FIG. 20 is a graph depicting the results of an experiment to measure HCP breakthrough after an anion exchange chromatography device (i.e., ChromaSorb™). The Y-axis denotes HCP concentration (ppm) and the X-axis denotes the AEX loading (kg/L).
Figure 21:
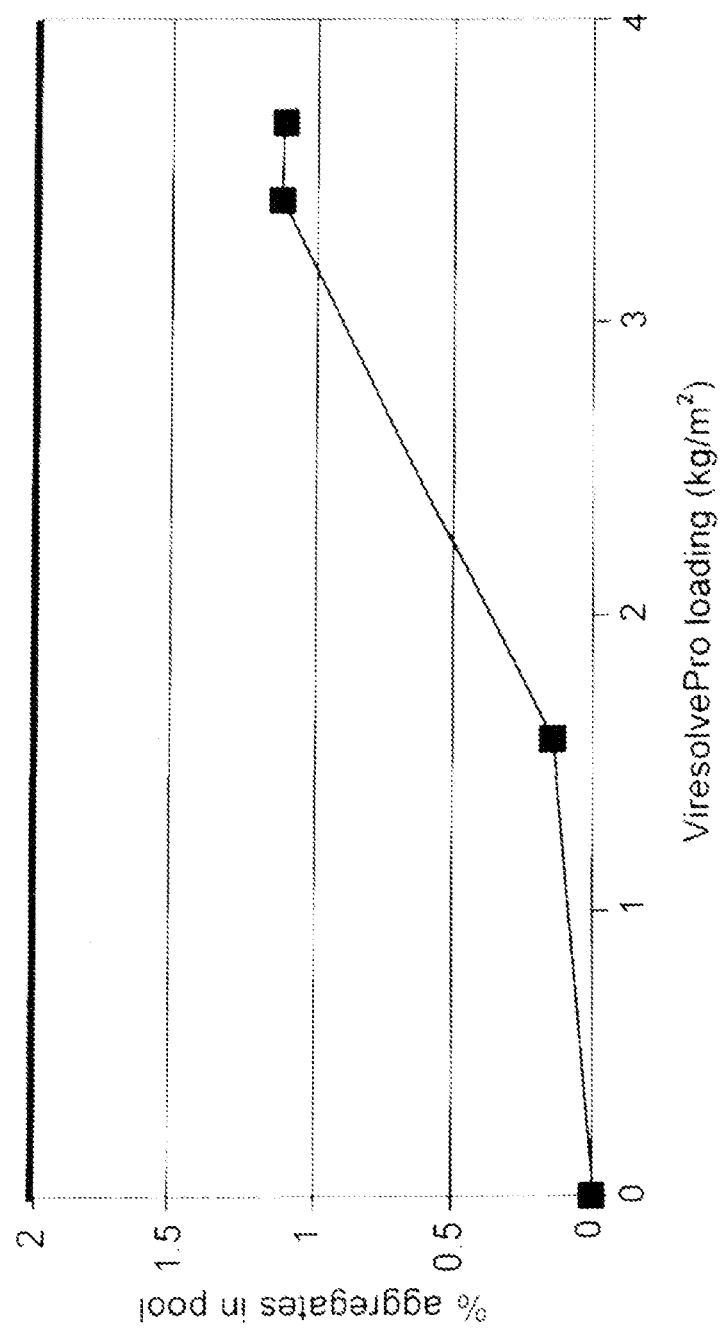
FIG. 21 is a graph depicting the results of an experiment to measure removal of MAb aggregates as a function of loading of the virus filtration device in the flow-through purification process step. The X-axis denotes the virus filtration loading (kg/m$^2$) and the Y-axis denotes percentage of MAb aggregates in the sample after virus filtration.

The HCP breakthrough as a function of time after ChromaSorb™ is below the upper limit of 10 ppm (FIG. 20). The aggregates are reduced from 5% to 1.1% by the CEX device (FIG. 21). The MAb II yield of the connected process is 92%. The throughput on Viresolve® Pro device is >3.7 kg/m².

Accordingly, the foregoing Example demonstrates that several devices can be connected to operate in a flow-through mode successfully, thereby to achieve the desired product purity and yield targets.

Example 22. Connecting Flow-Through Purification Process Step with Continuous Bind and Elute Chromatography Capture Step In this representative experiment, a flow-through purification process, as described herein, was directly linked to a continuous bind and elute chromatography capture process, which precedes the flow-through purification.

In this example, a CHO-based monoclonal antibody (MAbII) is produced in a fed-batch bioreactor. A total of 7 L of cell culture is contacted with a solution of stimulus responsive polymer to make a final stimulus responsive polymer concentration of 0.2% v/v. The cell culture is allowed to mix for approximately 10 minutes. 175 mL of 2 M $K_2HPO_4$ solution is added and allowed to mix for an additional 10 minutes. The pH is then raised to 7.0 with 2 M tris base and allowed to mix for 15 minutes. The solution is then centrifuged in 2 L aliquots at 4,500×g for 10 minutes and the supernatant is decanted and retained. The solids are disposed off. The cell culture supernatant is pooled and then mixed with 5 M NaCl at a 1:10 ratio in a batch mode with continuous stirring. The final conductivity of the solution is measured at this point and is at 55±5 mS/cm. The resulting higher NaCl concentration solution is sterile filtered through a 0.22 m Express filter. The sterile filtered solution is the loading material for the Protein A chromatography.

The protein A capture step consists of two protein A columns running with a method on a modified Akta Explorer 100. The Protein A columns have 10 mL of ProSep® Ultra Plus protein A media packed into 1.6 cm ID Vantage-L (EMD Millipore) chromatography columns to bed heights of 10.25 and 10.85 cm. The columns are equilibrated with 1×TBS, 0.5 M NaCl for 5 column volumes, CVs (all column volumes are based on the smallest column). Throughout the run, the loading flow rate is set so as to have a loading residence time of about one minute. During the initial loading, both columns are placed in series, where the effluent of the primary column is loaded directly onto the secondary column until a specific load volume is reached. After a specific loading volume is passed over the columns, the feed is stopped and two CVs of the equilibration buffer is passed through the primary column to the secondary column. The primary column is then positioned to undergo washing, elution, cleaning and reequilibration, while the secondary column is loaded as the primary column. Following the reequilibration of the first column, that column is then moved to the secondary position to reside in series with the now primary column. This series of events is repeated with each column taking the primary position after the original primary position column is loaded to a set volume. Each column is loaded a total of seven times. The elutions from each column are collected with a fraction collector, using a UV trigger to control the start time of the elution and collected to a constant volume of approximately 3.5 CVs.

The flow-through purification train consists of six main devices: optional depth filter (for precipitate removal after pH adjustment to pH 7.5); activated carbon; ChromaSorb™; static mixer and/or surge tank for in-line pH adjustment; cation-exchange flow-through device for aggregate removal (CEX device); and virus filtration device (i.e., Viresolve® Pro).

FIG. 19 illustrates the order in which these devices are connected.

All devices are individually wetted at a different station, and then assembled as shown in FIG. 19. The devices are wetted and pre-treated according to the manufacturer's protocol or as described earlier. Briefly, the depth filter (A1HC) is flushed with 100 L/m² of water followed by 5 volumes of equilibration buffer 1 (EB1; PrA elution buffer adjusted to pH 7.5 with 1 M Tris-base, pH 11). 10 mL of activated carbon is packed into a 2.5 cm Omnitfit column as described in Example 12. The column is flushed with 10 CV water, and then equilibrated with EB1 until the pH is stabilized to pH 7.5. 1.2 mL of ChromaSorb membrane (7 layers) is stacked into a 47 mm diameter Swinex device. The device is wetted with water at 12.5 CV/min for at least 10 min, followed by 5 device volumes (DVs) of EB1. A disposable helical static mixer (Koflo Corporation, Cary, Ill.) with 12 elements is used to perform in-line pH adjustments. A 3-layer cation-exchange chromatography device (0.12 mL membrane volume) is wetted with 10 DVs water, followed by 5 DVs of equilibration buffer 2 (EB2: EB1 adjusted to pH 5.0 using 1 M acetic acid). The device is further treated with 5 DVs of EB2+1 M NaCl, and then equilibrated with 5 DV EB2. A 3.1 cm2 Viresolve® Pro virus filtration device is wetted with water pressurized at 30 psi for at least 10 minutes. The flow rate is then monitored every minute until the flow rate remains constant for 3 consecutive minutes. After all the devices are wetted and equilibrated, they are connected as shown in FIG. 19. EB1 is run through the entire system until all pressure readings, and pH readings are stabilized. Following equilibration, feed (PrA elution adjusted to pH 7.5) is passed through the Flow-Through Purification train. During the run, samples are collected before the surge tank and after Viresolve® Pro to monitor IgG concentration and impurity levels (HCP, DNA, leached PrA and aggregates). After the feed is processed, the system is flushed with 3 dead volumes of EB1 to recover protein in the devices and in the plumbing.

Figure 22:
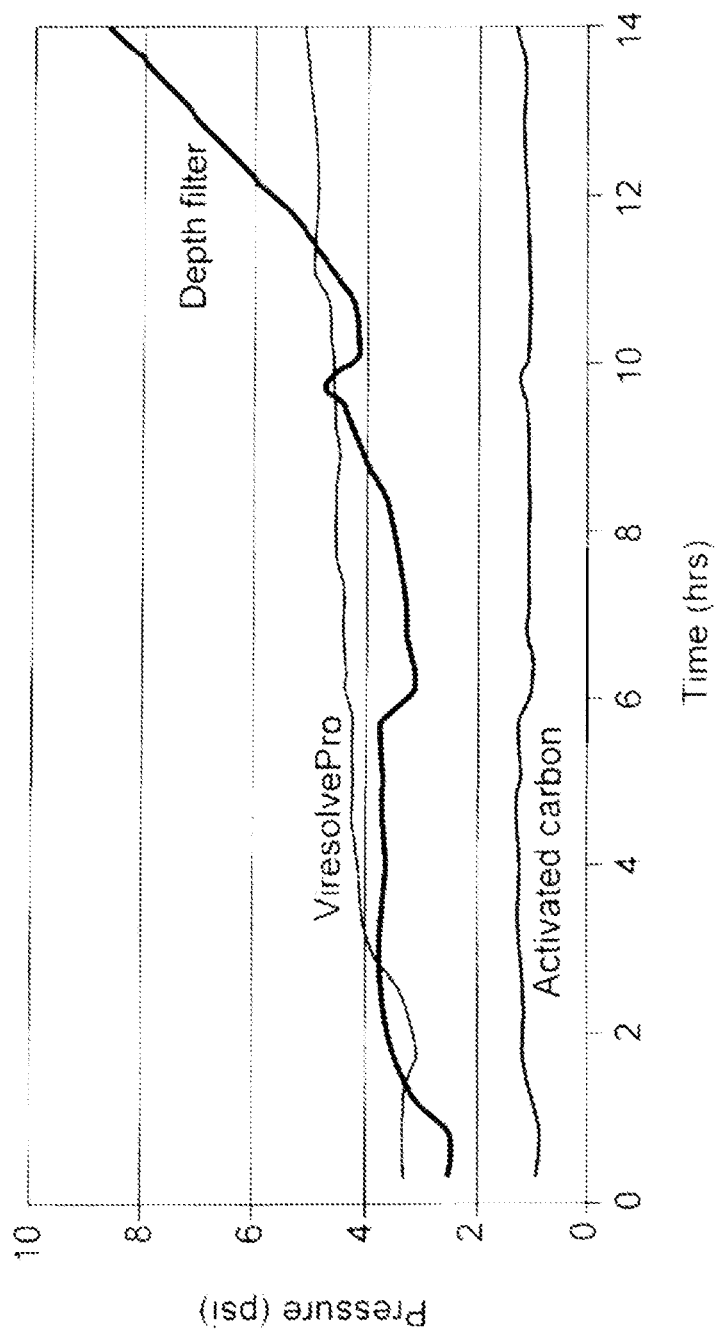
FIG. 22 is a graph depicting the results of an experiment to measure pressure profiles after depth filter, activated carbon and virus filtration. The Y-axis denotes pressure (psi) and the X-axis denotes time in hours.

FIG. 22 shows the pressure readings before depth filter, activated carbon, and ViresolvePro. The pressure on the depth filter remains unchanged for most part of the run, but rises towards the end suggesting some precipitation of the Protein A elution feed fractions towards the end of the Protein A runs. The activated carbon column remains fairly protected from any precipitate due the depth filter upstream of the activated carbon. The ViresolvePro pressure rises slowly with time, but is well below the operating maximum limit (50 psi).

The final HCP in the ViresolvePro pool is <1 ppm (Table XVI). The average leached Protein A in the elution fractions is 32 ppm. The leached Protein A in the Viresolve® Pro pool is 4 ppm. The aggregates are reduced from 1% to 0.4%. Table XVII below depicts the results of an experiment to investigate flow-through purification performance when connected with a continuous bind and elute chromatography process step.

TABLE XVII

| | |
|---|---|
| Flow-Through Purification Yield (%) | 97.8% |
| Average HCP from all PrA elutions to ViresolvePro pool (ppm) | 172 → 1.75 |
| Aggregates in ViresolvePro pool (%) | 1 → 0.4% |
| Leached PrA in ViresolvePro pool (ppm) | 32 → 4 |
| ViresolvePro throughput (kg/m²) | >6.1 |
| Dilution factor post-Protein A | 1.15x |

Example 23. Removal of a Cell Culture Component Impurity Using Activated Carbon

In this representative experiment, it is demonstrated that potential impurities from cell culture that may persist through the Protein A affinity capture step are removed by activated carbon.

A common component of the cell culture media. Insulin, a growth stimulator of mammalian cells, is typically present in the cell culture media in concentrations 1-20 mg/L. Recombinant Human Insulin (Incelligent AF from EMD Millipore Corp.) is dissolved in 50 mM Tris pH 7.0 buffer at 1 mg/mL, monoclonal antibody MAb II was added to concentration 7 g/L. A glass Omnifit column is packed with HD Nuchar activated carbon. The solution is flowed through the column at a constant rate of 0.25 CV/min, to a total MAb II loading of 1 kg/L. The flow-through pool is analyzed for insulin and antibody concentration. For analysis, an Agilent HPLC system equipped with HC18 column (Cadena) is used; solvent A: 0.1% TFA in water; solvent B 0.1% TFA in Acetonitrile; optimized gradient of 5%-30% B over 15 minutes was used to detect insulin by UV A214 absorbance. First, a calibration curve is created using standard solutions of insulin in the presence of antibody. No insulin is detected in the effluent from the activated carbon column, indicating that the activated carbon has capacity for Insulin in the presence of MAb, in excess of 240 mg/g.

Example 24. Flow-Through Removal of Impurities from a Turbid Solution of Affinity Captured Eluate of MAb II with Activated Carbon Cellulose Media In this representative experiment, it was demonstrated that activated carbon is unique and unexpectedly effective for the removal of HCP derived from microbial feeds. A solution of *E. coli* lysate was spiked with mAb monoclonal antibody at 1.5 mg/mL. The spiked feed was treated with activated carbon packed in a column under flow-through conditions.

Cells from a culture of *E. coli* were recovered by centrifugation. The supernatant was decanted off and the remaining cell pellet was suspended in a lysis buffer (25 mM Tris, 0.1 mM EDTA at pH 7) by vigorous shaking and stirring. Then a 0.4 mL portion of a stock solution of 100 mM PMSF in ethanol was added. The suspension was split into fractions (~100 mL each) and subjected to sonication with 3 sec on and 4 sec off for 5 min. Following sonication the material was pooled and stored at −80 degrees C. for 48 hour. Then the solution was thawed and centrifuged at 4,500×g for 2 hours to remove the lysed cells. The supernatant was filtered with a Stericup-HV 0.45 μm Durapore membrane (1000 mL, catalogue number: SCHVU11RE, Millipore Corp. Billerica, Mass., 01821, USA). Then it was filtered through Stericup-GP 0.22 μm Millipore Express PLUS membrane (1000 mL, catalogue number: SCGPU11RE, Millipore Corp. Billerica, Mass., 01821, USA). The filtered lysate was than combined with 7.5 mL of 10 mg/mL of a mAb solution to give a solution spiked with 1.5 mL of the mAb. The pH of the solution was measure to be 7.7.

A glass Omnifit Chromatography Column (10 mm diameter, 100 mm length) was loaded with 250 mg of Nuchar HD activated carbon (MeadWestVaco Corporation, Richmond, Va., USA) slurried in water to give a packed column volume of 1 mL. The column was equilibrated with 25 mM Tris buffer at pH 7. Then 42 mL of the mAb spiked E. coli lysate was passed through the activated carbon column at a flow rate of 0.25 mL/min giving a residence time of 4 minutes in the activated carbon. The control and a pool sample were submitted for analysis for host cell protein (HCP) and IgG concentration.

HCP analysis was performed using a commercially available E. Coli HCP ELISA kit from Cygnus Technologies, Southport. N.C., USA (catalog number F410), following the kit manufacturer's instructions. IgG concentration was measured using an Agilent HPLC system equipped with a Poros® A Protein A analytical column. The results show that activated carbon was unexpectedly effective for the selective removal of HCP derived from a microbial feed. The concentration of HCP in the lysate was reduced from 206,000 ng/mL (133,00 ppm) to 119,000 ng/mL (77,800 ppm) while the recovery of the mAb was 99% starting at a concentration of 1.55 g/L and recovered at 1.53 g/L. This example demonstrates that activated carbon can be used to remove HCP from non-mammalian cells.

Example 25. Removal of Impurities from a Turbid Solution of Affinity Captured Eluate of MAb II with Activated Carbon-Cellulose Media and an Anion Exchange Media In this experiment, it was demonstrated that activated carbon alone and in combination with an ion exchange media is unique and unexpectedly effective for the removal of HCP derived from microbial feeds after a capture step.

A solution of E. coli lysate was spiked with mAb monoclonal antibody at 1.5 mg/mL and then captured with Protein A chromatography. The captured feed was treated with activated carbon packed in a column under flow-through conditions and then by a ChromaSorb™ AEX membrane.

Cells from a culture of E. coli were recovered by centrifugation. The supernatant was decanted off and the remaining cell pellet was suspended in a lysis buffer (25 mM Tris, 0.1 mM EDTA at pH 7) by vigorous shaking and stirring. Then a 0.4 mL, portion of a stock solution of 100 mM PMSF in ethanol was added. The suspension was split into fractions (~100 mL each) and subjected to sonication with 3 sec on and 4 sec off for 5 min. Following sonication the material was pooled and stored at −80 degrees C. for 48 hour. Then the solution was thawed and centrifuged at 4,500×g for 2 hours to remove the lysed cells. The supernatant was filtered with a Stericup-HV 0.45 μm Durapore membrane (1000 mL, catalogue number: SCHVU11RE, Millipore Corp. Billerica, Mass., 01821. USA). Then it was filtered through Stericup-GP 0.22 μm Millipore Express PLUS membrane (1000 mL, catalogue number: SCGPU11RE, Millipore Corp. Billerica, Mass., 01821, USA). The filtered lysate was than combined with 7.5 mL of 10 mg/mL of a mAb solution to give a solution spiked with 1.5 mL of the mAb. The pH of the solution was measure to be 7.7. The mAb in the spiked lysate was then captured with Protein A chromatography. Then 30 mL of the captured mAb was eluted at a low pH. The elution pH was raised from 3-4 to 7 by the drop wise addition of 1 M Tris and then filtered through Stericup-GP 0.22 m Millipore Express PLUS membrane (250 mL, catalogue number: SCGPU02RE, Millipore Corp. Billerica, Mass., 01821, USA). 1 mL of the pH adjusted elution was set aside for analysis.

A glass Omnifit Chromatography Column (10 mm diameter, 100 mm length) was loaded with 250 mg of Nuchar HD activated carbon (MeadWestVaco Corporation, Richmond, Va., USA) slurried in water to give a packed column volume of 1 mL. The column was equilibrated with 25 mM Tris buffer at pH 7. Then 29 mL of the mAb Protein A chromatography elution was passed through the activated carbon at 0.2 mL/min giving a residence time of 4 min. 1 mL of the activated carbon treated elution was set aside for analysis.

Then a 0.08 mL ChromaSorb™ device (EMD Millipore Corp. Billerica, Mass., 01821, USA) was wet according to instructions with water then flushed with flushed with 25 mM Tris pH 7. Then 27 mL of the activated carbon treated elution was passed through the ChromaSorb device at a flow rate of 0.5 mL/min giving of a residence time of 0.16 minutes. 1 mL of the activated carbon and ChromaSorb treated elution was set aside for analysis.

Each sample was analyzed for host cell protein (HCP) and IgG concentration. HCP analysis was performed using a commercially available E. Coli HCP ELISA kit from Cygnus Technologies. Southport, N.C. USA (catalog number F410), following the kit manufacturer's instructions. IgG concentration was measured using an Agilent HPLC system equipped with a Poros® A Protein A analytical column.

The results show that activated carbon alone and in combination with an AEX membrane was unexpectedly effective for the selective removal of HCP from captured elution of a microbial feed. The concentration of HCP in the elution was reduced by the activated carbon from 86 ng/mL (7 ppm) to 8 ng/mL (0.7 ppm) while the recovery of the mAb was 97% starting at a concentration of 11.5 g/L and recovered at 11.2 g/L. The concentration of HCP in the activated carbon treated elution was further reduced by the ChromaSorb AEX membrane to 3 ng/mL (0.3 ppm) with a 96% overall recovery of the mAb to give a final concentration of 11.1 g/L. This example demonstrates that activated carbon alone and in combination with an AEX media can be used to remove HCP derived from non-mammalian cells after a capture step.

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of reducing the level of one or more impurities in a sample containing an antibody interest and one or more impurities, the method comprising the steps of:
   (i) contacting a sample comprising an antibody and one or more impurities with a chromatography column containing affinity media;
   (ii) obtaining a first eluate of the sample;
   (iii) contacting the first eluate from (ii) in flow-through mode with a carbonaceous material;
   (iv) obtaining a second eluate of the sample;
   (v) contacting the second eluate with an anion exchange porous media membrane adsorber; and
   (vi) obtaining a third eluate of the sample,
   wherein the third eluate comprises a lower level of one or more impurities relative to the level of one or more impurities when the carbonaceous material is not used in the method.

2. A flow-through process for purifying an antibody from a Protein A eluate comprising the steps of:
   (i) contacting the eluate recovered from a Protein A chromatography column with activated carbon;
   (ii) contacting the flow-through sample from step (i) with an anion exchange chromatography media;
   (iii) contacting the flow-through sample from step (ii) with a cation exchange chromatography media; and
   (iv) obtaining the flow-through sample from step (iii) comprising the antibody,
   wherein the eluate flows continuously through steps (i)-(iii) and wherein level of one or more impurities in the flow-through sample after step (iii) is lower than the level in the eluate in step (i).

3. The method of claim 1, wherein the antibody is a monoclonal antibody or a polyclonal antibody.

4. The method of claim 2, wherein the antibody is a monoclonal antibody or a polyclonal antibody.

5. The method of claim 1, wherein carbonaceous material comprises activated carbon.

6. The method of claim 5, wherein the activated carbon comprises activated charcoal.

7. The method of claim 2, wherein the activated carbon comprises activated charcoal.

8. The method of claim 2, wherein the anion exchange chromatography media and/or the cation exchange chromatography media is packed in a column.

9. The method of claim 2, wherein the anion exchange chromatography media comprises a anion exchange resin.

10. The method of claim 2, wherein the cation exchange chromatography media comprises a cation exchange resin.

11. The method of claim 1, wherein the carbonaceous material is packed in a column, a sealed disposable device, a cartridge or a capsule.

12. The method of claim 2, wherein the activated carbon is packed in a column, a sealed disposable device, a cartridge or a capsule.

13. The method of claim 1, wherein the carbonaceous material is impregnated into a porous material.

14. The method of claim 2, wherein the activated carbon is impregnated into a porous material.

15. The method of claim 13, wherein the porous material is contained within a column, a sealed disposable device, a cartridge or a capsule.

16. The method of claim 14, wherein the porous material is contained within a column, a sealed disposable device, a cartridge or a capsule.

17. The method of claim 2, wherein the anion exchange chromatography media is a porous adsorptive media having a surface coating comprising one or more polymeric primary amines or copolymers thereof.

18. The method of claim 2, wherein the anion exchange chromatography media is a porous adsorptive media having a surface coating comprising one or more primary, secondary, tertiary and quaternary amines.

19. The method of claim 1, wherein the anion exchange porous media is a membrane adsorber.

20. A method of reducing the level of one or more impurities in a sample containing an antibody, the method comprising the steps of:
   providing a sample comprising an antibody and one or more impurities;
   contacting the sample with a suitable media to capture the antibody;
   obtaining an eluate of the sample following step (ii);
   contacting the eluate from step (iii) with a carbonaceous material;
   obtaining an eluate of the sample following step (iv);
   contacting the eluate from step (v) with an anion exchange media; and
   (vii) obtaining an eluate of the sample following step (vi),
   wherein the eluate from step (vii) comprises a lower level of one or more impurities relative to the level of one or more impurities when step (iv) is not performed.

21. The method of claim 20, wherein the antibody is a monoclonal antibody.

22. The method of claim 20, wherein the anion exchange media is a resin or a membrane.

23. The method of claim 20, wherein the carbonaceous material is activated carbon.

* * * * *